US010406246B2

(12) United States Patent
Eder et al.

(10) Patent No.: US 10,406,246 B2
(45) Date of Patent: Sep. 10, 2019

(54) DOUBLE-LABELED PROBE FOR MOLECULAR IMAGING AND USE THEREOF

(71) Applicant: DEUTSCHES KREBSFORSCHUNGSZENTRUM, Heidelberg (DE)

(72) Inventors: Matthias Eder, Mannheim (DE); Klaus Kopka, Dossenheim (DE); Martin Schaefer, Neckarsteinach (DE); Ulrike Bauder-Wuest, Schriesheim (DE); Uwe Haberkorn, Schwetzingen (DE)

(73) Assignee: Deutsches Kresbsforschungszentrum, Heidelberg (DE)

( * ) Notice: Subject to any disclaimer, the term of this patent is extended or adjusted under 35 U.S.C. 154(b) by 838 days.

(21) Appl. No.: 14/335,055

(22) Filed: Jul. 18, 2014

(65) Prior Publication Data
US 2015/0110715 A1    Apr. 23, 2015

Related U.S. Application Data

(60) Provisional application No. 61/892,022, filed on Oct. 17, 2013.

(51) Int. Cl.
| A61K 51/00 | (2006.01) |
| A61M 36/14 | (2006.01) |
| A61K 49/00 | (2006.01) |
| C07D 497/10 | (2006.01) |
| C07D 311/90 | (2006.01) |
| C07D 209/60 | (2006.01) |
| C07D 209/18 | (2006.01) |
| C07D 401/14 | (2006.01) |
| G01N 33/58 | (2006.01) |
| G01N 33/574 | (2006.01) |
| A61K 51/04 | (2006.01) |

(52) U.S. Cl.
CPC ...... A61K 49/0002 (2013.01); A61K 49/0021 (2013.01); A61K 49/0032 (2013.01); A61K 49/0041 (2013.01); A61K 49/0052 (2013.01); A61K 51/0406 (2013.01); A61K 51/0497 (2013.01); C07D 209/18 (2013.01); C07D 209/60 (2013.01); C07D 311/90 (2013.01); C07D 401/14 (2013.01); C07D 497/10 (2013.01); G01N 33/57492 (2013.01); G01N 33/582 (2013.01)

(58) Field of Classification Search
CPC ............ A61K 49/0002; A61K 51/0497; A61K 49/0041; A61K 49/0032; G01N 33/57492; G01N 33/582
USPC ...................................................... 424/1.65
See application file for complete search history.

(56) References Cited

FOREIGN PATENT DOCUMENTS

WO    WO 2010/108125    9/2010

OTHER PUBLICATIONS

Banerjee et al. Angew Chem. Int. Ed., 2011, 50, 9767-9170.*
Banerjee et al. Angew Chem. Int. Ed. (Supporting Information), 2011, 50, 1-19.*
Bertozzi et al. J. Org. Chem. 1991, 56, 4326-4329.*
Eder et al. J. Nucl. Med. 2013, 54, 1327-1330.*
Afshar-Oromieh, et al., "PET imaging with a [68Ga]gallium-labelled PSMA ligand for the diagnosis of prostate cancer, biodistribution in humans and first evaluation of tumour lesions" (2013), Eur J Nucl Med Mol Imaging, vol. 40(4) pp. 486-495.
Afshar-Oromieh, et al., "Comparison of PET imaging with a Ga-labelled PSMA ligand and F-choline-based PET/CT for the diagnosis of recurrent prostate cancer" (2014), Eur J Nucl Med Mol Imaging, vol. 41 pp. 11-20.
Banerjee, et al., "Sequential SPECT and optical imaging of experimental models of prostate cancer with a dual modality inhibitor of the prostate-specific membrane antigen" (2011), Angew Chem Int Ed Engl., vol. 50(39) pp. 9167-9170.
Eder, et al., "Tetrafluorophenolate of HBED-CC: a versatile conjugation agent for (68)Ga-labeled small recombinant antibodies" (2008), Eur J Nucl Med Mol Imaging, vol. 35(10) pp. 1878-1886.
Eder, et al., "ScVEGF-PEG-HBED-CC and scVEGF-PEG-NOTA conjugates: comparison of easy-to-label recombinant proteins for [68Ga]PET imaging of VEGF receptors in angiogenic vasculature" (2010), Nucl Med Biol., vol. 37(4) pp. 405-412.
Eder, et al., "68Ga-complex lipophilicity and the targeting property of a urea-based PSMA inhibitor for PET imaging" (2012), Bioconjug Chem., vol. 23(4) pp. 688-697.
Kolmakov, et al.," Polar red-emitting rhodamine dyes with reactive groups: synthesis, photophysical properties, and two-color STED nanoscopy applications" (2014), Chem. Eur. J., vol. 20 pp. 146-157.
Kolmakov, et al., "Red-emitting rhodamines with hydroxylated, sulfonated, and phosphorylated dye residues and their use in fluorescence nanoscopy" (2012), Chem. Eur. J., vol. 18 pp. 12986-12998.
Kularatne, et al., "Design, synthesis, and preclinical evaluation of prostate-specific membrane antigen targeted (99m)Tc-radioimaging agents" (2009), Mol Pharm., vol. 6(3) pp. 790-800.
Liu, et al., "Pseudoirreversible inhibition of prostate-specific membrane antigen by phosphoramidate peptidomimetics" (2008), Biochemistry, vol. 47(48) pp. 12658-12660.

(Continued)

Primary Examiner — Michael G. Hartley
Assistant Examiner — Sean R Donohue
(74) Attorney, Agent, or Firm — Kilpatrick Townsend & Stockton LLP

(57) ABSTRACT

The present invention relates to a compound or a pharmaceutically acceptable salt thereof having a chemical structure comprising: (A) at least one motif specifically binding to cell membranes of neoplastic cells; (B) at least one chelator moiety of radiometals; and (C) at least one dye moiety; wherein said compound has a molecular weight of not more than 5 kDa. Further, the invention refers to a method for producing such compound and to the in vivo and in vitro uses thereof.

11 Claims, 12 Drawing Sheets

(56) References Cited

OTHER PUBLICATIONS

Figure 1A:
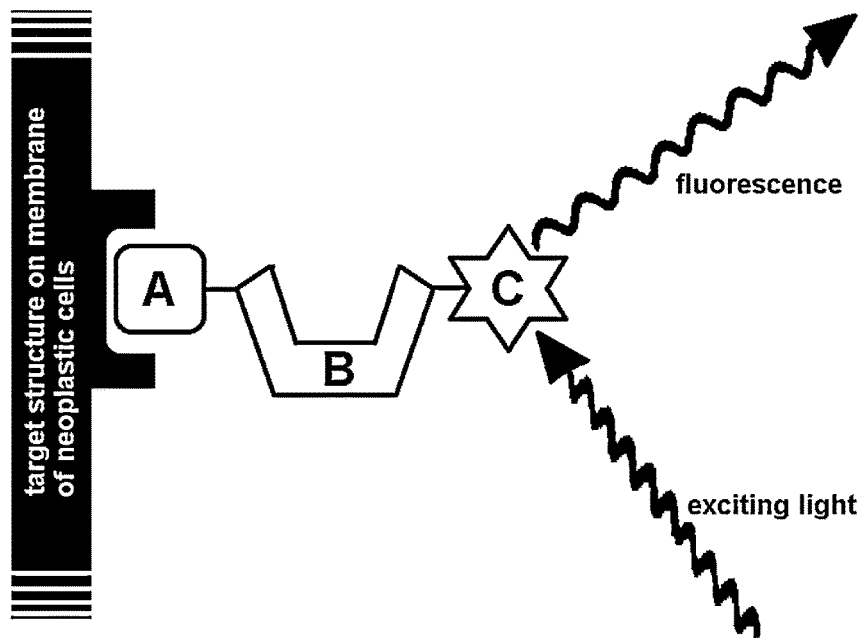

Schäfer, et al., "A dimerized urea-based inhibitor of the prostate-specific membrane antigen for 68Ga-PET imaging of prostate cancer" (2012), EJNMMI Res., vol. 2(1) pp. 23.

Schuhmacher, et al., "A new 68Ge/68Ga radioisotope generator system for production of 68Ga in dilute HCl" (1981), Int J Appl Radiat Isot, vol. 32 pp. 31-36.

Seibold, et al., "Bimodal imaging probes for combined PET and OI: recent developments and future directions for hybrid agent development" (2014), Biomed Res Int., vol. 2014 pp. 153741.

Chen, et al., "Synthesis and Biological Evaluation of Low Molecular Weight Fluorescent Imaging Agents for the Prostate-Specific Membrane Antigen", Bioconjugate Chem., 2012, 23, pp. 2377-2385.

Chen, et al., "A low molecular weight PSMA-based fluorescent imaging agent for cancer", Biochem. and Biophys. Res. Comm., 2009, 390, pp. 624-629.

Eder, et al., "Dual-label approach: optical dye conjugates of the PET tracer 68Ga-PSMA-HBED-CC", Abstract only, published on or after Jul. 20, 2013.

Eder, et al., "Dual-label approach: optical dye conjugates of the PET tracer 68Ga-PSMA-HBED-CC", Presentation, Oct. 20, 2013.

Huang, et al., "Dual-Modality Micro-Positron Emission Tomography/Computed Tomography and Near-Infrared Fluorescence Imaging of EphB4 in Orthotopic Glioblastoma Xenograft Models", Mol. Imaging Biol., 2014, 16, pp. 74-84.

Ghosh, et al., "Multimodal Chelation Platform for Near-infrared Fluorescence/Nuclear Imaging", Journal of Medicinal Chemistry, 2013, 56, pp. 406-416.

Eder et al., "Preclinical Evaluation of a Bispecific Low-Molecular Heterodimer Targeting Both PSMA and GRPR for Improved PET Imaging and Therapy of Prostate Cancer," *The Prostrate*, 74:659-668, 2014.

\* cited by examiner

DOUBLE-LABELED PROBE FOR MOLECULAR IMAGING AND USE THEREOF

This application claims priority to U.S. Provisional Application No. 61/892,022, filed on Oct. 17, 2013, the entirety of which is incorporated herein by reference.

The present invention relates to a compound or a pharmaceutically acceptable salt thereof having a chemical structure comprising: (A) at least one motif specifically binding to cell membranes of neoplastic cells; (B) at least one chelator moiety of radiometals; and (C) at least one dye moiety; wherein said compound has a molecular weight of not more than 5 kDa. Further, the invention refers to a method for producing such compound and to the in vivo and in vitro uses thereof.

During the recent years, molecular imaging has gained increasing importance for the diagnosis of neoplasia, in particular cancer. Physicians thereby are able to obtain valuable information on the size, localization and shape of a neoplastic pitch.

In order to visualize neoplastic tissue in vivo, a variety of techniques has been developed. Exemplarily, magnetic resonance imaging (MRI), radiography (in particular computer tomography (CT)), fluorescence molecular tomography (FMT) and positron emission tomography (PET) are methods regularly used for localization of neoplasia today.

However, these methods still bear severe drawbacks. While MRI achieves a high resolution of visualization and enables measurements without any stain, MRI renders it comparably difficult, when not even impossible, to reliably distinguish between healthy and neoplastic tissue. Radiography, such CT, also achieves a comparably high resolution but, like MRI, fails to clearly distinguish between diseased and healthy tissue and, additionally, often requires unwanted high doses of contrast agents. FMT in turn enables detecting a specifically stained tissue but typically bears a poor resolution and allows only detections of neoplasia located nearby the outer surface of the patient's body an does, additionally, not enable the visualization of the surrounding tissue what renders it difficult for the examiner to infer diagnostic conclusions and to decide on further treatment strategies. PET enables the detection of neoplasia inside the entire patient's body, but merely depicts a neoplasm itself and does, like FMT, not show the localization of a neoplasm insight its tissue context.

MRI and PET are regularly combined with another, sometimes in a single apparatus, in order to enable distinct detection of neoplasia and the surrounding tissue. This enables the precise localization of a neoplasm in its tissue context and further shows the shape and size of a neoplasm.

However, apparatuses for MRI and PET are rather large size apparatuses comprising parts surrounding the patient's body and, thereby, impeding contemporary surgical interventions. When molecular imaging by means of MRT and/or PET has once been completed, the surgeon intending to remove the neoplastic tissue has to assess the position, size and shape of the neoplastic tissue in the patient's body by mentally projecting the image obtained from molecular imaging onto the patient's body. In other words, while performing the surgery, the surgeon is unable to visually see the neoplastic tissue in the patient' body because, often, the neoplastic tissue does not or merely slightly appears different from the surrounding non-neoplastic tissue. Exemplarily, lymph knots including neoplastic cells are typically not distinguishable from their healthy counterparts. The surgeon thus has to either remember the respective localization of the neoplastic tissue seen by molecular imaging before or, from time to time, has to digress his attention from the patient's body and turn to the results obtained from the molecular imaging in order to mentally project these results onto the patient's body.

This procedure has the major drawback that the surgeon can never be entirely sure to have removed the entire neoplastic tissue. Therefore, often rather large parts of the tissue are removed, including large amounts of healthy tissue. And, otherwise, often residual parts of neoplastic tissue still remain in the patient.

Therefore, compounds bearing a cellular binding site binding to neoplastic cells (e.g., a prostate-specific membrane antigen (PSMA)), a fluorophore and a chelator, in particular an 1,4,7,10-tetraazacyclododecane-N,N',N",N"'-tetraacetic acid (DOTA) chelator have been developed (Banerjee et al., 2011; WO 2010/108125). Herein, both the chelator as well as the fluorophore are each conjugated via independent spacers to a common molecular backbone that is conjugated to the cellular binding site.

This approach however bears the significant disadvantage that the flexibility in using various dyes is limited. Indeed, it has been found that using chelators like DOTA bears significant disadvantages such as diminished binding to a target structure when not combined with particular fluorophore structures such as IRDye800CW as used by Banerjee et al. Therefore, the structures known in the art are not used in a modular manner. In particular, the dyes conjugated therewith are not freely selectable and several fluorophors regularly and preferably used in the art are not usable with this strategy.

Further, cell-staining structures comprising a fluorophore, a chelator and a motif binding to cellular markers which are present in various cell populations are known (cf., Seibold et al., 2014). These structures, however, do not comprise a motif specifically binding to cell membranes of neoplastic cells but rather to cellular structures present in various cell types including non-neoplastic physiological cells. Further, in these structures shown by Seibold et al., the binding site is not freely selectable in a modular manner, but rather integrated into the structure in a rather complex manner.

In the view of the above, there is still an unmet need for compounds that enable in vivo molecular imaging in a patient as well as imaging during a surgery that are easy to synthesize in a modular manner and widely flexible with respect to the selection of the dye.

Surprisingly, a compound enabling in vivo molecular imaging in a patient and, likewise, imaging during a surgery has been found. This compound is bimodal, thus, comprises at least one chelator moiety of radiometals enabling complexing a radiometal detectable by detecting its radioactivity and at least one dye moiety detectable by its visible properties. The one or more chelator(s) are herein conjugated, optionally via spacers, with at least one dye moiety at a first site of the chelator(s) and concomitantly conjugated with at least one motif specifically binding to cell membranes of neoplastic cells at another site of the chelator(s), such that a (A)-(B)-(C) structure is generated.

In a first aspect, the present invention refers to a compound or a pharmaceutically acceptable salt thereof having a chemical structure comprising:
(A) at least one motif specifically binding to cell membranes of neoplastic cells;
(B) at least one chelator moiety of radiometals; and
(C) at least one dye moiety;
wherein said compound has a molecular weight of not more than 5 kDa.

Preferably, the compound or pharmaceutically acceptable salt thereof has a chemical structure comprising:
(A) one motif specifically binding to cell membranes of neoplastic cells;
(B) one chelator moiety of radiometals; and
(C) one dye moiety;
wherein said compound has a molecular weight of not more than 5 kDa.

Preferably, the compound according to the present invention has the following molecular structure:

(A)-(B)-(C), wherein the "-" may be a bond via a spacer molecule or a direct bond, preferably a bond via a spacer molecule.

Therefore, in one aspect, the present invention refers to a compound or a pharmaceutically acceptable salt thereof having a chemical structure comprising:
(A) at least one motif specifically binding to cell membranes of neoplastic cells;
(B) at least one chelator moiety of radiometals; and
(C) at least one dye moiety;
wherein said compound has a molecular weight of not more than 5 kDa, and
wherein said compound has the following molecular structure:

(A)-(B)-(C), wherein the "-" may be a bond via a spacer molecule or a direct bond, preferably a bond via a spacer molecule.

This compound exemplarily enables a positron emission tomography (PET) scan as well as fluorescence imaging.

As used herein, the term "pharmaceutically acceptable salt" may be understood in the broadest sense as any charged form of the compound of the present invention. Depending on the chemical structure of the compound and on the environment it is dissolved in, the compound may, exemplarily, comprise one or more charged residue(s) selected from the group consisting of but not limited to carboxylate anion residue(s), primary ammonium cation(s), secondary ammonium cation residue(s), tertiary ammonium cation residue(s), primary phosphate anion residue(s), secondary phosphate anion residue(s), sulfate anion residue(s), sulfite anion residue(s) and an alkoxide residue(s). The counterions may be any ions known to be pharmaceutically acceptable in the art such as, e.g., acetate, fatty acid carboxylate, chloride, sodium ions, potassium ion, magnesium ion, calcium ion, aluminum ion, lithium ion, ammonium, phosphate, hydroxyl, proton and fluoride ion.

As used throughout the present invention, the term "motif" may be understood in the broadest sense as a molecular structure pattern that enables specific binding to cell membranes of neoplastic cells.

As used in the context of the present invention, the term "neoplastic cell" may be understood in the broadest sense as any cell that shows an abnormal growth and/or division rate, also including metaplastic and dysplastic cells. Typically, a neoplastic cell will tend to form a bulk of cells known as neoplasia. The growth of neoplastic cells typically is less or not coordinated with the normal tissues around it. The growth of a neoplastic cell preferably persists in the same excessive manner even after cessation of the stimuli. Neoplastic cells may form a benign neoplasia, a pre-malignant neoplasia (carcinoma in situ) or a malignant neoplasia (cancer). Neoplasia may also be characterized by the International Classification of Diseases Vol. 10 (ICD-10 nomenclature) in the version of 2013, i.e., as any pathological condition according to ICD-10 classes C00-D48. In the context of the present invention cancer also includes metastases.

Cancer in the sense of the present invention is any malignant neoplasia. Exemplarily, cancer may be a carcinoma (e.g., prostate carcinoma, breast carcinoma, lung carcinoma, pancreas carcinoma, liver carcinoma or colon carcinoma), a sarcoma (e.g. sarcoma in the bone, cartilage, fat and/or nerve tissue, or mesenchymal sarcoma), a lymphoma, a leukemia, germ cell (e.g., testicle or ovary cancer (seminoma and dysgerminoma, respectively)) or a blastoma e.g., liver blastoma).

The motif binds its target structure present on the surface of neoplastic cells with a higher affinity compared to other molecular structures.

Target structure preferably is typical for neoplastic cells. Therefore, the target structure may preferably be found on the surface of neoplastic cells exclusively or at a higher local concentration compared to normal, i.e., non-neoplastic cells. Accordingly, the local concentration of the target structure recognized by the motif (A) according to the present invention at the cell membrane of neoplastic cells preferably is at least 2 fold, more preferably at least 5 fold, even more preferably at least 10 fold, even more preferably at least 100 fold, even more preferably at least 500 fold higher compared to corresponding normal, i.e., non-neoplastic cells.

Preferably, the motif binds to its target structure on neoplastic cells with an at least 5 fold higher, more preferably at least 10 fold higher, even more preferably at least 20 fold higher, even more preferably at least 50 fold higher, in particular at least 100 fold higher affinity than to other molecular structures of the same charge and hydrophobicity in comparable chemical environments. Preferably, the motif binds to the target structure on cell membranes of neoplastic cells with a dissociation constant of not more than 10 µM, more preferably not more than 5 µM, even more preferably not more than 1 µM, even more preferably not more than 100 nM in particular not more than 50 nM.

Preferably, the motif comprises at least one naturally occurring amino acid moiety, more preferably at least two naturally occurring amino acid moieties.

As used throughout the present invention, the terms "moiety", "residue" and "rest" in the context of a chemical structure may be understood interchangeably in the broadest sense as a part of a molecule tightly bound to the other parts of the molecule, in particular via a covalent bond. Further, the terms "conjugated to" and "bound to" as used herein may be understood interchangeably.

Preferably, the motif comprises at least one non-proteinogenic amide bond, more preferably at least two non-proteinogenic amide bonds. More preferably, the motif comprises at least one naturally occurring amino acid moiety conjugated via a non-proteinogenic amide bond, even more preferably at least two naturally occurring amino acid moieties conjugated via non-proteinogenic amide bonds.

Preferably, the motif specifically binding to cell membranes of neoplastic cells comprises not more than 20 amino acid moieties, more preferably not more than ten amino acid moieties, even more preferably not more than five amino acid moieties, even more preferably not more than four amino acid moieties, in particular not more than three amino acid moieties.

Preferably, the motif further comprises at least one urea moiety, more preferably at least one urea moiety covalently bound to two amino acids via amide bond formation.

The at least one motif specifically binding to cell membranes of neoplastic cells (A) may be covalently or non-covalently (e.g., via complex formation) linked with the at least one chelator moiety of radiometals (B) and/or the at least one dye moiety (C). Preferably, it is covalently conjugated to the at least one chelator moiety of radiometals (B) and/or the at least dye moiety (C), more preferably to the at least one chelator moiety of radiometals (B), in particular to one chelator moiety of radiometals (B). Such covalent conjugation to a chelator moiety of radiometals (B) may be the formation of a covalent bond directly between the motif (A) and the chelator (B) or may be covalent linkage via a spacer. In this context, preferably, a spacer is of not more than 5 nm in length, preferably of not more than 2 nm in length, in particular of not more than 1 nm in length. The motif may preferably be conjugated to chelator moiety of radiometals (B) via the epsilon amino group of a lysine moiety.

The term "chelator moiety" as used in the context of the present invention may be understood in the broadest sense as any moiety that is able to form a complex with a radiometal under suitable conditions. Herein, the terms "chelator moiety", "chelant", "chelating moiety", "sequestering moiety" and "complexing moiety" may be understood interchangeably. The chelator moiety is preferably an organic moiety. Complexing by chelation preferably involves the formation or presence of two or more separate coordinate bonds between a polydentate (multiple bonded) ligand and a single central radiometal. The common definition of the International Union of Pure and Applied Chemistry (IUPAC) on chelation, interpreted in its broadest sense, may also be noted. Chelator moieties as used herein will typically bear at least two heteroatoms enabling an interaction with a radiometal. Preferably, the chelator moiety will have at least three, in particular at least four heteroatoms enabling an interaction with a radiometal.

A radiometal as used in the context of the present invention may be understood in the broadest sense as any radioactive metal or radioactive metal ion, i.e., a metal or metal ion that emits radioactive emission. It may be a metal or metal ion that is typically radioactive or a radioactive isotope of a metal that also has non-radioactive isotopes. Exemplarily, a radiometal may be a radioactive isotope of gallium (Ga) (e.g., $^{68}$Ga), copper (e.g., $^{64}$Cu), zirconium (e.g., $^{89}$Zr), scandium (e.g., $^{44}$Sc), rubidium (e.g., $^{82}$Rb), cobalt (e.g., $^{60}$Co), strontium (e.g., $^{90}$Sr) or technetium (e.g., $^{99m}$Tc). Preferably, the radiometal is a radioactive isotope of $^{68}$Ga, $^{64}$Cu, $^{89}$Zr, $^{44}$Sc, $^{99m}$Tc or $^{82}$Rb, more preferably $^{68}$Ga, $^{64}$Cu, $^{89}$Zr, $^{44}$Sc, or $^{82}$Rb, even more preferably $^{68}$Ga or $^{64}$Cu, in particular $^{68}$Ga. The person skilled in the art will know several examples for chelator moieties suitable for complexing each of the aforementioned radiometals and may select the chelator moiety accordingly. Exemplarily, a chelator moiety suitable for complexing $^{99m}$Tc or $^{82}$Rb, may or may not differ from that suitable for complexing $^{68}$Ga or $^{64}$Cu.

Preferably, the radiometal is such that has a half-life of no longer than four days, more preferably of no longer than one day, even more preferably no longer than 12 h, even more preferably, not more than 6 h, even more preferably not more than 3 h, even more preferably not more than 2.5 h, even more preferably not more than 120 min, even more preferably not more than 100 min, even more preferably not more than 80 min, in particular not more than 70 min.

The radiometal may be obtained from any source suitable for this purpose. The radiometal may be obtained and isolated from nature or artificially be generated such as, e.g., $^{68}$Ga from a gallium-68-generator. The person skilled in the art will know how to obtain the respective radiometal.

As used in the context of the present invention, the terms "dye moiety", "label" and "stain" may be understood interchangeably in the broadest sense as any moiety that provides a visible stain. Preferably, the dye moiety may be a fluorescent dye moiety and/or a chromatic moiety, particularly preferably the dye moiety is a fluorescent dye moiety.

A fluorescent dye moiety as used herein may be understood in the broadest sense as any dye moiety enabling fluorescence detection. Preferably, such fluorescence detection is in a range of from 400 to 1000 nm, i.e. in the visible spectrum and in the Near Infrared (NIR) spectrum, in particular in a range of from 400 to 800 nm, i.e. in the visible spectrum. Preferably, the fluorescence signal emitted by the fluorescence dye moiety is well-distinguishable from the autofluorescence of the neoplasia and the surrounding tissue. Numerous fluorescent dye moieties are known in the art, and will be readily apparent to one of ordinary skill. Many fluorescent dyes are commercially available with activated groups used to react with protein sidechains or other compounds such as the compound of the present invention, preferably the spacer y of the compound of the present invention, in particular thereby forming the group e' as defined herein.

Preferably, the fluorescence dye moiety in the context of the present invention is a small-molecule dye, i.e., a fluorescence dye moiety having a molecular weight (MW) of not more than 1000 Da, preferably not more than 750 Da, in particular nor more than 500 Da. Exemplarily, an indocyanine green (ICG) dye moiety (e.g., a dye moiety derived from a sulfo ICG moiety), a fluorescence dye moiety may be a fluorescein-type dye (e.g., derived from fluorescein isothiocyanate (FITC), carboxyfluorescein or fluorescein), a rhodamine type dye (e.g., derived from rhodamine G, rhodamine or tetramethylrhodamine (TAMRA)), a cyanine dye (e.g., derived from sulfoCy5, cyanine 5.5, Cy2, Cy3, Cy3.5, Cy5, Cy5.5, Cy7, Cy7.5, an AlexaFluor dye (e.g., Alexa Fluor 488, Alexa Fluor 546, Alexa Fluor 647, Alexa Fluor 680, Alexa Fluor 750), a dye moiety derived from DyLight (e.g., DyLight 750, DyLight 800), a dye moiety derived from a FluoProbe dye, a dye moiety derived from a sulfo Cy dyes, a seta dye, or S0387), an infrared dye (e.g., derived from IRDye 800CW, IRDye 800RS, IRDye 800, IRDye 700, IRDye 700DX, IRDye 680 or IRDye 680LT), a dye moiety derived from 5-aminovulinic acid (5-ALA), a phenoxacin dye (e.g., derived from Nile red or Nile blue), a dye moiety derived from an allophycocyanin dye, a dye moiety derived from a berberin dye, a dye moiety derived from quinine or from a fluorescence quinine derivative, a dye moiety derived from cumarine, a dye moiety derived from 4',6-diamidino-2-phenylindole (DAPI), a dye moiety derived from epicocconone, 5-({2-[(iodoacetyl)amino]ethyl}amino)naphthalene-1-sulfonic acid (IAEDANS), an Atto dye (e.g., derived from ATTO 390, ATTO 425, ATTO 465, ATTO 488, ATTO 495, ATTO 520, ATTO 532, ATTO 550, ATTO 565, ATTO 590, ATTO 594, ATTO 610, ATTO 611X, ATTO 620, ATTO 633, ATTO 635, ATTO 637, ATTO 647, ATTO 647N, ATTO 655, ATTO 665, ATTO 680, ATTO 700, ATTO 725, ATTO 740), a Visen dye (e.g. derived from VivoTag680, VivoTag750) or a dye moiety derived from a HOECHST dye).

Further examples of rhodamine type dye moieties usable in the context of the present invention may be those derivable from the fluorophores shown by Kolmakov et al. (cf., Kolamkov et al., 2012; Kolmakov et al., 2014), such as e.g., KK114 or Abberior Star 635P shown therein.

Additionally or alternatively, the dye moiety may also be chromatic, i.e., provoke a colour perception when illuminated by any light. Such chromatic effect may be provoked by absorbing light of one or more particular wavelength range(s) in the visible range (i.e., in range(s) from approximately 400 nm to approximately 800 nm) and/or by emitting light of one or more particular wavelength range(s) in the visible range. Preferably, the colour is different from the neoplasia and the surrounding tissue intended to be examined. Therefore, a dye moiety, when not intended for fluorescence detection, is preferably not red or brown, but rather preferably blue or green. When the dye moiety is intended for fluorescence detection, the difference in colour will typically play a minor role as long as the fluorescence is detectable over the autofluorescence background. Preferably, the chromatic dye moiety in the context of the present invention is a small-molecule dye, i.e., a dye moiety having a molecular weight (MW) of not more than 1000 Da, preferably not more than 750 Da, in particular nor more than 500 Da.

The dye moiety (C) may be covalently or non-covalently (e.g., via complex formation) linked with the at least one motif specifically binding to cell membranes of neoplastic cells (A) and/or the at least one chelator moiety of radiometals (B). Preferably, it is covalently conjugated to the at least one motif specifically binding to cell membranes of neoplastic cells (A) and/or the at least one chelator moiety of radiometals (B), more preferably to the at least one chelator moiety of radiometals (B), in particular to one chelator moiety of radiometals (B). Such covalent conjugation to a chelator moiety of radiometals (B) may be the formation of a covalent bond directly between the dye moiety (C) and the chelator moiety of radiometals (B) or may be covalent linkage via a spacer. Preferably, a spacer is of not more than 5 nm in length, preferably of not more than 2 nm in length, in particular of not more than 1 nm in length.

Accordingly, the molecular distance between the motif specifically binding to cell membranes of neoplastic cells (A) and the dye moiety (C) is preferably not longer than 20 nm, more preferably not longer than 10 nm, in particular not longer than 5 nm.

This may, depending on the chemical properties of the fluorescence dye moiety/moieties in the compound of the present invention and the presence of fluorophore(s) and/or quenchers on the surface of the target cells, i.e., the cell membranes of the respective neoplastic cells, also enable to observe effects such as fluorescence energy transfer (FRET) and/or fluorescence quenching upon binding of the compound according to the present invention to said cell membranes. Additionally or alternatively, the presence of the fluorescence dye moiety/moieties also enables to conduct further examination methods based on fluorescence such as, e.g., fluorescence recovery after photobleaching (FRAP), fluorescence loss in photobleaching (FLIP). These methods may provide information on the mobility of the compound or salt thereof bound to or associated with the cell membranes of a neoplastic cell.

Preferably, the compound according to the present invention has a molecular weight (MW) of not more than 4 kDa, more preferably not more than 3.5 kDa, even more preferably not more than 3 kDa, in particular not more than 2.5 kDa.

According to the present invention, the compound may have any stoichiometry of
(A) at least one motif specifically binding to cell membranes of neoplastic cells;
(B) at least one chelator moiety of radiometals; and
(C) at least one dye moiety.

Preferably, the stoichiometry of (A):(B):(C) is 1:1:1. Therefore, the present invention preferably refers to a compound or a pharmaceutically acceptable salt thereof having a chemical structure comprising:
(A) one motif specifically binding to cell membranes of neoplastic cells;
(B) one chelator moiety of radiometals; and
(C) one dye moiety;
wherein said compound has a molecular weight of not more than 5 kDa, preferably not more than 4 kDa, more preferably not more than 3.5 kDa, even more preferably not more than 3 kDa, in particular not more than 2.5 kDa.

In a preferred embodiment, the compound has the following molecular structure:

(A)-(B)-(C), wherein (A), (B) and (C) are defined as above, preferably wherein (B) and (C) are conjugated with another via a spacer molecule.

More preferably, also (A) and (B) are conjugated with another via a spacer molecule.

Accordingly, in a preferred embodiment, the compound has the following molecular structure:

(A)-(B)-(C), wherein (A), (B) and (C) are defined as herein, wherein (B) and (C) and (A) and (B) are conjugated with another via a spacer molecule.

Accordingly, in a preferred embodiment, the compound has the following molecular structure:

(A)-x-(B)-y-(C), wherein x and y represent independently from another each a spacer molecule.

In an alternative aspect, the molecular structure of such compound may be selected from any of the following molecular structures:

(A)-(C)-(B), or (B)-(A)-(C), wherein the "-" may be a direct bond or a bond via a spacer molecule. The spacer molecules may be also those defined herein, thus, each x or y.

As mentioned above, motif specifically binding to cell membranes of neoplastic cells (A) may bind to any molecular structures typically found on neoplastic cells and may have any molecular structure.

In a preferred embodiment, the motif specifically binding to cell membranes of neoplastic cells (A) is a motif specifically binding to cell membranes of cancerous cells, preferably wherein said motif comprises a prostate-specific membrane antigen (PSMA) binding motif.

Herein, the terms "prostate-specific membrane antigen", "prostate-specific membrane antigen binding motif" and "PSMA binding motif", may be understood interchangeably.

In a more preferred embodiment, the motif specifically binding to cell membranes of neoplastic cells (A) is a PSMA binding motif having the following structure:

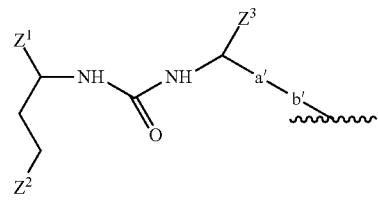

wherein $Z^1$, $Z^2$ and $Z^3$ are each independently from another selected from the group consisting of —C(O)OR$^1$, —SO$_2$R$^1$, —SO$_3$R$^1$, —SO$_4$R$^1$, —PO$_2$R$^1$, —PO$_3$R$^1$, and —PO$_4$R$^1$R$^2$, wherein R$^1$ and R$^2$ are independently from another H or a C$_{1-4}$-alkyl residue;

wherein a' represents a —[CH$_2$]$_o$— residue, wherein o is an integer from 1 to 4, preferably wherein o is 3 or 4, in particular wherein o is 4.

wherein b' represents a residue selected from the group consisting of —NH—, —C(O)— and —O—, in particular wherein b' is —NH—; and wherein the wavy line indicates the conjugation site to the chelator moiety of radiometals (B), preferably conjugated via a spacer molecule x.

As used throughout the present application, the terms "alkyl", "alkyl residue" and "alkyl group" and "alkyl moiety" may be understood as a straight-chain or branched saturated hydrocarbon chain. "Straight-chain" may be also designated as "unbranched" or "linear". Preferably, the alkyl is a straight chain.

"C$_{1-4}$-alkyl residue" means an alkyl chain having 1-4 carbon atoms, e.g. methyl, ethyl, n-propyl, isopropyl, n-butyl, isobutyl, sec-butyl or tert-butyl. Preferably, an C$_{1-4}$-alkyl residue is a straight-chain alkyl selected from the group consisting of methyl, ethyl, n-propyl and n-butyl.

In a particularly preferred embodiment, the motif specifically binding to cell membranes of neoplastic cells (A) is a PSMA binding motif having the following structure:

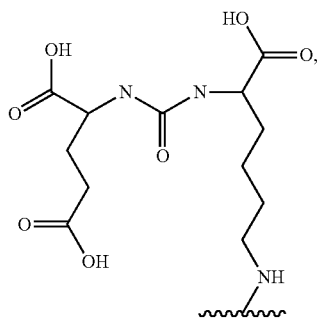 [SMILES: *NCCCCC(NC(=O)NC(CCC(=O)O)C(=O)O)C(=O)O]

wherein the wavy line indicates the conjugation site to the chelator moiety of radiometals (B), preferably conjugated via a spacer molecule x.

The spacers x and y may be any spacers usable for such probes in vivo and/or in vitro. In this context, preferably, a spacer is of not more than 5 nm in length, preferably of not more than 2 nm in length, in particular of not more than 1 nm in length.

The spacer x is preferably flexible and does preferably not bear aromatic residues when the chelator moiety of radiometals (B) bears aromatic moieties.

In a preferred embodiment, the spacer x bears the following structure:

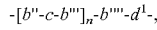

wherein b" is selected from the group consisting of —C(O)—, —NH—, and —O—, and wherein b' of (A) and b" of the spacer x together form an amide group or an ester group, preferably b" is —C(O)— and b" and b' together form an amide group;

wherein c represents a residue selected from the group consisting of an C$_{1-8}$-alkylene wherein one or more —CH$_2$— moieties may optionally be replaced by —O—, preferably c is without any replacement, preferably wherein c is a residue selected from the group consisting of an unsubstituted C$_{1-8}$-alkylene, —CH$_2$—(O—CH$_2$—CH$_2$)$_2$—CH$_2$—, —(CH$_2$)$_2$—(O—CH$_2$—CH$_2$)$_2$—, —(CH$_2$)$_3$—O—CH$_2$—CH$_2$—O—CH$_2$—, —CH$_2$—O—(CH$_2$)$_6$—, —(CH$_2$)$_2$—O—(CH$_2$)$_5$—, —(CH$_2$)$_3$—O—(CH$_2$)$_4$—, —(CH$_2$)$_4$—O—(CH$_2$)$_3$—, —(CH$_2$)$_5$—O—(CH$_2$)$_2$—, —(CH$_2$)$_6$—O—CH$_2$—, —CH$_2$—(O—CH$_2$—CH$_2$)$_2$—, —(CH$_2$)$_2$—O—CH$_2$—CH$_2$—O—CH$_2$—, —CH$_2$—O—(CH$_2$)$_5$—, —(CH$_2$)$_2$—O—(CH$_2$)$_4$—, —(CH$_2$)$_3$—O—(CH$_2$)$_3$—, —(CH$_2$)$_4$—O—(CH$_2$)$_2$—, —(CH$_2$)$_5$—O—CH$_2$—, —CH$_2$—O—CH$_2$—CH$_2$—O—CH$_2$—, —CH$_2$—O—(CH$_2$)$_4$—, —(CH$_2$)$_2$—O—(CH$_2$)$_3$—, —(CH$_2$)$_3$—O—(CH$_2$)$_2$—, —(CH$_2$)$_4$—O—CH$_2$—, —CH$_2$—O—(CH$_2$)$_3$—, —(CH$_2$)$_2$—O—(CH$_2$)$_2$—, —(CH$_2$)$_3$—O—CH$_2$—, —CH$_2$—O—(CH$_2$)$_2$—, —(CH$_2$)$_2$—O—CH$_2$—, and —CH$_2$—O—CH$_2$—, in particular a residue selected from the group consisting of a butylene residue, a pentylene residue or a hexylene residue;

wherein b'" is selected from the group consisting of, —NH—, —C(O)— and —O—, wherein b"" is selected from the group consisting of —C(O)—, —NH— and —O—;

and wherein b'" and b"" or b' and b"" together form an amide group or an ester group, in particular wherein b'" is —NH— and b"" and b"" together form an amide group;

wherein d$^1$ is —[CH$_2$]$_p$—, wherein p is 1 or 2, in particular 2; and wherein n is 0 or 1.

As used throughout the present application, the term "alkylene" means a straight-chain or branched saturated hydrocarbon chain wherein two moieties of a molecule are linked by the alkylene residue. "Straight-chain" may be also designated as "unbranched" or "linear". Each hydrogen of an alkylene carbon may or may not be replaced by a substituent (i.e., may be substituted or unsubstituted) as further specified.

"C$_{1-8}$ alkylene residue" means an alkylene chain having 1-8 carbon atoms, e.g. —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, —CH$_2$—C(CH$_3$)$_2$—, —C(CH$_2$—CH$_3$)$_2$—, —CH(CH$_2$—CH$_3$)—, —CH$_2$—CH(CH$_3$)(CH$_2$—CH$_3$)—, —CH(CH$_3$)(CH$_2$—CH$_3$)—, —(CH$_2$)$_4$—, —(CH$_2$)$_5$—, —(CH$_2$)$_6$—, —(CH$_2$)$_7$—, —(CH$_2$)$_8$—, etc., when two moieties of a molecule are linked by the alkylene group.

Preferably, in the context of the residue c of the spacer x, an C$_{1-8}$ alkylene residue is preferably a straight-chain, i.e., unbranched, C$_{1-8}$ alkylene residue, i.e., selected from the group consisting of —CH$_2$—, —CH$_2$—CH$_2$—, —(CH$_2$)$_3$—, —(CH$_2$)$_4$—, —(CH$_2$)$_5$—, —(CH$_2$)$_6$—, —(CH$_2$)$_7$—, and —(CH$_2$)$_8$—, in which optionally one or more —CH$_2$— moieties may be replaced by —O—. Examples are shown above.

In a more preferred embodiment, the spacer x bears the following structure:

wherein q is an integer from 1 to 8, preferably 4, 5 or 6, in particular 5;

wherein n is 0 or 1; and wherein p is 1 or 2, in particular 2.

In a particularly preferred embodiment, the spacer x bears the following structure:

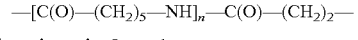

wherein n is 0 or 1.

The spacer y preferably is rather hydrophilic.

In a preferred embodiment, the spacer y bears the following structure:

-$d^2$-e-[f-e']$_m$- wherein $d^2$ is —[CH$_2$]$_r$—, wherein r is 1 or 2, in particular 2; and
wherein e is selected from the group consisting of —C(O)—NH—, —NH—C(O)—, —C(O)—O—, —O—C(O)—, —NH—C(O)—NH—, —NH—C(S)—NH—,

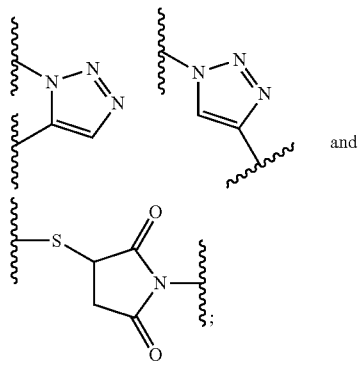
and wherein one of the wavy lines indicates the conjugation site to $d^2$ and the other wavy line indicates the conjugation site to f, in particular wherein e is —C(O)—NH—;
wherein each f independently represents a residue selected from the group consisting of an C$_{1-10}$-alkylene wherein one or more —CH$_2$— moieties may optionally be replaced by —O— or —NH—, and wherein f is unsubstituted or substituted with one or more groups independently selected from the group consisting of —NH$_2$, —COOH and R$^3$,
wherein R$^3$ is selected from the group consisting of —(CH$_2$)$_2$—COOH, —(CH$_2$)$_4$—NH$_2$, —(CH$_2$)$_4$—N$^+$(CH$_3$)$_3$+X$^-$, —CH$_2$—COOH, —CH$_2$—SH, —CH$_2$—SO$_3$H, and

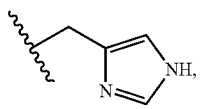

wherein X$^-$ is a pharmaceutically acceptable negatively charged counterion;
in particular a residue selected from the group consisting of —(CH$_2$)$_2$—(O—CH$_2$—CH$_2$)$_2$—, —CH$_2$—(O—CH$_2$—CH$_2$)$_2$—CH$_2$—, and —(CH$_2$)$_3$—O—CH$_2$—CH$_2$—O—CH$_2$—;
preferably wherein f is selected from the group consisting of —CH$_2$—(O—CH$_2$—CH$_2$)$_2$—CH$_2$—, —(CH$_2$)$_2$—(O—CH$_2$—CH$_2$)$_2$—, —(CH$_2$)$_2$—(CH$_2$—CH$_2$—O)$_2$—(CH$_2$)$_2$—, —(CH$_2$)$_3$—(CH$_2$—CH$_2$—O)$_2$—CH$_2$—, —(CH$_2$—CH$_2$—O)$_3$—CH$_2$—, —(CH$_2$)$_2$—(CH$_2$—CH$_2$—O)$_2$—CH$_2$—, —(CH$_2$)$_2$—(CH$_2$—CH$_2$—NH)$_2$—(CH$_2$)$_2$—, —(CH$_2$)$_3$—(CH$_2$—CH$_2$—NH)$_2$—CH$_2$—, —(CH$_2$—CH$_2$—NH)$_3$—CH$_2$—, —(CH$_2$)$_2$—(CH$_2$—CH$_2$—NH)$_2$—CH$_2$—, —(CH$_2$)$_3$—O—CH$_2$—CH$_2$—O—CH$_2$—, —CH$_2$—O—(CH$_2$)$_6$—, —(CH$_2$)$_2$—O—(CH$_2$)$_5$—, —(CH$_2$)$_3$—O—(CH$_2$)$_4$—, —(CH$_2$)$_4$—O—(CH$_2$)$_3$—, —(CH$_2$)$_5$—O—(CH$_2$)$_2$—, —(CH$_2$)$_6$—O—CH$_2$—, —CH$_2$—(O—CH$_2$—CH$_2$)$_2$—, —(CH$_2$)$_2$—O—CH$_2$—CH$_2$—O—CH$_2$—, —CH$_2$—O—(CH$_2$)$_5$—, —(CH$_2$)$_2$—O—(CH$_2$)$_4$—, —(CH$_2$)$_3$—O—(CH$_2$)$_3$—, —(CH$_2$)$_4$—O—(CH$_2$)$_2$—, —(CH$_2$)$_5$—O—CH$_2$—, —CH$_2$—O—CH$_2$—CH$_2$—O—CH$_2$—, —CH$_2$—O—(CH$_2$)$_4$—, —(CH$_2$)$_2$—O—(CH$_2$)$_3$—, —(CH$_2$)$_3$—O—(CH$_2$)$_2$—, —(CH$_2$)$_4$—O—CH$_2$—, —CH$_2$—O—(CH$_2$)$_3$—, —(CH$_2$)$_2$—O—(CH$_2$)$_2$—, —(CH$_2$)$_3$—O—CH$_2$—, —CH$_2$—O—(CH$_2$)$_2$—, —(CH$_2$)$_2$—O—CH$_2$—, —CH$_2$—O—CH$_2$—, —(CH$_2$)$_3$—O—, —CH$_2$—O—(CH$_2$)$_2$—O—CH$_2$—, —CH$_2$—O—(CH$_2$)$_2$—O—(CH$_2$)$_2$—, —(CH$_2$)$_3$—O—CH$_2$—CH$_2$—, —CH$_2$—O—(CH$_2$)$_3$—O—CH$_2$—, —(CH$_2$)$_3$—(O—CH$_2$—CH$_2$)$_2$—, —CH$_2$—(O—CH$_2$—CH$_2$)$_2$—(CH$_2$)$_2$—, —CH$_2$—(O—CH$_2$—CH$_2$)$_2$—(CH$_2$)$_3$—, —CH$_2$—(O—CH$_2$—CH$_2$)$_3$—, —(CH$_2$)$_2$—(O—CH$_2$—CH$_2$)$_2$—CH$_2$—, —CH$_2$—(O—CH$_2$—CH$_2$)$_2$—(CH$_2$)$_2$—, and —(CH$_2$)$_3$—(O—CH$_2$—CH$_2$)$_2$—, —CH$_2$—(NH—CH$_2$—CH$_2$)$_2$—CH$_2$—, —(CH$_2$)$_2$—(NH—CH$_2$—CH$_2$)$_2$—, —(CH$_2$)$_3$—NH—CH$_2$—CH$_2$—NH—CH$_2$—, —CH$_2$—NH—(CH$_2$)$_6$—, —(CH$_2$)$_2$—NH—(CH$_2$)$_5$—, —(CH$_2$)$_3$—NH—(CH$_2$)$_4$—, —(CH$_2$)$_4$—NH—(CH$_2$)$_3$—, —(CH$_2$)$_5$—NH—(CH$_2$)$_2$—, —(CH$_2$)$_6$—NH—CH$_2$—, —CH$_2$—(NH—CH$_2$—CH$_2$)$_2$—, —(CH$_2$)$_2$—NH—CH$_2$—CH$_2$—NH—CH$_2$—, —CH$_2$—NH—(CH$_2$)$_5$—, —(CH$_2$)$_2$—NH—(CH$_2$)$_4$—, —(CH$_2$)$_3$—NH—(CH$_2$)$_3$—, —(CH$_2$)$_4$—NH—(CH$_2$)$_2$—, —(CH$_2$)$_5$—NH—CH$_2$—, —CH$_2$—NH—CH$_2$—CH$_2$—NH—CH$_2$—, —CH$_2$—NH—(CH$_2$)$_4$—, —(CH$_2$)$_2$—NH—(CH$_2$)$_3$—, —(CH$_2$)$_3$—NH—(CH$_2$)$_2$—, —(CH$_2$)$_4$—NH—CH$_2$—, —CH$_2$—NH—(CH$_2$)$_3$—, —(CH$_2$)$_2$—NH—(CH$_2$)$_2$—, —(CH$_2$)$_3$—NH—CH$_2$—, —CH$_2$—NH—(CH$_2$)$_2$—, —(CH$_2$)$_2$—NH—CH$_2$—, —CH$_2$—NH—CH$_2$—, —(CH$_2$)$_3$—(NH—CH$_2$—CH$_2$)$_2$—CH$_2$—, —(CH$_2$)$_2$—(NH—CH$_2$—CH$_2$)$_2$—(CH$_2$)$_2$—, —CH$_2$—(NH—CH$_2$—CH$_2$)$_2$—(CH$_2$)$_3$, —CH$_2$—(NH—CH$_2$—CH$_2$)$_3$, —(CH$_2$)$_2$—(NH—CH$_2$—CH$_2$)$_2$—CH$_2$—, —CH$_2$—(NH—CH$_2$—CH$_2$)$_2$—(CH$_2$)$_2$—, —(CH$_2$)$_3$—(NH—CH$_2$—CH$_2$)$_2$—, —CH$_2$—O—(CH$_2$)$_8$—, —(CH$_2$)$_2$—O—(CH$_2$)$_7$—, —(CH$_2$)$_3$—O—(CH$_2$)$_6$—, —(CH$_2$)$_4$—O—(CH$_2$)$_5$—, —(CH$_2$)$_5$—O—(CH$_2$)$_4$—, —(CH$_2$)$_6$—O—(CH$_2$)$_3$—, —(CH$_2$)$_7$—O—(CH$_2$)$_2$—, —(CH$_2$)$_8$—O—CH$_2$—, —CH$_2$—O—(CH$_2$)$_7$—, —(CH$_2$)$_2$—O—(CH$_2$)$_6$—, —(CH$_2$)$_3$—O—(CH$_2$)$_5$—, —(CH$_2$)$_4$—O—(CH$_2$)$_4$—, —(CH$_2$)$_5$—O—(CH$_2$)$_3$—, —(CH$_2$)$_6$—O—(CH$_2$)$_2$—, —(CH$_2$)$_7$—O—CH$_2$—, —CH$_2$—NH—(CH$_2$)$_8$—, —(CH$_2$)$_2$—NH—(CH$_2$)$_7$—, —(CH$_2$)$_3$—NH—(CH$_2$)$_6$—, —(CH$_2$)$_4$—NH—(CH$_2$)$_5$—, —(CH$_2$)$_5$—NH—(CH$_2$)$_4$—, —(CH$_2$)$_6$—NH—(CH$_2$)$_3$—, —(CH$_2$)$_7$—NH—(CH$_2$)$_2$—, —(CH$_2$)$_8$—NH—CH$_2$—, —CH$_2$—NH—(CH$_2$)$_7$—, —(CH$_2$)$_2$—NH—(CH$_2$)$_6$—, —(CH$_2$)$_3$—NH—(CH$_2$)$_5$—, —(CH$_2$)$_4$—NH—(CH$_2$)$_4$—, —(CH$_2$)$_5$—NH—(CH$_2$)$_3$—, —(CH$_2$)$_6$—NH—(CH$_2$)$_2$—, —(CH$_2$), —NH—CH$_2$—, —CH(NH$_2$)—CH$_2$—, —CH$_2$—CH(NH$_2$)—, —CH(COOH)—CH$_2$—, —CH$_2$—CH(COOH)—, and —CH(R$^3$)—, wherein each e' is independently selected from the group consisting of a chemical bond, —NH—C(O)—, —C(O)—NH—, —C(O)—O— and —O—C(O)—, —NH—C(O)—NH—, —NH—C(S)—NH—, —C(O)—N(CH$_3$)—, —N(CH$_3$)—C(O)—, —NH—C(S)—, —C(S)—NH—,

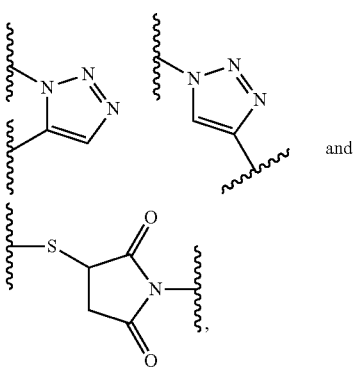
and wherein one of the wavy lines indicates the conjugation site to f and the other wavy line indicates the conjugation site to the at least one dye moiety (C), in particular wherein e' is —NH—C(O)—; and wherein m indicates an integer from 0 to 8; and Therefore, the at least one dye moiety (C) may be conjugated in various ways. Hereby, the examples of (C) enlisted below indicate each of the enlisted dye moieties (C) itself, i.e., without the functional group of its precursor that is conjugated to the chelator moiety of radiometals (B) via the spacer y and thereby forms part of e' of the spacer y. In other words, the at least one dye moiety (C) may include any additional atom(s) or linker(s) necessary or suitable to attach a dye moiety (C) to the rest of the compound, in particular to spacer y. For instance linking groups having alkylene (e.g., unbranched or branched $C_{1-10}$-alkylene), arylene (e.g., an $C_6$- or $C_{10}$-arylene (e.g., $C_6H_4$, or $C_{10}H_6$), combination of alkylene and arylene, or alkylene or arylene groups having heteroatoms (potentially forming functional groups such as, e.g., an amide group, an ester group, an amine, a carboxylic group, a carbonylic group, an isothiocyanate group, an isocyanate group, a maleimide group, an azide group, a succinimidyl group, a carbonate group, a carbamate group, etc.) may be optionally present in a dye moiety (C), so long as the linker does not interfere with the desired spectral properties of the dye moiety (C), in particular with the fluorescence of the dye moiety (C).

Therefore, a dye moiety (C) may be derived from the corresponding dye that may be conjugated to the rest of the compound, in particular to spacer y, by any means known in the art. The conjugation site between the rest of the compound, in particular to spacer y, and a dye moiety (C) may also comprise residuals of functional groups involved in such conjugation site which are derived from the precursor dye the dye moiety (C) is derived from. Preferably, such conjugation site is defined as e' as defined herein. Therefore, the conjugation site forms part of the spacer y and the dye moiety (C) derived from a dye of interest which has the structure of the dye without the functional group(s) involved in such binding, preferably forming part of e'.

Accordingly, in the context of a dye moiety, the term "derived from" a certain dye moiety means that the dye moiety results from the reaction of the free (unbound) dye by a functional group of said dye or a modification thereof. Typical modifications may be activated functional groups of the free dye, introduction of a functional group (e.g., directly or via a spacer) into the free dye or the linker. In the compound of the present invention, the residuals of such functional group may form part of the residue e' as defined herein.

A counterion as used herein may be any pharmaceutically acceptable ion that is suitable for neutralizing the charge of a residue or the compound of the present invention. It will be understood that a single counterion does not necessarily has the same valency as a charged residue or a charged compound of the present invention. Also two or more counterions may be used to neutralize a compound bearing a charge of higher charge valency than +1 or −1. Likewise, the other way round, also a single counterion bearing a charge of higher valency than +1 or −1 may be used to neutralize more than one compound. Preferably, the counterion is well-soluble in aqueous liquids.

A pharmaceutically acceptable negatively charged counterion $X^-$ in the context of the present invention may have any charge valency. Therefore, $X^-$ may exemplarily have a charge of −1, −2, −3 or −4, preferably of −1 or −2. Charge may also optionally depend on ion strength and pH, respectively. $X^-$ may be any pharmaceutically acceptable negatively charged ion. Preferably, the ion is such well-soluble in aqueous liquids. Exemplarily, $X^-$ may be selected from the group consisting of a halide anion (e.g., $F^-$ or $Cl^-$), acetate, phosphate, hydrogen phosphate, and a pharmaceutically acceptable carboxylate (e.g., a fatty acid carboxylate). Further, it will be understood that the counterion typically depends on the surrounding liquids such as those comprised in the buffer the compound is dissolved in and the body fluids after injection in vivo. In vivo, extracellularly, one of the main, but not sole negatively charged counterions is $Cl^-$.

"$C_{1-10}$ alkylene residue" means an alkylene chain having 1-10 carbon atoms when two moieties of a molecule are linked by the alkylene group. Preferably, but not necessarily, the $C_{1-10}$ alkylene residue in the context of residue f of the spacer y is a straight-chain, i.e., unbranched, $C_{1-10}$ alkylene residue, in which optionally one or more hydrogen(s) are substituted and/or in which optionally one or more —$CH_2$— moieties may be replaced by —O— or —NH—. Examples are shown above.

In a more preferred embodiment, the spacer y bears one of the following structures:

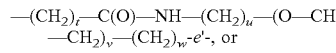
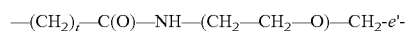

wherein t is 1 or 2, in particular 2;
wherein u is an integer from 1 to 10, preferably from 1 to 3, in particular 2;
wherein v is an integer from 0 to 3, in particular 2;
wherein w is an integer from 0 to 2, in particular 0;

In an even more preferred embodiment, the spacer y bears one of the following structures:

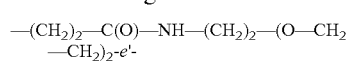

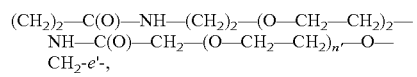

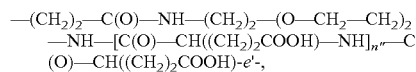

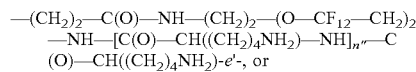

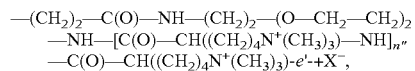

wherein n' is an integer from 1 to 3;
wherein n" is an integer from 0 to 2;
wherein $X^-$ is a pharmaceutically acceptable negatively charged counterion; and
wherein each e' is independently selected from the group consisting of a chemical bond, —NH—C(O)—, —C(O)—NH—, —C(O)—O— and —O—C(O)—, —NH—C(O)—NH—, —NH—C(S)—NH—, —C(O)—N(CH$_3$)—, —N(CH$_3$)—C(O)—, —NH—C(S)—, —C(S)—NH—,

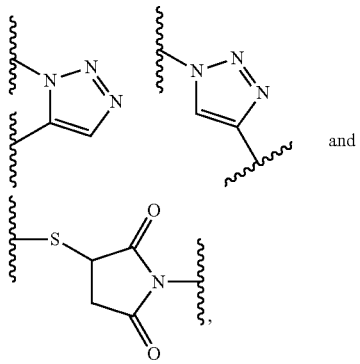

wherein one of the wavy lines indicates the conjugation site to f and the other wavy line indicates the conjugation site to the at least one dye moiety (C), in particular wherein e' is —NH—C(O)—.

The compound according to the present invention or a pharmaceutically acceptable salt thereof may preferably complex one or more radiometal(s) and may thereby form a compound-radiometal complex or, alternatively, may be non-complexed. Evidently, for detecting a radioactivity signal, said compound or salt thereof is preferably complexed with at least one radiometal, whereas, for detecting a fluorescence signal, it is optional whether said compound or salt thereof complexes a radiometal or not. Accordingly, in the context of detecting a radioactivity signal the term "compound" may be understood in a way that the compound preferably complexes at least one radiometal.

As mentioned above, the chelator moiety or radiometals (B) is preferably a chelator suitable to complex $^{68}$Ga, $^{99m}$Tc or $^{82}$Rb, in particular suitable to complex $^{68}$Ga in aqueous environment.

Gallium-68 ($^{68}$Ga) has a half-life of approximately 68 minutes and is thus rather inconvenient for longer transports. Therefore, it may typically be generated nearby the site where it is complexed with the compound of the present invention or a pharmaceutically acceptable salt thereof and administered to a patient in vivo and/or a sample in vitro.

Therefore, in a preferred embodiment, the chelator moiety of radiometals (B) is a $^{68}$Ga-chelator moiety, preferably a $^{68}$Ga-chelator moiety selected from the group consisting of:

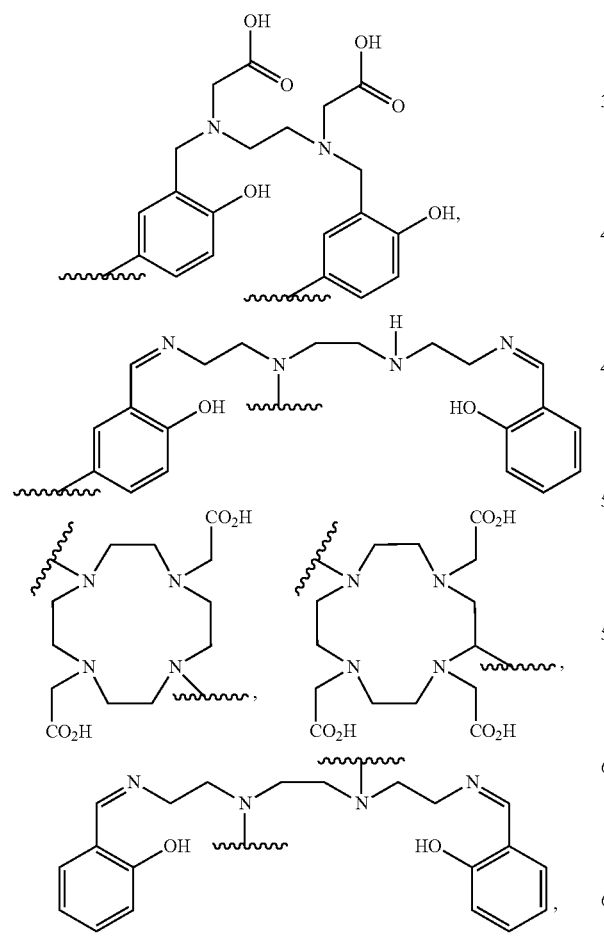

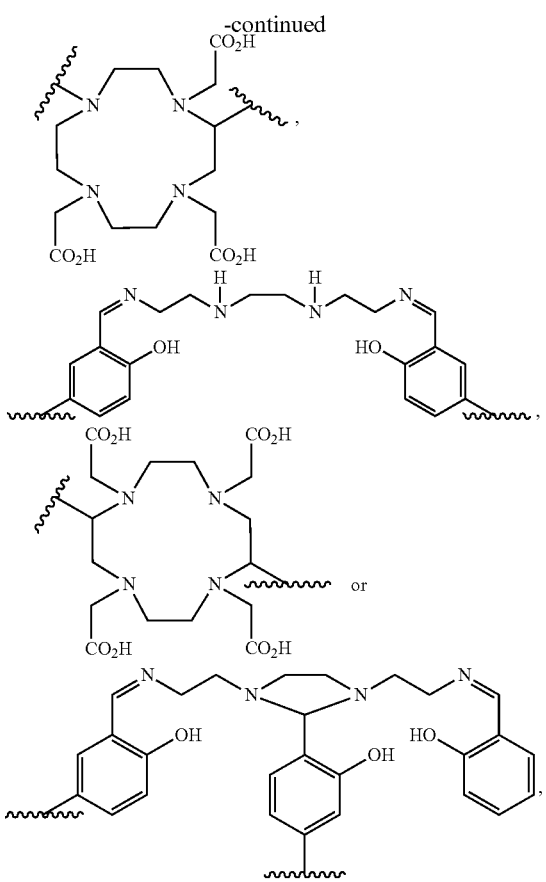

wherein in each of the structures one of the wavy lines indicates the conjugation site to the at least one motif specifically binding to cell membranes of neoplastic cells (A), preferably via a spacer x as defined herein, and the other wavy line indicates the conjugation site to the at least one dye moiety (C), preferably via the spacer y as defined herein, in particular wherein the $^{68}$Ga-chelator moiety is

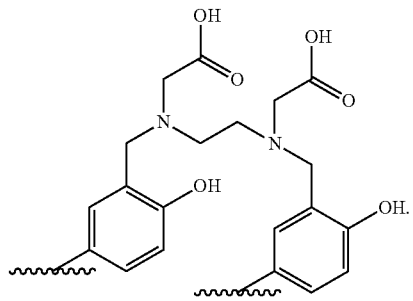 [SMILES: *c1ccc(O)c(CN(CCN(CC(=O)O)Cc2cc(*)ccc2O)CC(=O)O)c1]

When this chelator is used, b"" preferably is —C(O)—, $d^1$ and $d^2$ preferably are each —(CH$_2$)$_2$—, and e preferably is —C(O)—NH or —C(O)—O—. Therefore, the chelator moiety is conjugated with two —C(O)—(CH$_2$)$_2$-# moieties, wherein these are conjugated at the position indicated by "#" with the binding sites of the aforementioned chelator moiety indicated by the wavy lines. Then, this residue is also designated as HBED-CC.

It will be noted that several of these "$^{68}$Ga-chelator moieties" exemplarily listed above, may also serve as structures complexing one or more other radiometal(s) such as, e.g., $^{64}$Cu, in particular in aqueous environment of approximate neutral pH.

Preferably, neither the motif specifically binding to cell membranes of neoplastic cells (A) nor the complexed radiometal nor the chelator moiety of radiometals (B) quench the intensity of the fluorescence signal obtainable from the dye moiety (C) at its emission maximum in an aqueous environment of approximately neutral pH (i.e., pH 6-8, in particular 6.5-7.5) by more than 50%.

The dye moiety (C) may be any dye moiety known in the art. Preferably, it is suitable for emit light in an aqueous environment of approximately neutral pH, i.e., pH 6-8, in particular 6.5-7.5, in particular pH 7.0-7.5.

In a preferred embodiment, the dye moiety (C) is a fluorescent dye moiety having an emission maximum in the range from 400 nm to 1000 nm, in particular wherein said dye moiety is a moiety of a fluorescent dye selected from the group consisting of:
an indocyanine green (ICG) dye, in particular derived from sulfo indocyanine green (sulfo ICG);
a fluorescein-type dye, preferably derived from fluorescein isothiocyanate (FITC), carboxyfluorescein or fluorescein, in particular derived from FITC;
a rhodamine type dye, in particular derived from rhodamine G;
a cyanine dye, preferably derived from sulfoCy5, cyanine 5.5, Cy2, Cy3, Cy3.5, Cy5, Cy5.5, Cy7, Cy7.5, an AlexaFluor dye, DyLight, a FluoProbe dye, a sulfo Cy dye, or a seta dye, in particular derived from Cy5, Alexa488 or Alexa547;
an infrared dye, in particular derived from IRDye 800CW, IRDye 800RS, IRDye 800, IRDye 700, IRDye 700DX, IRDye 680 or IRDye 680LT;
a phenoxacin dye, in particular derived from Nile red or Nile blue
a dye moiety derived from an allophycocyanin dye;
a dye moiety derived from a berberin dye;
a dye moiety derived from quinine or a fluorescence quinine derivative;
a dye moiety derived from cumarine;
a dye moiety derived from 4',6-diamidino-2-phenylindole (DAPI);
a dye moiety derived from Epicocconone;
a dye moiety derived from 5-({2-[(iodoacetyl)amino]ethyl}amino)naphthalene-1-sulfonic acid (IAEDANS);
an Atto dye, preferably derived from ATTO 647, ATTO 488, ATTO 495, ATTO 520, ATTO 532, ATTO 550, ATTO 565, ATTO 590, ATTO 594, ATTO 610, ATTO 611X, ATTO 620, ATTO 633, ATTO 635, ATTO 637, ATTO 647N, ATTO 655, ATTO 665, ATTO 680, ATTO 700, ATTO 725, ATTO 740, ATTO 390, ATTO 425, ATTO 465, in particular ATTO 647 or ATTO 488;
a Visen dye, in particular derived from VivoTag680 or VivoTag750; and
a dye moiety derived from a HOECHST dye.

Further examples of rhodamine type dye moieties usable in the context of the present invention may be those derivable from the fluorophores shown by Kolmakov et al. (cf., Kolamkov et al., 2012; Kolmakov et al., 2014), such as e.g., KK114 or Abberior Star 635P shown therein.

It will be noted that these dye moiety (C) enlisted here indicate the molecular structures of the dye moieties (C) itself, i.e., without the functional group of its precursor that is conjugated to the chelator moiety of radiometals (B) via the spacer y and thereby forms part of e' of the spacer y.

In a more preferred embodiment, the dye moiety (C) is a fluorescent dye selected from the group consisting of:
an indocyanine green (ICG) dye, in particular sulfo indocyanine green (sulfo ICG), a fluorescein-type dye, in particular FITC, a cyanine dye, in particular sulfo Cy5 or cyanine 5.5, an Atto dye, in particular ATTO 647N, Alexa488, an infrared dye, in particular IRDye 800CW.

In a highly preferred embodiment, the dye moiety (C) is a fluorescent dye moiety selected from the group consisting of the following structures:

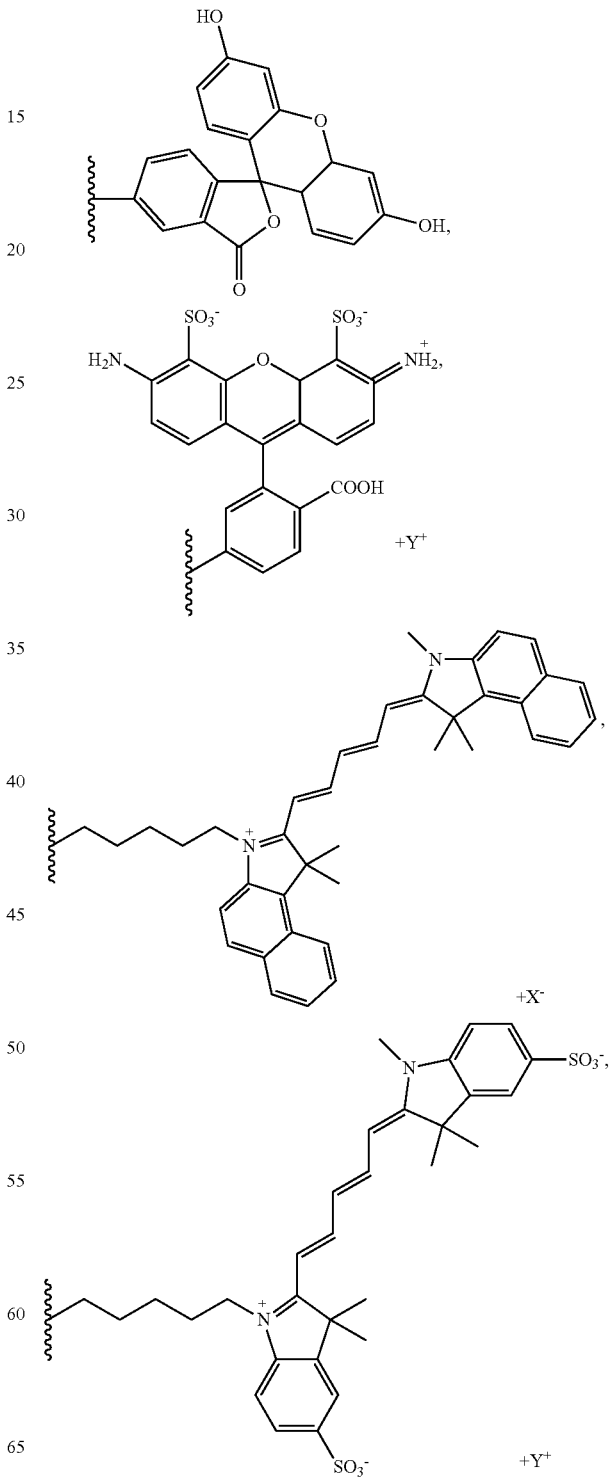

-continued

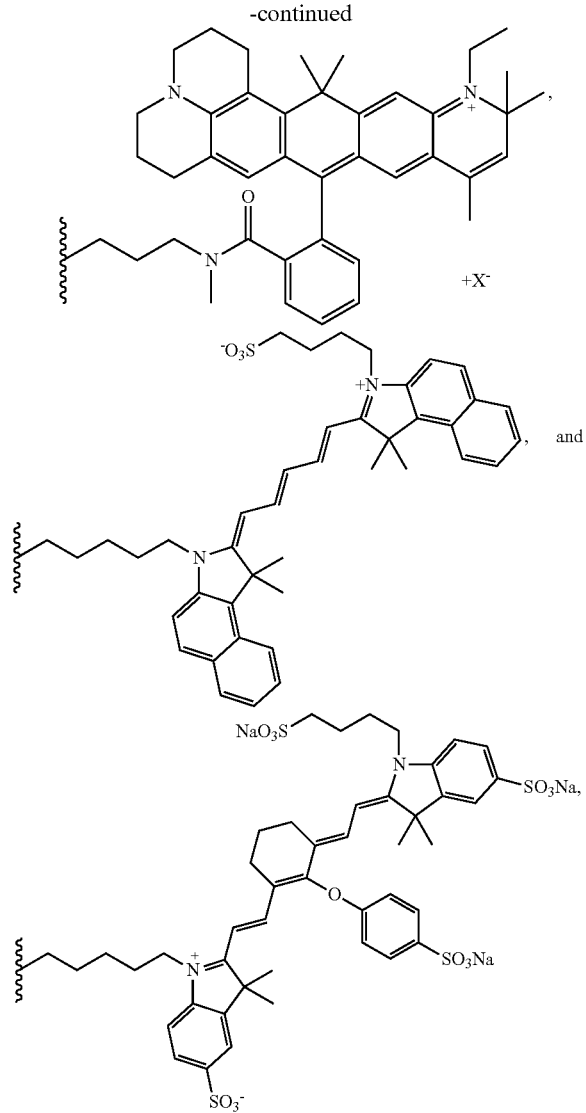

and wherein X⁻ is a pharmaceutically acceptable negatively charged counterion;
wherein Y⁺ is a pharmaceutically acceptable positively charged counterion; and
wherein the wavy line indicates the conjugation site to the rest of the compound of the present invention.

A pharmaceutically acceptable negatively charged counterion X⁻ may be understood in the broadest sense as laid out above.

Likewise, also a pharmaceutically acceptable positively charged counterion Y⁺ may have any valency. Therefore, Y⁺ may exemplarily have a charge of +1, +2, +3 or +4, preferably of +1 or +2. Y⁺ may be any pharmaceutically acceptable positively charged ion. Preferably, the ion is such well-soluble in aqueous liquids. Exemplarily, Y⁺ may be selected from the group consisting of a cation of an alkali metal (e.g., Na⁺, K⁺, Li⁺), a cation of an alkaline earth metal (e.g., Mg²⁺, Ca²⁺), Al³⁺, NH₄⁺, H⁺ and a cation of an organically bound amine. Further, it will be understood that the counterion typically depends on the surrounding liquids such as those comprised in the buffer the compound is dissolved in and the body fluids after injection in vivo. In vivo, extracellularly, one of the main, but not sole positively charged counterions is Na⁺.

Preferably, the wavy line indicates the conjugation site to the spacer y. More preferably, the wavy line indicates the conjugation site to e'.

As mentioned above, the compound may or may not comprise spacer molecule. Preferably, it comprises at least one spacer molecule. As used herein, a spacer is in the broadest sense any molecule enabling a larger distance between the components (A), (B) and (C) from another. As the spacer may preferably be a flexible spacer, it is apparent that molecular movement, in particular in an aqueous environment, may alter the distance of the residues (A), (B) and (C) to another. The length of the spacer however defines the maximal distance between said residues. Preferably, the spacer(s) may essentially not quench the fluorescence signal obtainable from the dye moiety (C) at its emission maximum in an aqueous environment of approximately neutral pH (i.e., pH 6-8, in particular 6.5-7.5). Therefore, the spacers are preferably free of aromatic moieties.

In a preferred embodiment, the compound has the following molecular structure:

(A)-(B)-spacer-(C), preferably has the following molecular structure:

(A)-spacer-(B)-spacer-(C), wherein:
(A) refers to a prostate-specific membrane antigen (PSMA) binding motif, in particular a PSMA binding motif comprising the structure motif

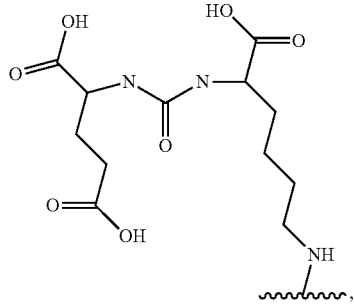

I wherein said motif is conjugated to (B) via the epsilon amino residue of the lysine moiety;
(B) refers to a chelator moiety of radiometals, preferably a ⁶⁸Ga-chelator moiety, in particular a ⁶⁸Ga-chelator moiety comprising the motif

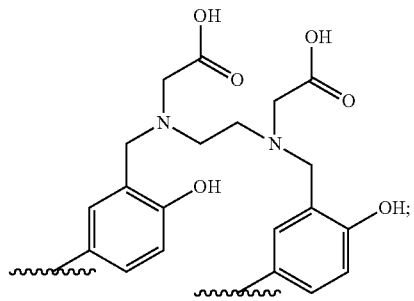 [SMILES: *c1ccc(O)c(CN(CCN(CC(=O)O)Cc2cc(*)ccc2O)CC(=O)O)c1]

(C) refers to a dye moiety having an emission maximum in the range from 400 nm to 1000 nm; and
the spacer comprises a molecular structure selected from the group consisting of polyethylene glycol (PEG), alkylene, peptidic or peptidomimetic spacer, preferably wherein the spacer has a length of from 0.5 to 10 nm, in particular wherein said spacer comprises a PEG spacer comprising not more than 2 to 10 consecutive PEG monomers.

Optionally, a PEG moiety may be substituted. Preferably, a PEG moiety may be unsubstituted. Then, exemplarily hydrogen may be substituted by a heteroatom or functional group. Exemplarily, a hydrogen atom may be substituted by —NH$_2$, —SH, —OH or by a halogen. Preferably, a PEG monomer may be an —O—CH$_2$—CHR$^a$— moiety, wherein R$^a$ may be H (then, the PEG moiety is an unsubstituted PEG moiety), or —NH$_2$, —SH or —OH (then, the PEG moiety is a substituted PEG moiety). Herein, PEG preferably comprises at least two —O—CH$_2$—CH$_2$— residues and not more than 10 —O—CH$_2$—CH$_2$— residues. An alkylene, in this context, is preferably a C$_{1-10}$-alkylene, a peptidic or peptidomimetic preferably comprises from one to ten amino acid moieties and/or analogues thereof.

"C$_{1-10}$-alkyl residue" means an alkyl chain having 1-10 carbon atoms, preferably a straight alkyl chain. Preferably, an C$_{1-10}$-alkyl residue is a straight-chain.

In a more preferred embodiment, the compound has the following molecular structure:

(A)-x-(B)-y-(C), wherein:
(A) refers to a prostate-specific membrane antigen (PSMA) binding motif, in particular a PSMA comprising the structure motif

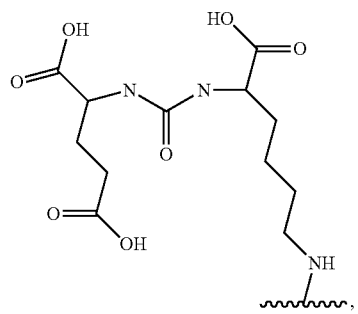

I wherein said motif is conjugated to (B) via the spacer x via the epsilon amino residue of the lysine moiety;
(B) refers to a chelator moiety of radiometals, preferably a $^{68}$Ga-chelator moiety, in particular a $^{68}$Ga-chelator moiety comprising the motif

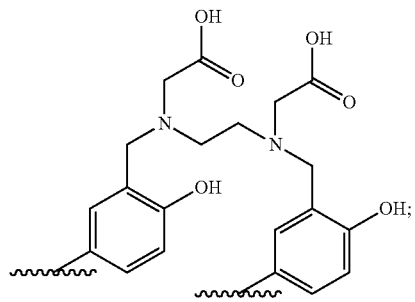 [SMILES: *c1ccc(O)c(CN(CCN(CC(=O)O)Cc2cc(*)ccc2O)CC(=O)O)c1]

(C) refers to a dye moiety having an emission maximum in the range from 400 nm to 1000 nm; and wherein the spacer y comprises a molecular structure selected from the group consisting of polyethylene glycol (PEG) of from two to 10 consecutive PEG moieties, a C$_{1-10}$-alkylene, a peptidic or peptidomimetic comprising from one to ten amino acid moieties and/or analogues thereof, and a combination of two or more thereof, preferably wherein the spacer has a length of from 0.5 to 10 nm, in particular wherein said spacer comprises a PEG spacer comprising 2 to 10 consecutive PEG monomers.

In a more preferred embodiment, the compound has the following molecular structure:

(A)-x-(B)-y-(C), wherein:
(A) refers to a prostate-specific membrane antigen (PSMA) binding motif, in particular a PSMA comprising the structure motif

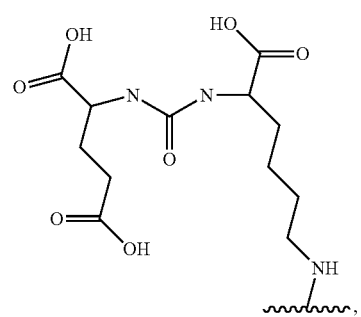

I wherein said motif is conjugated to (B) via the spacer x via the epsilon amino residue of the lysine moiety;
x represents the structure —[C(O)—(CH$_2$)$_5$—NH]$_n$—C(O)—(CH$_2$)$_2$—, wherein n is 0 or 1;
(B) refers to a chelator moiety of radiometals, preferably a $^{68}$Ga-chelator moiety, in particular a $^{68}$Ga-chelator moiety comprising the motif

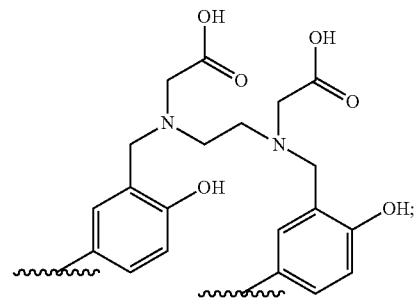 [SMILES: *c1ccc(O)c(CN(CCN(CC(=O)O)Cc2cc(*)ccc2O)CC(=O)O)c1]

y represents one of the following structures:

—(CH$_2$)$_t$—C(O)—NH—(CH$_2$)$_u$—(O—CH$_2$—CH$_2$)$_v$—(CH$_2$)$_w$-e'-, or

—(CH$_2$)$_t$—C(O)—NH—(CH$_2$—CH$_2$—O)$_v$—CH$_2$-e'- wherein t is 1 or 2, in particular 2;
wherein u is an integer from 1 to 10, preferably from 1 to 3, in particular 2;
wherein v is an integer from 0 to 3, in particular 2;
wherein w is an integer from 0 to 2, in particular 0,
in particular wherein y represents the structure:

—(CH$_2$)$_2$—C(O)—NH—(CH$_2$)$_2$—(O—CH$_2$—CH$_2$)$_2$-e'-; and (C) refers to a dye moiety having an emission maximum in the range from 400 nm to 1000 nm.

Accordingly, in a highly preferred embodiment, the compound has the following chemical structure:

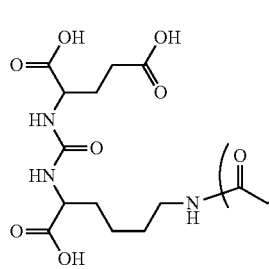
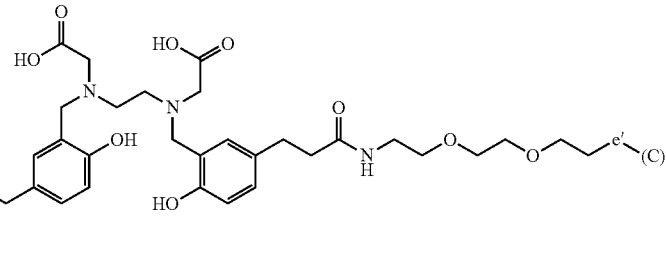

(C)

wherein n indicates 0 or 1;
wherein each e' is independently selected from the group consisting of a chemical bond, —NH—C(O)—, —C(O)—NH—, —C(O)—O— and —O—C(O)—, —NH—C(O)—NH—, —NH—C(S)—NH—, —C(O)—N(CH$_3$)—, —N(CH$_3$)—C(O)—, —NH—C(S)—, —C(S)—NH—,

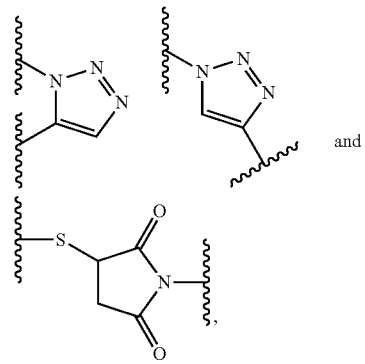

and wherein one of the wavy lines indicates the conjugation site to f and the other wavy line indicates the conjugation site to the at least one dye moiety (C), in particular wherein e' is —NH—C(O)—; and wherein (C) indicates the dye moiety (C), preferably having an emission maximum in the range from 400 nm to 1000 nm, in particular being a fluorescent dye selected from the group consisting of an indocyanine green (ICG) dye, in particular sulfo indocyanine green (sulfo ICG), a fluorescein-type dye, in particular FITC, a cyanine dye, in particular sulfoCy5 or cyanine 5.5, Alexa488, an Atto dye, in particular ATTO 647N, and an infrared dye, in particular IRDye 800CW.

In a particularly preferred embodiment, the compound has one of the following chemical structures:

PSMA-Ahx-HBED-CC-FITC:

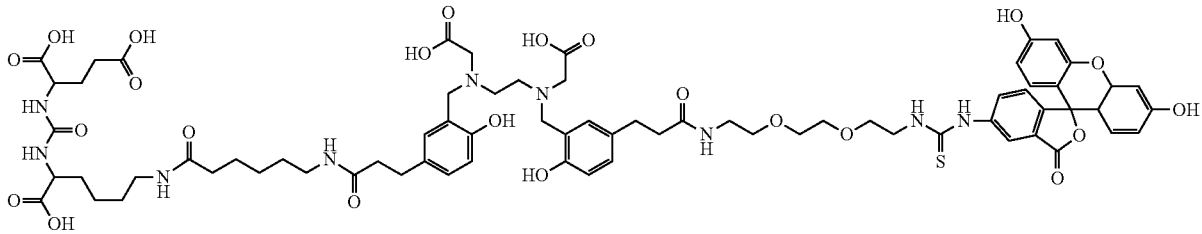 [SMILES: O=C(O)CCC(NC(=O)NC(CCCCNC(=O)CCCCCNC(=O)CCc1ccc(O)c(CN(CCN(CC(=O)O)Cc2cc(CCC(=O)NCCOCCOCCNC(=S)Nc3ccc4c(c3)C(=O)OC43c4ccc(O)cc4OC4C=C(O)C=CC43)ccc2O)CC(=O)O)c1)C(=O)O)C(=O)O]

PSMA-Ahx-HBED-CC-Alexa488:

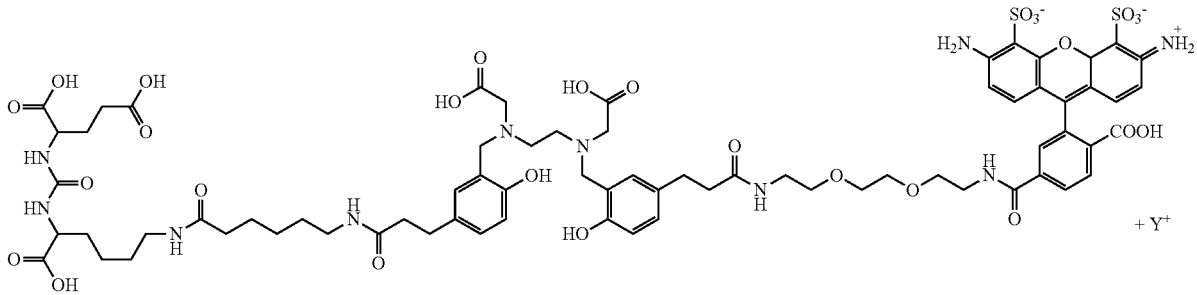

PSMA-Ahx-HBED-CC-cyanine 5.5:
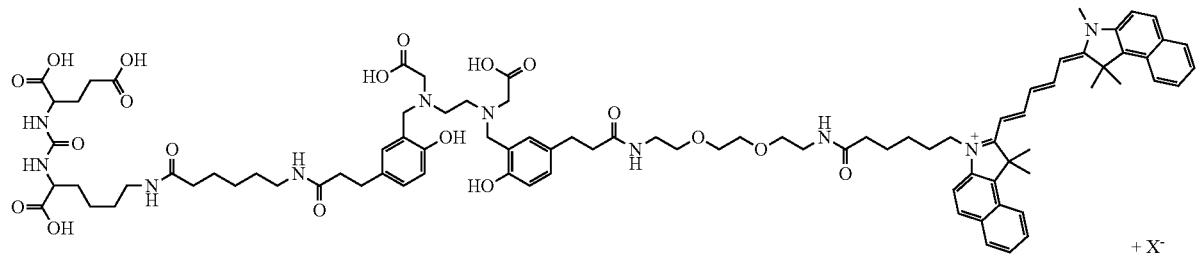
PSMA-Ahx-HBED-CC-sulfoCv5:
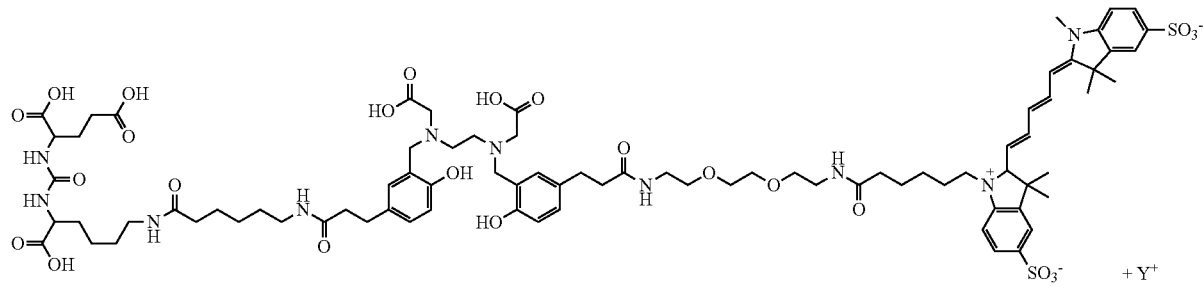
PSMA-Ahx-HBED-CC-ATTO647N:
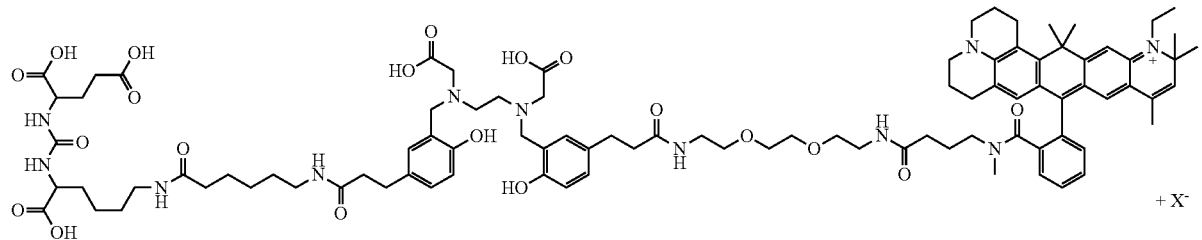
PSMA-Ahx-HBED-CC-ICG:
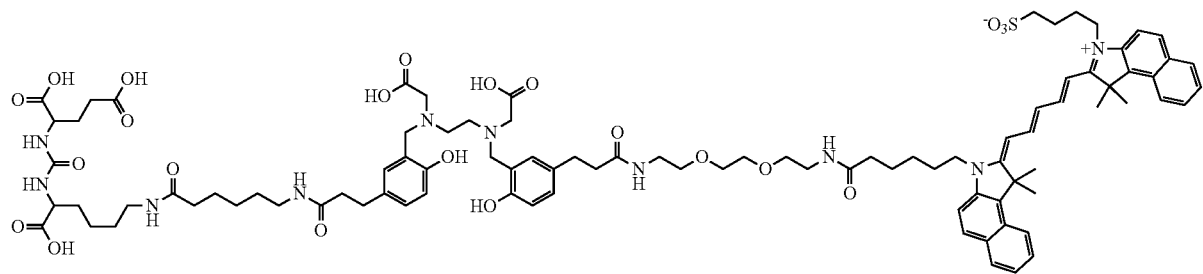

PSMA-Ahx-HEED-CC-IRdye800CW:

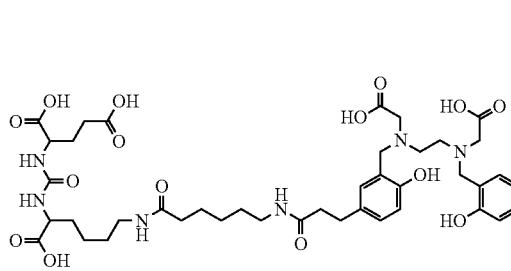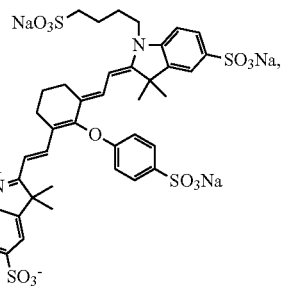

wherein X⁻ is a pharmaceutically acceptable negatively charged counterion; and
wherein Y⁺ is a pharmaceutically acceptable positively charged counterion.

A pharmaceutically acceptable negatively charged counterion X⁻ and a pharmaceutically acceptable positively charged counterion Y⁺ may be each understood in the broadest sense as laid out above.

In an alternative particularly preferred embodiment, the compound has the following chemical structure (PSMA-HBED-CC-FITC):

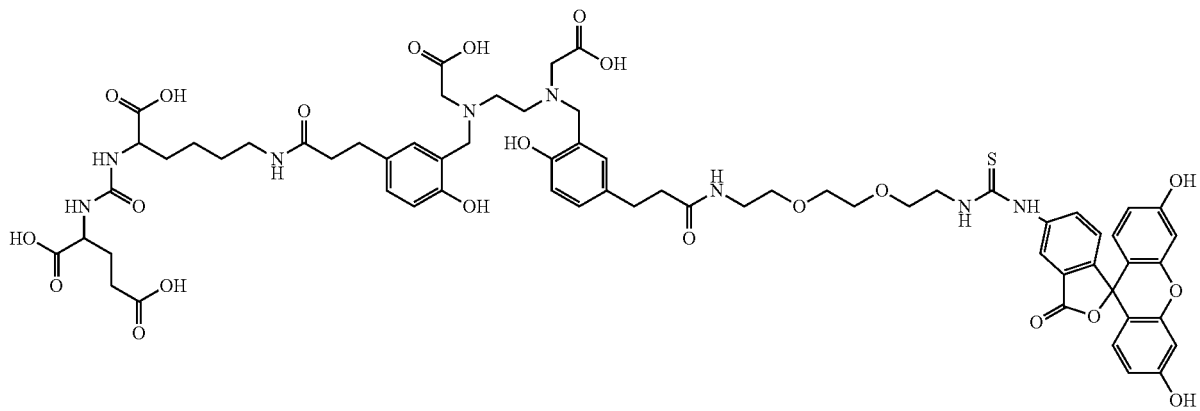 [SMILES: O=C(O)CCC(NC(=O)NC(CCCCNC(=O)CCc1ccc(O)c(CN(CCN(CC(=O)O)Cc2cc(CCC(=O)NCCOCCOCCNC(=S)Nc3ccc4c(c3)C(=O)OC43c4ccc(O)cc4Oc4cc(O)ccc43)ccc2O)CC(=O)O)c1)C(=O)O)C(=O)O]

Preferably, the amino acid moieties (i.e., the glutamate moiety and the lysine moiety) comprised in the motif specifically binding to cell membranes of neoplastic cells bear the L-configuration.

The compound according to the present invention may be obtained from rational chemical synthesis.

Accordingly, a further aspect of the present invention relates to a method for producing a compound or a pharmaceutically acceptable salt thereof comprising the following steps:
(i) providing at least one motif specifically binding to cell membranes of neoplastic cells (A), wherein all reactive moieties except one are protected;
(ii) reacting said at least one motif with at least one chelator moiety of radiometals (B);
(iii) reacting the compound obtained from step (ii) with any of:
   (a) at least one activated dye moiety (C),
   (b) at least one spacer-conjugated dye moiety (C) wherein the spacer is activated, or
   (c) at least one spacer molecule(s) which is/are subsequently reacted with at least one activated dye moiety (C);
(iv) deprotecting the compound obtained from step (iii); and
(v) isolating the compound or a pharmaceutically acceptable salt thereof obtained from step (iv).

More in particular, an aspect of the present invention relates to a method for producing a compound having the formula (A)-(B)-(C) or a pharmaceutically acceptable salt thereof,
wherein the "-" may be a bond via a spacer molecule or a direct bond, preferably a bond via a spacer molecule, wherein said compound has the molecular structure (A)-x-(B)-y-(C), wherein x and y are each independently from another a spacer molecule, comprising the following steps:
(i) providing at least one motif specifically binding to cell membranes of neoplastic cells (A), optionally conjugated with a spacer x or a part thereof, wherein all reactive moieties except one are protected;
(ii) reacting said at least one motif with at least one chelator moiety of radiometals (B) optionally conjugated with a spacer x or a part thereof and/or a spacer y or a part thereof;
(iii) reacting the compound obtained from step (ii) with any of:
   (a) at least one activated dye moiety (C),
   (b) at least one spacer-conjugated dye moiety (C) wherein the spacer is activated, or
   (c) at least one spacer molecule(s) y or parts thereof which is/are subsequently reacted with at least one activated dye moiety (C);

(iv) deprotecting the compound obtained from step (iii); and
(v) isolating the compound or a pharmaceutically acceptable salt thereof obtained from step (iv).

Herein, the definitions as laid out above may also apply, in particular the definitions of (A), (B), (C), x and y.

In a preferred embodiment, the motif specifically binding to cell membranes of neoplastic cells (A), the chelator moiety of radiometals (B), the dye moiety (C), the spacer x and/or the spacer y are defined as laid out above.

In a more preferred embodiment, the motif specifically binding to cell membranes of neoplastic cells (A), the chelator moiety of radiometals (B), the dye moiety (C), the spacer x and the spacer y are defined as laid out above Exemplarily, when the binding motif is a PSMA binding motif, the Glu-urea-Lys motif comprised therein may be obtained by performing an isocyanate reaction of protected Glu with resin immobilized lysine. The resulting product may then be reacted with a bi-activated TFP-ester of N,N-bis(2-hydroxybenzyl)ethylenediamine-N,N-diacetic acid (HBED-CC) and 2,2'(ethylenedioxy)bis(ethylamine) to form the precursor for dye conjugation. Then a reactive fluorescent dye such as, e.g., fluorescein isothiocyanate (FITC) may be conjugated. This is further exemplified in the examples.

The method may lead to any compound or any salt thereof comprising at least one motif specifically binding to cell membranes of neoplastic cells (A), at least one chelator moiety of radiometals (B) and at least one dye moiety (C).

In a preferred embodiment, the motif specifically binding to cell membranes of neoplastic cells (A), the chelator moiety of radiometals (B) and/or the dye moiety (C) are defined as above.

Compounds obtainable from the method are also embraced by the present invention.

Accordingly, a further aspect of the present invention relates to a compound or a pharmaceutically acceptable salt thereof obtainable from the method according to the present invention.

Preferably, the compound obtainable from the method comprises the motif specifically binding to cell membranes of neoplastic cells (A) and the chelator moiety of radiometals (B) and, optionally, the dye moiety (C) defined as above.

Alternatively or additionally, the compound obtainable from the method comprises the motif specifically binding to cell membranes of neoplastic cells (A) and, the dye moiety (C) and, optionally, the chelator moiety of radiometals (B) defined as above. Alternatively or additionally, the compound obtainable from the method comprises the dye moiety (C) and the chelator moiety of radiometals (B) and, optionally, the compound obtainable from the method comprises the motif specifically binding to cell membranes of neoplastic cells (A) defined as above.

Particularly preferably, the compound obtainable from the method comprises the motif specifically binding to cell membranes of neoplastic cells (A), the chelator moiety of radiometals (B) and the dye moiety (C) are defined as above.

The compound according to the present invention may be essentially pure or may form part of a composition further comprising a radiometal and one or more pharmaceutically acceptable carriers.

The present invention further relates to a composition comprising:
(a) the compound according to the present invention or a pharmaceutically acceptable salt thereof as defined above;
(b) a radiometal, in particular $^{68}$Ga; and optionally
(c) one or more pharmaceutically acceptable carriers.

A pharmaceutically acceptable carrier may be any agent that is pharmaceutically acceptable and addable to the compound complexed with the radiometal (compound-radiometal complex).

Exemplarily, a pharmaceutically acceptable carrier may comprise a solvent with no or low toxicity such as, e.g., water, an aqueous buffer (e.g., a Hepes, Tris, or phosphate buffer, a phosphate buffer), a pharmaceutically acceptable organic solvent (e.g., dimethyl sulfoxide (DMSO), ethanol, vegetable oil, paraffin oil) or a combination of two or more thereof.

Furthermore, the pharmaceutically acceptable carrier may contain one or more detergents, one or more foaming agents (e.g., sodium lauryl sulfate (SLS)/sodium docsyl sulfate (SDS)), one or more coloring agents (e.g., $TiO_2$, food coloring), one or more vitamins, one or more salts (e.g., sodium, potassium, calcium, zinc salts), one or more humectants (e.g., sorbitol, glycerol, mannitol, propylenglycol, polydextrose), one or more enzymes, one or more preserving agents (e.g., benzoic acid, methylparabene), one or more texturing agents (e.g., carboxymethyl cellulose (CMC), polyethylene glycol (PEG), sorbitol), one or more emulsifiers, one or more bulking agents, one or more glacing agents, one or more separating agents, one or more antioxidants, one or more herbal and plant extracts, one or more stabilizing agents, one or more polymers (e.g., hydroxypropyl methacrylamide (HPMA), polyethylene imine (PEI), carboxymethyl cellulose (CMC), polyethylene glycol (PEG)), one or more uptake mediators (e.g., polyethylene imine (PEI), dimethyl sulfoxide (DMSO), a cell-penetrating peptide (CPP), a protein transduction domain (PTD), an antimicrobial peptide, etc.) one or more antibodies, one or more sweeteners (e.g., acesulfame, an acesulfame salt (e.g., acesulfame potassium (acesulfame K), aspartame, cyclamate, saccharin, a saccharin salt (e.g., saccharin sodium (saccharin Na)), alitame, neotame, sucralose, dulcin, salt of aspartame-acesulfame, sorbitol, stevia, glycerol, inulin, mannitol, isomalt, maltitol, malto-oligosaccharide, lactitol, xylitol, glucin, neohesperidin dihydrochalcone, P-4000, brazzein, curculin, erythritol, glycyrrhizin, hydrogenated starch hydrolysates, luo han guo, mabinlin, miraculin, monatin, monellin, osladin, pentadin, tagatose, thaumatin), one or more counterstain dyes (e.g., fluorescein, fluorescein derivatives, Cy dyes, an Alexa Fluor dyes, rhodamine, quantum dots, etc.), one or more homeopathic ingredients one or more gustatory substances and/or one or more fragrances. The diagnostic composition will typically be formed by contacting the aforementioned component with another by any way known in the art. Preferably, the diagnostic composition is formed, thus, the above-referenced components are contacted with another prior to being administered to a patient.

The radiometal may be obtained commercially of, may be obtained from nature or may be obtained from a cyclotron. Preferably, the radiometal is obtained from a gallium-68 generator or a cyclotron, in particular from a gallium-68 generator or a cyclotron that is localized near the site where the composition according to the present invention is mixed and where optionally also the diagnosis in vivo and/or in vitro is performed. Particularly preferably, the radiometal $^{68}$Ga is obtained from a gallium-68 generator, thus, a device used to extract the positron-emitting isotope $^{68}$Ga of gallium from a source of decaying germanium-68. The parent isotope $^{68}$Ge is known to have a half-life of 271 days and may thus be shipped to the site where the gallium-68 generator is located.

Such composition may be used for diagnosing a patient for neoplasia, in particular cancerous tissue or tissue of risk of becoming cancerous, in a patient in vivo as well as in tissue culture in vitro.

Accordingly, a further aspect of the present invention relates to a method for diagnosing a neoplasm in a patient suffering therefrom or being at risk thereof, comprising administering sufficient amounts of the composition according to the present invention to said patient.

In the context of the diagnostic method, the definitions of the terms as specified in the context of the compound, the compound-radiometal complex or a pharmaceutically acceptable salt thereof above also apply.

As used in the context of the present invention, the term "patient" may be understood in the broadest sense as a subject or individual the compound or compound-radiometal complex of the present invention or pharmaceutically acceptable salt thereof is administered to, irrespective, whether it is a human or an animal and whether clinical symptoms occur or do not occur. Preferably, the patient is a mammalian including human, more preferably a human, a dog, a horse, a bovine, a pig, a mule, a donkey, a sheep, a goat, or a camel. Particularly preferably, the patient is a human patient.

A patient suffering from neoplasia may be understood in the broadest sense as any patient having a neoplasm. Herein, the patient suffering from neoplasia does not necessarily bear any clinical symptoms. The patient may be aware of a neoplasm or may not be aware of having a neoplasm. Likewise, the physician of the patient may be aware of the presence of a neoplasm or may not be aware thereof. The patient may optionally also suffer from pain, a feeling of pressure and/or gastrointestinal and/or urinal dysfunction.

The term "patient at risk thereof" may be understood in the broadest sense as any patient who could potentially develop a neoplasm. In particular, the patient may be at an age, may live at conditions, be exposed to a medicinal treatment influencing gene expression and/or may have a genetic heredity associated with an increased risk of developing a neoplasm. Exemplarily, the patient at risk may be older than 40 years, preferably older than 45 years, more preferably older than 50 years, even more preferably older than 60 years, even more preferably older than 70 years, in particular older than 80 years. Alternatively or additionally, the patient may be overweight. Alternatively or additionally, the patient may bear a family history, wherein cancer is comparably common, in particular wherein first-degree family members suffer from cancer.

The compound, compound-radiometal complex or a pharmaceutically acceptable salt thereof may be administered to the patient by any means. Preferably, it is injected into the tissue of interest (i.e., the neoplastic tissue or tissue being of risk of being neoplastic) or into a blood vessel via a syringe or a drip. Alternatively it may also be injected intraperitoneally or may be administered orally, nasally, respiratorically, topically or subcutaneously.

Exemplarily, the compound, compound-radiometal complex or pharmaceutically acceptable salt thereof may be injected intravenously (i.v.), intraperitoneally (i.p.), intraarterially (i.a.), intramusculary (i.m.) and/or subcutaneously (s.c.). Alternatively, the compound, compound-radiometal complex or pharmaceutically acceptable salt thereof may be taken up orally, e.g., as a powder, a tablet, a pill, a capsule, a chewable capsule, syrup, juice, gel, liquid or paste. Alternatively, the compound, compound-radiometal complex or pharmaceutically acceptable salt thereof may be taken up nasally (intra nasal) (e.g., as spray or aerosol), percutaneously (e.g., as cream, spray or ointment and/or via a coated plaster) and/or respiratorically (e.g., by inhalation of an aerosol or of a spray). It will be understood that the compound, compound-radiometal complex or pharmaceutically acceptable salt thereof may be administered locally or systemically.

Sufficient amounts of the compound, compound-radiometal complex or pharmaceutically acceptable salt thereof suitable for the treatment may depend on the physicochemical and pharmacological properties of said compound pharmaceutically acceptable salt thereof (e.g., the bioavailability, charge, lipophilicity, molecular weight etc.), the route of administration (e.g., including or excluding a first pass effect), the body mass of the patient, the metabolism of the patient (e.g., the rate of metabolism and excretion of the compound, compound-radiometal complex or pharmaceutically salt thereof) and the accuracy of the employed analytical apparatuses (i.e., analytical apparatuses of higher sensitivity may typically require lower amounts of compound, compound-radiometal complex or pharmaceutically salt thereof).

Neoplasia detectable by the composition of the present invention may be any neoplasia known in the art.

In a preferred embodiment, the neoplasia is cancer, in particular prostate cancer.

Prostate cancer as used herein may be understood in the broadest sense as any form of cancer that develops in the prostate, i.e., a gland in the male reproductive system. Preferably, prostate cancer is prostate carcinoma.

A patient of risk of developing prostate cancer may optionally have one or more risk factors selected from the group consisting of:
a conspicuous family history (e.g., having a first-degree relative (father or brother) suffers from prostate cancer);
a genetic background of risk (e.g., one or more mutations in BRCA1 and/or BRCA2 genes, one or more mutations in the hereditary Prostate cancer gene 1 (HPC1), one or more mutations in the androgen receptor, one or more mutations in the vitamin D receptor, a TMPRSS2-ETS gene family fusion (in particular TMPRSS2-ERG or TMPRSS2-ETV1/49), a loss of one or more cancer suppressor gene(s) (e.g., in the p53 gene, the PTEN (gene), KAI1, E-cadherin and/or CD44);
lower blood levels of vitamin D;
elevated blood levels of testosterone; and/or
occurrence of an infection or inflammation of the prostate (prostatitis) (e.g., infections with chlamydia, gonorrhea, Xenotropic MuLV-related virus (XMRV) HPV-16, HPV-18, HSV-2 and/or syphilis)

As already mentioned above, the diagnosis of the patient may include readout of the radioactive signal occurring from the complexed radiometal and/or the fluorescence signal occurring from the fluorescent dye. Both signals may enable the detection of the localizations and/or size of a neoplasm.

In a preferred embodiment, the method comprises at least the following steps:
(i) administering said composition to a patient;
(ii) detecting the radioactive signal of the radiometal,
preferably wherein step (ii) is conducted by three-dimensional imaging, particular comprising positron emission tomography (PET).

As used throughout the context of the present invention, the term "three-dimensional imaging" may be understood in the broadest sense as any method enabling to determine the localization of the complex of the compound-radiometal complex in a three-dimensional object. Such method may exemplarily be positron emission tomography (PET), magnetic resonance imaging (MRI), radiography (in particular computer tomography), single photon emission computed tomography (SPECT) or a combination of two or more thereof.

Highly preferably, the method includes positron emission tomography (PET).

PET may be understood in the broadest sense as a method based on the detection of pairs of gamma rays/photons emitted in opposite directions wherein the emission of said gamma rays/photons is caused by the nihilation event provoked by the liaison of an electron present in the patient's body or sample with a proton emitted upon disintegration of the radiometal. Three-dimensional images of tracer concentration within the body or sample may then be constructed by computer analysis. PET represents a nuclear medical imaging method that enables production of a three-dimensional image reconstruction and thus visualization of the shape, size and localization of neoplasia.

The person skilled in the art will know how to conduct such measurements and that PET may very well be combined with other imaging methods such as, e.g., three-dimensional fluorescent detection (e.g. via fluorescence molecular tomography (FMT)), CT and/or MRI. Such combinational detection may be performed concomitantly or subsequently and may be conducted by the same apparatus or different apparatuses.

A combination of two or more imaging methods may enable an overlay of the data obtained from such methods and, thereby, enables combining a high-resolution image (e.g., from MRI and/or CT) with a method enabling to depict aggregation of the compound-radiometal complex of the present invention in a certain area. Such results may enable a particularly precise determination of neoplastic tissue in a patient.

Before being administered to the patient, the composition of the present invention may typically be generated by admixing the compound-radiometal complex pharmaceutically acceptable salt thereof with the radiometal (forming a complex) and optionally a pharmaceutically acceptable carrier. Therefore, the method may optionally further include the preceding step of admixing the composition according to the present invention.

As mentioned above, a benefit of the compound, compound-radiometal complex or pharmaceutically salt thereof of the present invention is the ability to diagnose neoplasia in vivo and in vitro by means of detecting two different signals, i.e., (i) radioactive radiation resulting from the radiometal and (ii) fluorescence resulting from the dye moiety.

This enables, in one step, to determine the precise localization of a neoplasm in the whole patient's body or at least in a larger part thereof by means of detecting the radioactive signal, in particular be means of PET imaging. In a further step, the fluorescence may be detected. This may likewise be performed in the whole patient's body or at least in a larger part thereof, but may also be performed when the patient's body is opened, i.e., when the tissue of interest is laid open during a surgery.

Accordingly, in a further preferred embodiment, the method further comprises:

(iii) detecting the dye moiety (C), preferably comprising molecular imaging.

It will, however, be noted that alternatively optionally also either the one or the other detection method may be used, i.e., only the radioactivity signal from the radiometal or only the fluorescence signal from the dye moiety may be detected. Detecting the fluorescence signal only may allow the omittance of the radiometal what may make handling easier and decrease costs, but may, typically, reduce detection flexibility and data accuracy.

Throughout the present invention, the term "molecular imaging" in the context of detecting the dye moiety be understood in the broadest sense as any method enabling the localization of the dye moiety and, thus, the compound (or its radiometal complex) according to the present invention in an object of interest. Molecular imaging in this context may also be designated as "Fluorescence Molecular Imaging", abbreviated "FMI". As used in the in the context of detecting the dye moiety, detecting may be performed visually or in an apparatus-assisted manner.

Preferably, molecular imaging refers to detecting fluorescence in a patient's body or in a cell culture in a resolution (i.e., the nearest proximity of objects still distinguishable from another) enabling to detect localization of the compound in the object of interest. Accordingly, in a patient's body, the nearest proximity of objects still distinguishable from another by molecular imaging may preferably be lower than 1 cm, more preferably lower than 5 mm, in particular lower than 2 mm. In cell culture, the nearest proximity of objects still distinguishable from another by molecular imaging may preferably lower than 2 mm, more preferably lower than 1 mm, in particular lower than 0.5 mm or even in the microscopic range, i.e., lower than 0.1 mm. When performed in a patient's body, molecular imaging may exemplarily be fluorescence molecular tomography (FMT), Optical Imaging or Two-Photon Fluorescence Detection. When performed in cell culture, molecular imaging may exemplarily be fluorescence microscopy, confocal microscopy (e.g., Laser Scanning Microscopy (LSM)), two-photon fluorescence microscopy, Fluorescence Energy Transfer (FRET) based methods, fluorescence correlation spectroscopy (FCS) or fluorescence cross-correlation spectroscopy (FCCS). The imaging may optionally be further combined with other imaging methods such as, e.g., Positron Emission Tomography (PET), Magnetic Resonance Imaging (MRI), radiography (e.g., computer tomography) or Ultrasound Tomography (UT).

The step (iii) of detecting the dye moiety (C), preferably comprising molecular imaging may be conducted subsequent to step (ii) of detecting the radioactive signal of the radiometal, simultaneously to step (ii) or before step (ii).

In a preferred embodiment, step (iii) is conducted subsequent to step (ii).

Before detecting the dye moiety, the artisan may either administer the compound or compound-radiometal complex of the present invention or a pharmaceutically acceptable salt thereof to the patient a further time or may use the fluorescence signal obtainable from said compound, compound-radiometal complex or salt thereof administered once before the preceding detecting of radioactivity signal, such as in particular PET scan.

Both strategies may have some particular advantages. Administering said compound, compound-radiometal complex or salt thereof before the detection of the fluorescence signal a further time, enables to optimize its concentration range in order to obtain a qualitatively good fluorescence signal. Further, a local administration to the neoplastic tissue and its surrounding tissue laid open may be enabled. Such further administration may preferably be administration of the compound, compound-radiometal complex or salt thereof without the radiometal.

On the other hand, administration of said compound, compound-radiometal complex or salt thereof before the detection of the radioactivity signal only, in particular when it is administration only once, prevents the patient of being treated too often and may improve patient's compliance. Further, lower doses of said compound, compound-radiometal complex or salt thereof may prevent undesired possible side-effects thereof. In this case it may be beneficial when the half-live of the radiometal is not too long because then, when the surgical interaction takes place subsequent to the previous molecular imaging via detecting the radioactivity signal, the radioactivity of the radiometal may have been faded to a low and, thus, harmless level, when the surgical interaction actually takes place.

The artisan removing the neoplastic tissue, typically a surgeon, may optionally emit light exciting by the dye moiety during surgery and thereby visualize the neoplastic tissue that is to be removed. This may be performed in intervals or may be performed continuously. Excitation light may result from a standard lamp, from an operational lamp and/or from a headlamp worn by the surgeon and/or any other present person(s). The wavelength of the light may be either such efficiently exciting the dye moiety, in particular a wavelength near the excitation maximum, or the double of said wavelength efficiently exciting the dye moiety (for double-photon excitation), in particular the double of wavelength near the excitation maximum. In a highly preferred embodiment, step (iii) is conducted during surgery, wherein the cancerous tissue is at least partly laid open.

As mentioned before, the method of diagnosing the patient in vivo bases on the use of the composition according to the present invention, thus, on the compound, compound-radiometal complex or pharmaceutically acceptable salt thereof that has complexed the respective radiometal and optionally further comprises a pharmaceutically acceptable carrier. This represents the first and, likewise a specific medical use thereof.

Therefore, in one further aspect, the invention relates to the composition according to the present invention as specified above for use as a medicament, in particular for use as a diagnostic.

In second further aspect, the invention relates to the composition according to the present invention as specified above for use in a method for diagnosing a neoplasm in a patient suffering therefrom or being at risk thereof.

In the context of the composition for use, the definitions of the terms as specified in the context of the compound, compound-radiometal complex or pharmaceutically acceptable salt thereof above and the diagnostic method above also apply.

As mentioned above, in a preferred embodiment, the neoplasia is cancer, in particular prostate cancer.

In a preferred embodiment, the method comprises the following steps:
(i) administering said composition to a patient;
(ii) detecting the radioactive signal of the radiometal, in particular $^{68}$Ga,
preferably wherein step (ii) is conducted by three-dimensional imaging, in particular by means of positron emission tomography (PET).

As mentioned above, in a preferred embodiment, the method further comprises:
(iii) detecting the dye moiety (C), preferably by means of molecular imaging,
in particular wherein said step (iii) is conducted subsequent to step (ii).

As mentioned above, the compound or compound-radiometal complex according to the present invention or a pharmaceutically acceptable salt thereof may also be used for detecting a neoplasm in vitro, such as in cell culture or in cells obtained from a patient. In this context, the user of compound, compound-radiometal complex according to the present invention or a pharmaceutically acceptable salt thereof may be also be supplied with said compound or salt thereof in the form of a kit.

Accordingly, a further aspect of the present invention relates to a kit comprising:
(a) the compound according to the present invention or a pharmaceutically acceptable salt thereof as specified above or the composition according to the present invention as specified above; and
(b) a user manual.

In the context of the kit, the definitions of the terms as specified in the context of the compound or pharmaceutically acceptable salt thereof above, the diagnostic method and the composition for use as recited above also apply.

In the context of the present invention, the term "kit" may be understood in the broadest sense as a composition of different products that may be used for performing detecting a neoplasm. The kit may comprise, but may not be limited to the compound or composition according to the present invention or a pharmaceutically acceptable salt thereof, one or more pharmaceutically acceptable carriers, a user manual, syringes, needles, etc. Optionally, the compound according to the present invention or a pharmaceutically acceptable salt thereof or the composition according to the present invention may be dissolved, may be dried or may be freeze-dried. Preferably, the kit of the invention includes a freeze-dried labeled form of the compound or composition according to the present invention or a pharmaceutically acceptable salt thereof, a buffer to dissolve it, an injection or infusion device to mix the compound according to the present invention or a pharmaceutically acceptable salt thereof with the buffer and to administer the mixture to a patient.

The user manual may include instructions on how to store the compound or composition according to the present invention or a pharmaceutically acceptable salt thereof (e.g., temperature, humidity, shelf live etc.), which radiometals to use and, optionally, were to obtain them from, how to complex the compound according to the present invention or a pharmaceutically acceptable salt thereof with the respective radiometal (e.g., buffer conditions) and/or how to use the compound or composition according to the present invention or a pharmaceutically acceptable salt thereof for detecting a neoplasm in vivo and/or in vitro, (e.g., suggested amounts/concentrations, recommended detection techniques etc.).

When the radioactive half-life of the radiometal is sufficiently long enough, the kit may also comprise one or more radiometal(s) suitable to be complexed by the compound of the present invention.

The kit may also be used for and in vitro-detection and investigation of neoplasia.

Accordingly, a still further aspect of the present invention relates to a method for detecting neoplastic cells in a sample in vitro, comprising the following steps:
(i) providing cells which are neoplastic or at risk of being neoplastic, in particular cancerous or at risk of being cancerous;
(ii) administering the compound according to the present invention or a pharmaceutically acceptable salt thereof as specified above or the composition according to the present invention as specified above to said cells;
(iii) detecting the fluorescence and/or radioactive signal of said cells.

In the context of the present in vitro method, the definitions of the terms as specified in the context of the compound or pharmaceutically acceptable salt thereof above, the diagnostic method, the composition for use and the kit as recited above also apply.

The cells which are neoplastic or at risk of being neoplastic may be isolated, i.e., singularized cells or may be cells still present in their physiological context, i.e., in their tissue, which may also comprise different cell types. The cells may be obtained as a tissue sample from a patient who is suffering from a neoplasm or who is at risk of developing neoplasia or may be obtained from a tissue culture. The in vitro sample as used in the context of the present invention may also be a part of or even a whole dead body of a patient or a laboratory animal (e.g., mouse, rat, rabbit etc.).

When cultured the cells may be cultured at suitable conditions, i.e., typically at around 37° C., at a pH of approximately pH 6.5 to 7.5, in particular pH 7.0 to 7.5, with suitable nutrients, vitamins, minerals and, optionally, growth factors. The person skilled in the art will be able to choose a suitable standard cell culture technique suitable for the cells of interest.

Optionally, the cells may be vital during conducting the entire in vitro method. Alternatively, before the step (ii) of administering the compound according to the present invention or a pharmaceutically acceptable salt thereof or the composition according to the present invention to the cells or before step (iii) detecting the fluorescence and/or radioactive signal of said cells, the cells may also be fixed (e.g., is ethanol, acetone, or another fixing agent).

The cells may optionally also be counterstained by other dyes (e.g., DAPI or HOECHT dye for staining the nucleus, and/or a labeled antibody for staining another structure of interest).

In the present in vitro method, the compound or composition according to the present invention or a pharmaceutically acceptable salt thereof may be administered to the cells by preparing a buffer comprising said compound, composition or salt thereof and adding it to the cells. Alternatively, the compound according to the present invention or a pharmaceutically acceptable salt thereof or the composition may also be administered to a patient in vivo and, subsequent a cell and/or tissue sample may be withdrawn from said patient and investigated in vitro.

The present in vitro method particularly enables the consecutive and simultaneous detection of the radioactivity signal from the radiometal and the fluorescence signal from the dye moiety. It will, however, be noted that alternatively optionally also either the one or the other detection method may be used, i.e., only the radioactivity signal from the radiometal or only the fluorescence signal from the dye moiety may be detected. Detecting the fluorescence signal only may allow the omittance of the radiometal what may make handling easier and decrease costs, but may, typically, reduce detection flexibility and data accuracy.

Depending on the employed detection method, before conducting step (iii), the cells may optionally be washed with fresh buffer or cell culture medium in order to remove the excess of unbound compound or compound-radiometal complex.

According to the present invention, neoplastic cells will typically show higher staining rates than corresponding non-neoplastic cells of the same cell type.

The cells may preferably be obtained from a patient, in particular a human.

In a preferred embodiment, the cells are obtained from a patient suffering from or being at risk of a neoplasm preferably cancer, in particular prostate cancer.

Detection may be performed by any means known in the art.

In a preferred embodiment, step (iii) includes detecting fluorescence via microscopic imaging, in particular confocal laser scanning microscopy (LSM) or two-photon microscopy.

Herein, confocal laser scanning microscopy (LSM) or two-photon microscopy may enable the detection of the compound or compound-radiometal complex according to the present invention or a pharmaceutically acceptable salt thereof at the cell surface of cells at the microscopic level. Therefore, comparably small local increases at certain membrane sites may be detectable.

In another preferred embodiment, step (iii) includes detecting fluorescence via a flow cytometer and or fluorescence activated cell sorting (FACS).

Detection via a flow cytometer may enable quantifying the fraction of neoplastic cells versus the fraction of non-neoplastic cells in a sample. Fluorescence activated cell sorting (FACS) may further enable isolating a cell population of interest, such as, e.g., the fraction of neoplastic cells, the fraction of a certain cell type (optionally identified by counterstaining with an antibody typical for a membrane protein of said cells) or the fraction of neoplastic cells of a certain cell type.

In a preferred embodiment, step (iii) includes detecting radioactivity by gamma counting.

As used in the context of the present invention, the term "gamma counting" may be understood in the broadest sense as any method based on the quantification of gamma irradiation. The person skilled in the art will know several methods based on gamma counting and how to conduct these. Exemplarily, gamma counting may be used in the context of a radio-binding assay and/or in a radio-immuno assay (RIA). The readout may be performed by direct gamma counting or by indirect gamma counting such as scintillation counting, in particular liquid scintillation counting. Gamma counting may enable quantifying the fraction of a certain cell type. Further, when combined with a preceding step of isolating a certain cell fraction, e.g., by means of FACS (cf. above), gamma counting may also provide information on the fraction of a specific cells population of interest.

As mentioned above, detecting the fluorescence and detecting radioactive signal (in particular the gamma irradiation) of said cells may be combined with another. Alternatively, only the fluorescence may be detected or only the radioactive signal may be detected.

In any case, when analyzing the data, the cells showing different intensities of fluorescence and/or radioactive signal may be grouped into different fractions. This is typically performed by setting a certain threshold. As mentioned above, according to the present invention, neoplastic cells will typically show higher staining rates, and thus a higher signal intensity compared to corresponding non-neoplastic cells of the same cell type.

Accordingly, in a preferred embodiment, the method further comprises the steps of:
(iv) determining:
  (a) the number of cells above a fluorescence and/or radioactive signal indicating a neoplastic cell, in particular a cancerous cell, and
  (b) the number of cells blow a fluorescence and/or radioactive signal indicating a non-neoplastic cell; and (v) determining the ratio of (a):(b) and assessing the severity of the neoplastia of the patient the cells have been obtained from.

The number of cells above a fluorescence and/or radioactive signal indicating a neoplastic cell, thus, above a given threshold, show a higher signal intensity compared to corresponding non-neoplastic cells of the same cell type. The person skilled in the art will notice that the signal intensity representing the threshold depends on the investigated cells and the detection method. It may be determined by measuring:

(a) the signal obtained from cells which are known to be neoplastic; and
(b) the signal obtained from corresponding cells which are known to be healthy, i.e., non-neoplastic.

Herein, (a) will typically provide a higher measured intensity than (b). The threshold may be set in between the two measured intensities for (a) and (b).

This may enable to determine assessing the severity of a neoplasm in a patient. A high fraction of cells determined to be neoplastic cells may indicate a severe neoplasia. Therefore, a comparably high fraction of the cells of the investigated tissue are neoplastic, thus, the neoplasm is comparably widespread. In contrast, a low fraction may indicate a less severe neoplasia and the absence of neoplastic cells may indicated the absence of a neoplasm in the investigated tissue sample.

Accordingly, the compound or compound-radiometal complex according to the present invention or a pharmaceutically acceptable salt thereof may also be used for assessing the severity of a neoplasm in a sample in vitro.

Therefore, in a yet further aspect, the present invention relates to the use of the compound according to the present invention or a pharmaceutically acceptable salt thereof as specified above or the composition according to the present invention as specified above for assessing the severity of a neoplasm in a sample in vitro, wherein said sample comprises cells which are neoplastic or at risk of being neoplastic, in particular cancerous or at risk of being cancerous, and which are contacted with said compound or a pharmaceutically acceptable salt thereof or said composition.

In the context of this use, the definitions of the terms as specified throughout the invention above also apply.

In a preferred embodiment, the assessing of the severity of a neoplasm includes determining the ratio of
(a) the number of cells above a fluorescence and/or radioactive signal indicating a neoplastic cell, in particular a cancerous cell, and
(b) the number of cells blow a fluorescence and/or radioactive signal indicating a non-cancerous cell.

The following figures and example are intended to illustrate the invention but not to limit the scope of protection conferred by the claims.

FIGURES

Figure 1B:
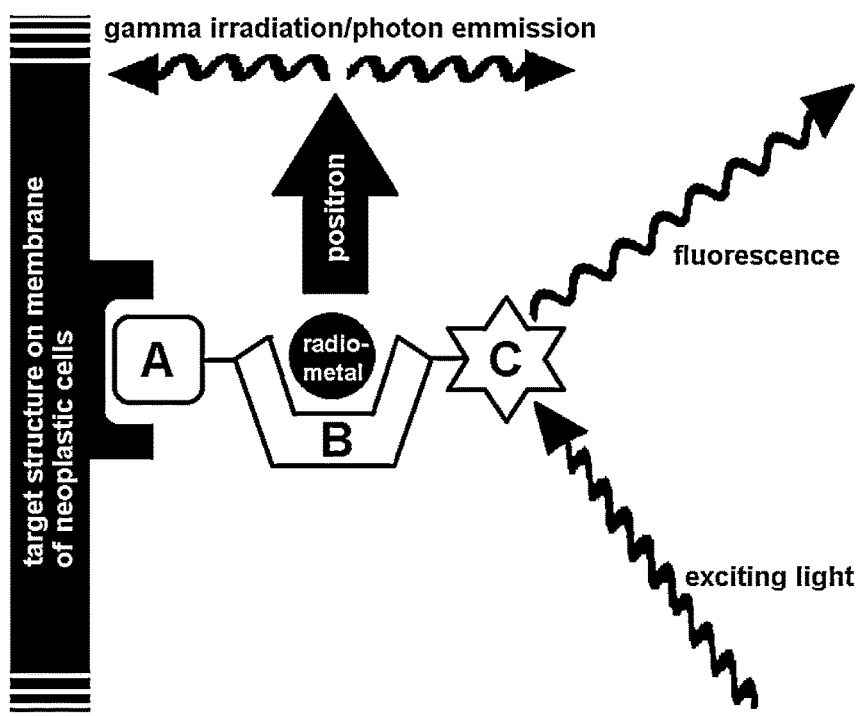

FIG. 1 depicts the basic principle of the compound according to the present invention. FIG. 1A shows the compound in its non-complexed form. The motif specifically binding to cell membranes of neoplastic cells (A) enables binding to the cellular target structure on neoplastic surfaces (black on the left-hand side) and the dye moiety (C) emits fluorescent light upon excitation. FIG. 1B shows the compound complexing a radiometal. Here, additionally, positrons are emitted upon disintegration of the radiometal. When these hit on an electron in the sample, photons are emitted in two traverse directions, which can be detected.

Figure 2A:
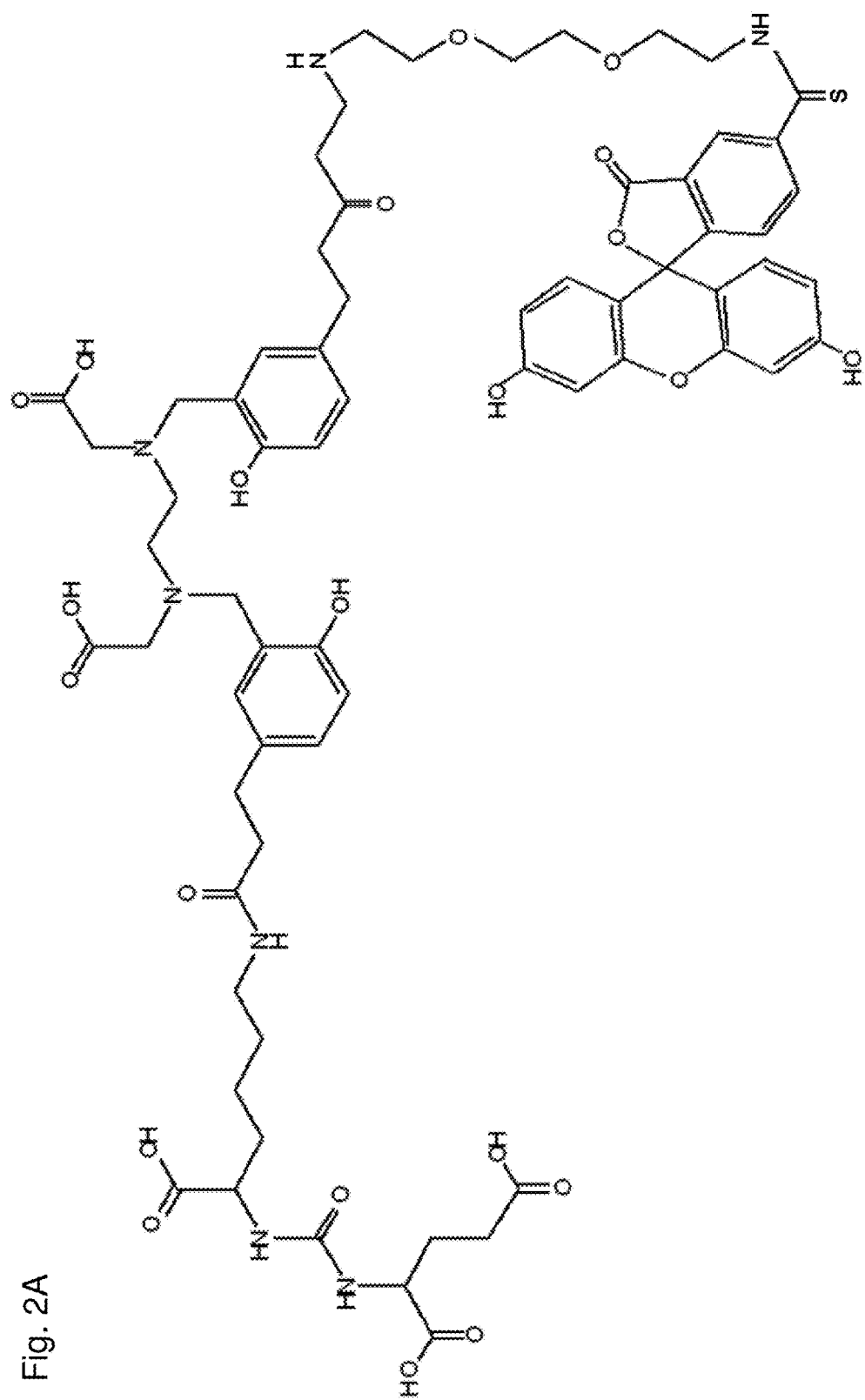
Figure 2B:
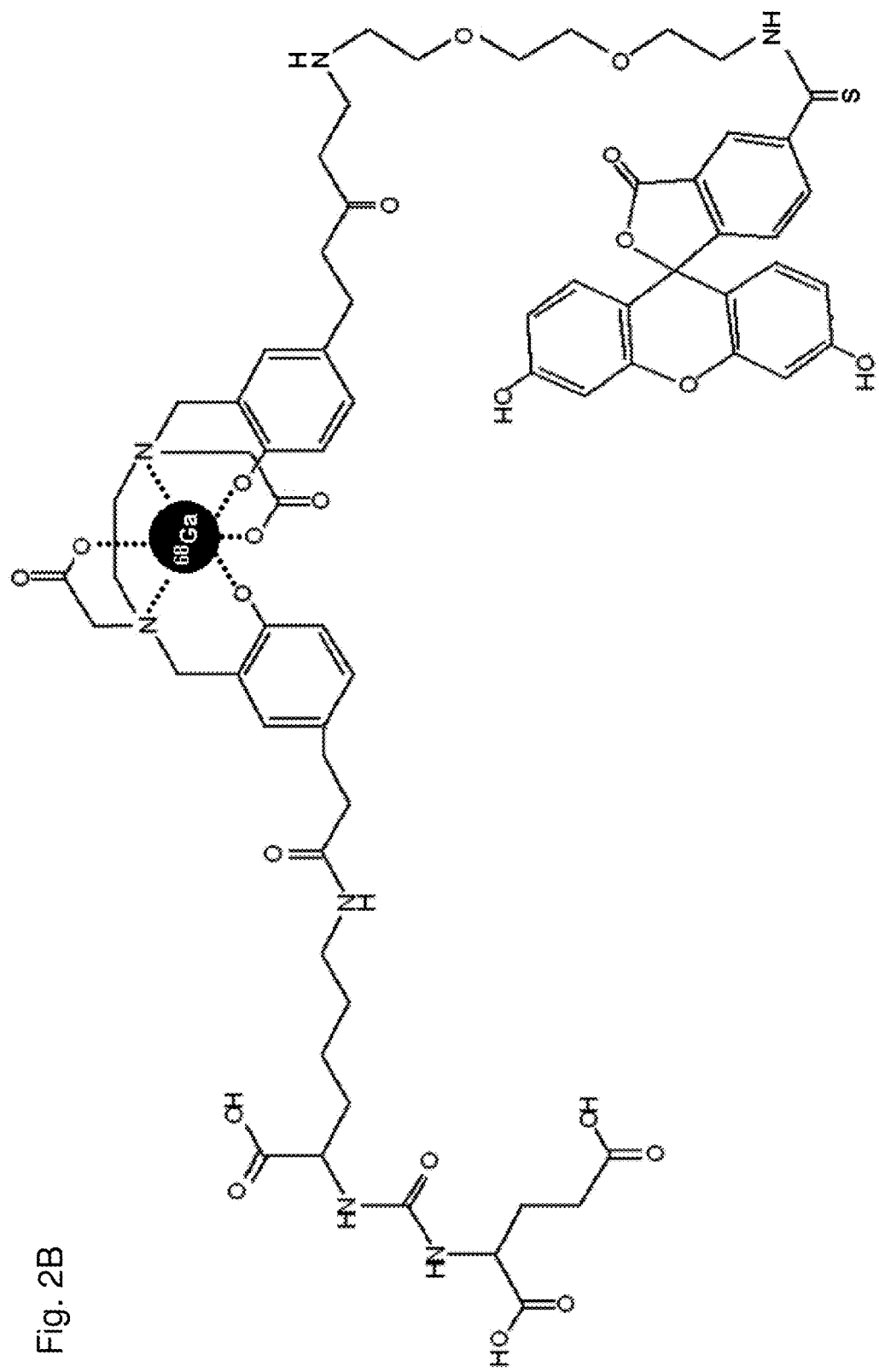

FIG. 2 exemplarily shows a compound according to the present invention. FIG. 2A shows the compound in its non-complexed form. FIG. 2B shows the compound complexing the radiometal $^{68}Ga$. The amino acid moieties (i.e., the glutamate moiety and the lysine moiety) preferably bear the L-configuration.

Figure 3:
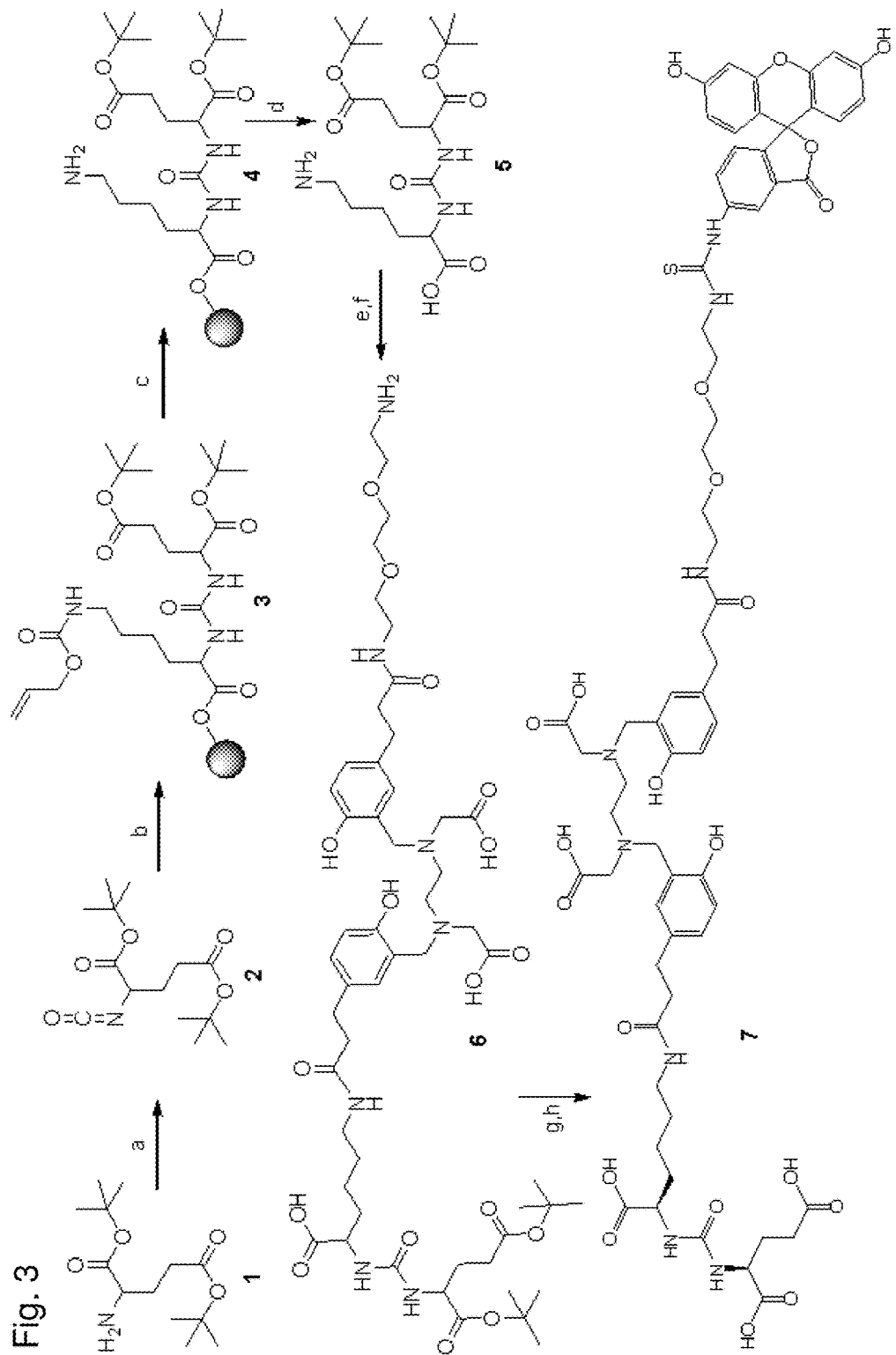

FIG. 3 exemplifies the synthesis of Glu-urea-Lys-HBED-CC-PEG$_2$-fluorescein. Herein, a indicates triphosgene, DIPEA, CH$_2$Cl$_2$, 0° C.; b indicates H-Lys(Alloc)-2CT-Resin, CH$_2$Cl$_2$; c indicates Pd[P(C$_6$H$_5$)$_3$]$_4$, morpholine, CH$_2$Cl$_2$; d indicates hexafluoroisopropanol/CH$_2$Cl$_2$; e indicates (HBED-CC)TFP$_2$, DIPEA, DMF; f indicates 1,8-Diamino-3,6-Dioxaoctane; g indicates fluorescein isothiocyanate (isomer I), DIPEA, DMF; and h indicates TFA.

Figure 4:
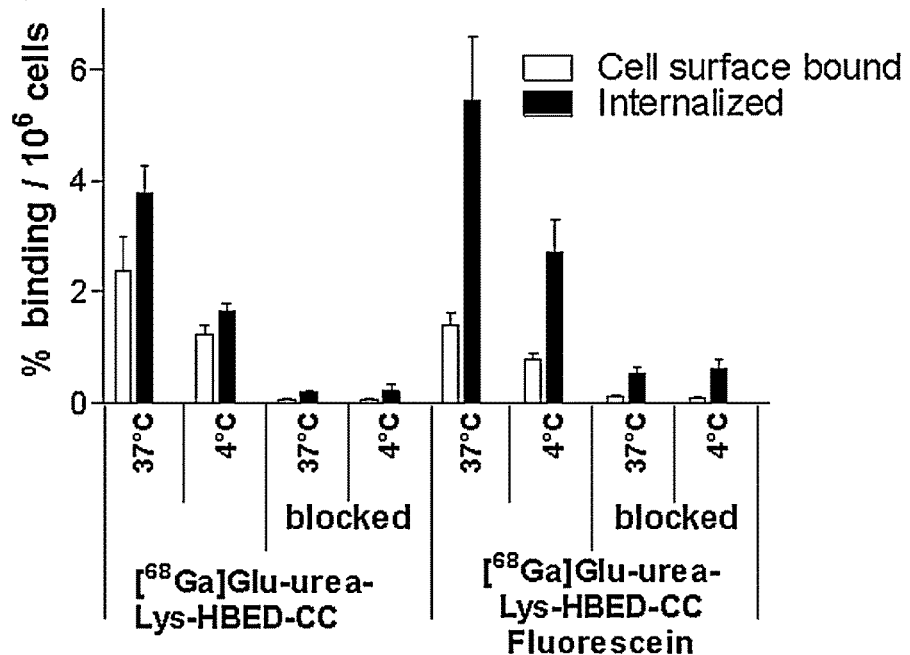

FIG. 4 shows the comparison of Glu-urea-Lys-HBED-CC-Fluorescein with the references Glu-urea-Lys-HBED-CC, both labeled with $^{68}Ga$, in terms of their specific cell surface binding and internalization properties on LNCaP cells. Specific cell uptake was determined by blocking with 500 µM 2-PMPA. Values are expressed as % of applied radioactivity bound to $10^6$ cells. Data are expressed as mean±SD (n=3).

Figure 5:
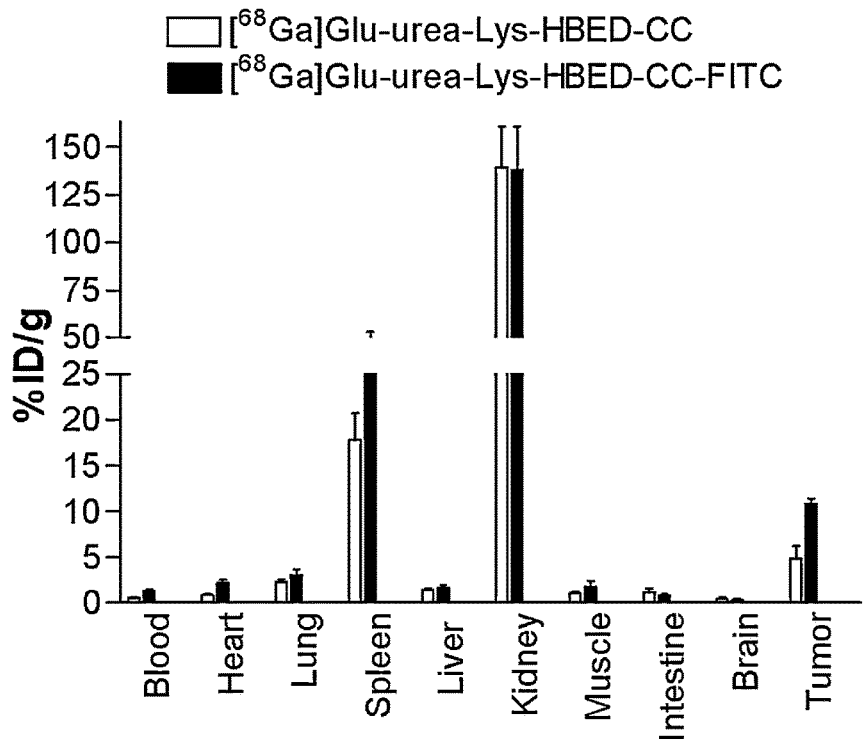

FIG. 5 depicts the organ distribution at one hour post injection of 0.06 nmol of the PSMA inhibitor Glu-urea-Lys either with [$^{68}Ga$]HBED-CC or [$^{68}Ga$]HBED-CC-fluorescein. Data are expressed as mean % ID/g tissue±SD (n=3).

Figure 6:
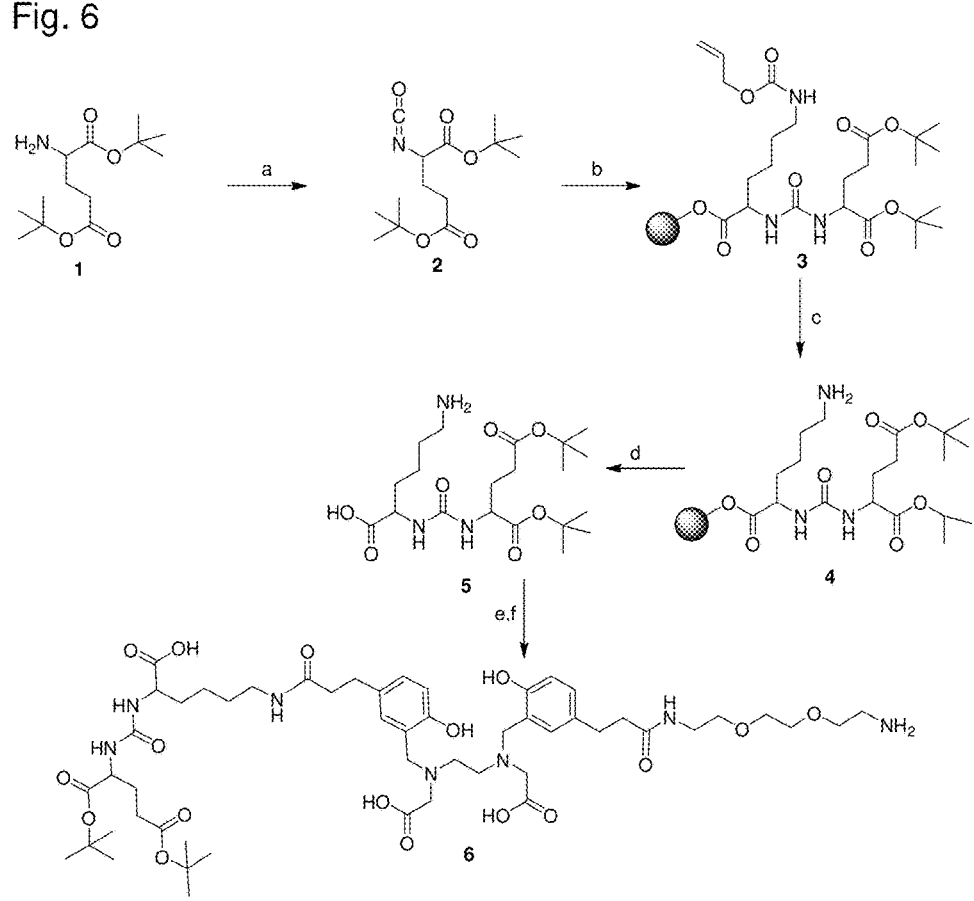

FIG. 6 shows the synthesis of Glu-urea-Lys-HBED-CC-PEG$_2$-NH$_2$ as precursor for the conjugation of various fluorescent dyes. Herein a. indicates triphosgene, DIPEA, CH$_2$Cl$_2$, 0° C.; b. indicates H-Lys(Alloc)-2CT-Resin, CH$_2$Cl$_2$; c. indicates Pd[P(C$_6$H$_5$)$_3$]$_4$, morpholine, CH$_2$Cl$_2$; d. indicates hexafluoroisopropanol/CH$_2$Cl$_2$; e. indicates (HBED-CC)TFP$_2$, DIPEA, DMF; and f. indicates 1,8-Diamino-3,6-Dioxaoctane.

Figure 7:
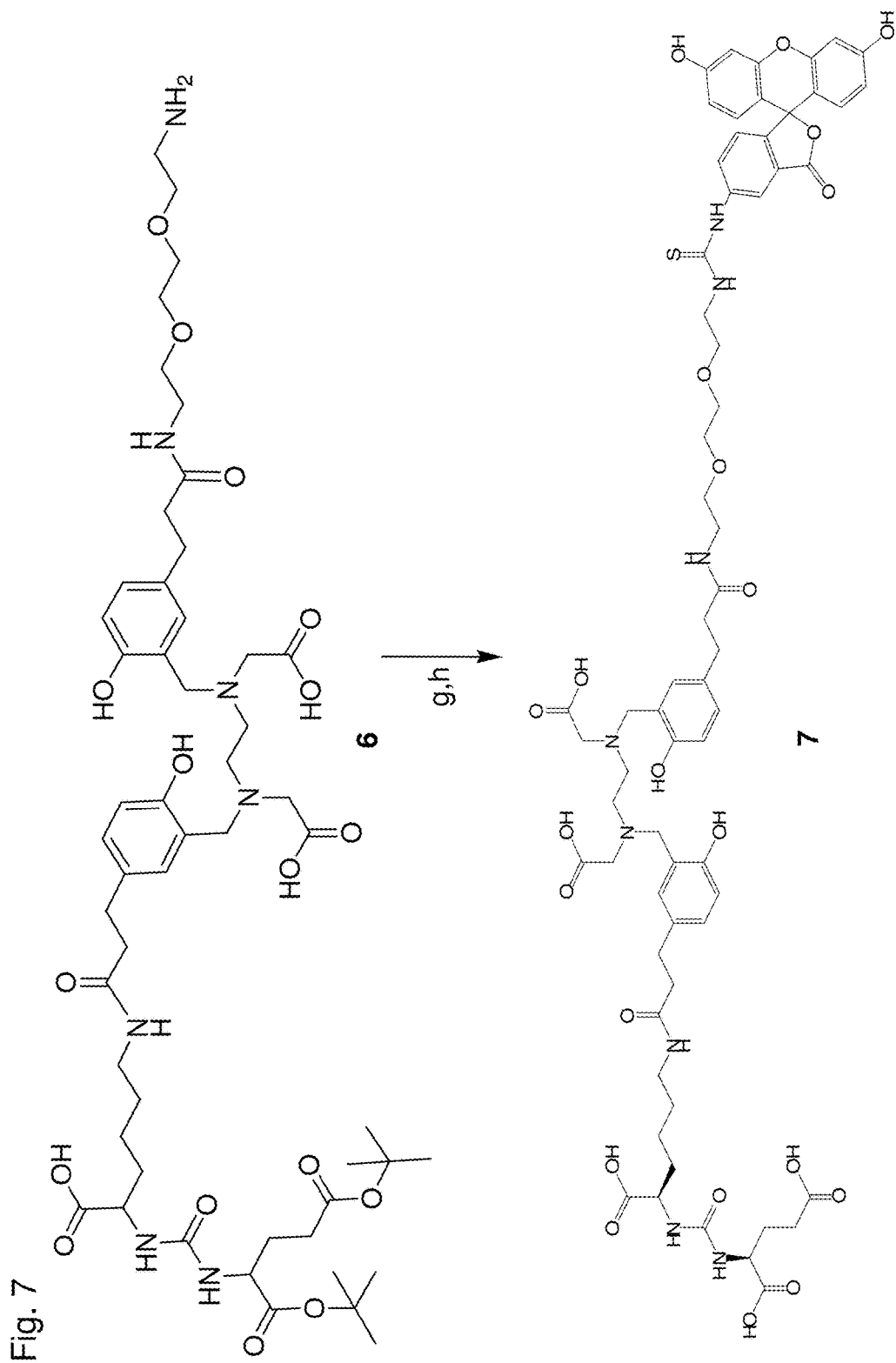

FIG. 7 shows the synthesis of Glu-urea-Lys-HBED-CC-PEG$_2$-Fluorescein. Herein, g. indicates fluorescein isothiocyanate (isomer I), DIPEA, DMF; and h. indicates TFA.

Figure 8:
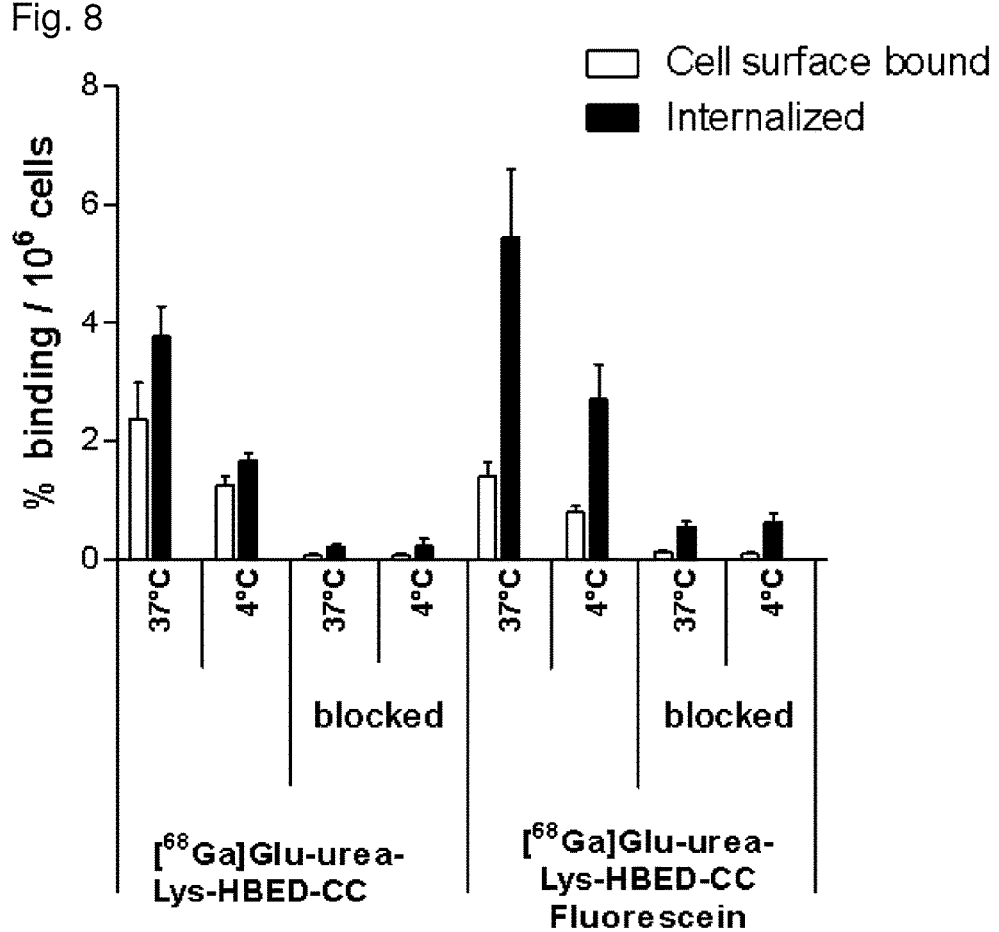

FIG. 8 shows the comparison of Glu-urea-Lys-HBED-CC-Fluorescein with the references Glu-urea-Lys-HBED-CC, both labeled with $^{68}Ga$, in terms of their specific cell surface binding and internalization properties on LNCaP cells. Specific cell uptake was determined by blocking with 500 µM 2-PMPA. Values are expressed as % of applied radioactivity bound to $10^6$ cells. Data are expressed as mean±SD (n=3).

Figure 9:
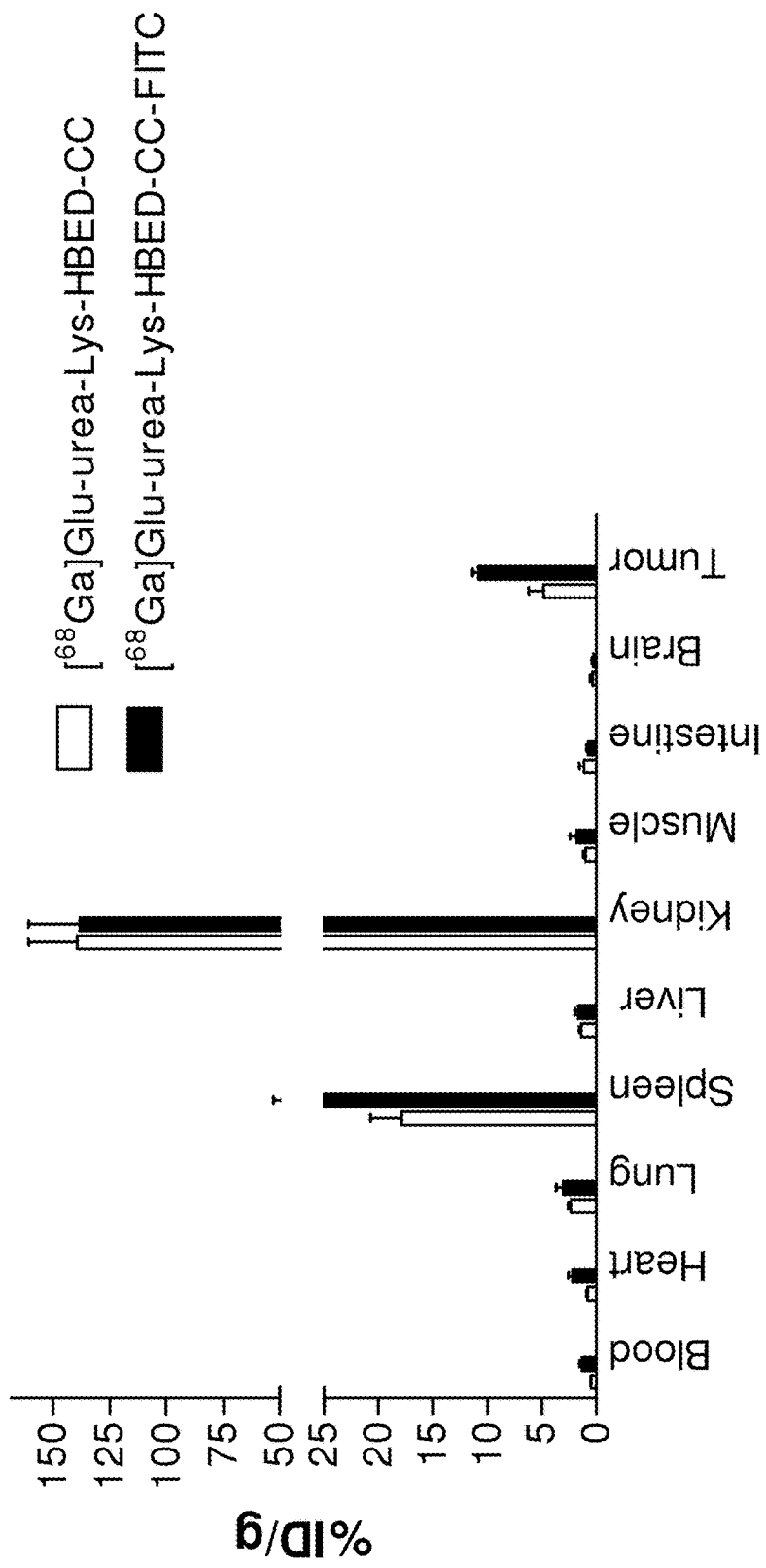

FIG. 9 shows the organ distribution at one hour post injection of 0.06 nmol of the PSMA inhibitor Glu-urea-Lys either with [$^{68}Ga$]HBED-CC or [$^{68}Ga$]HBED-CC-fluorescein. Data are expressed as mean % ID/g tissue±SD (n=3).

Figure 10:
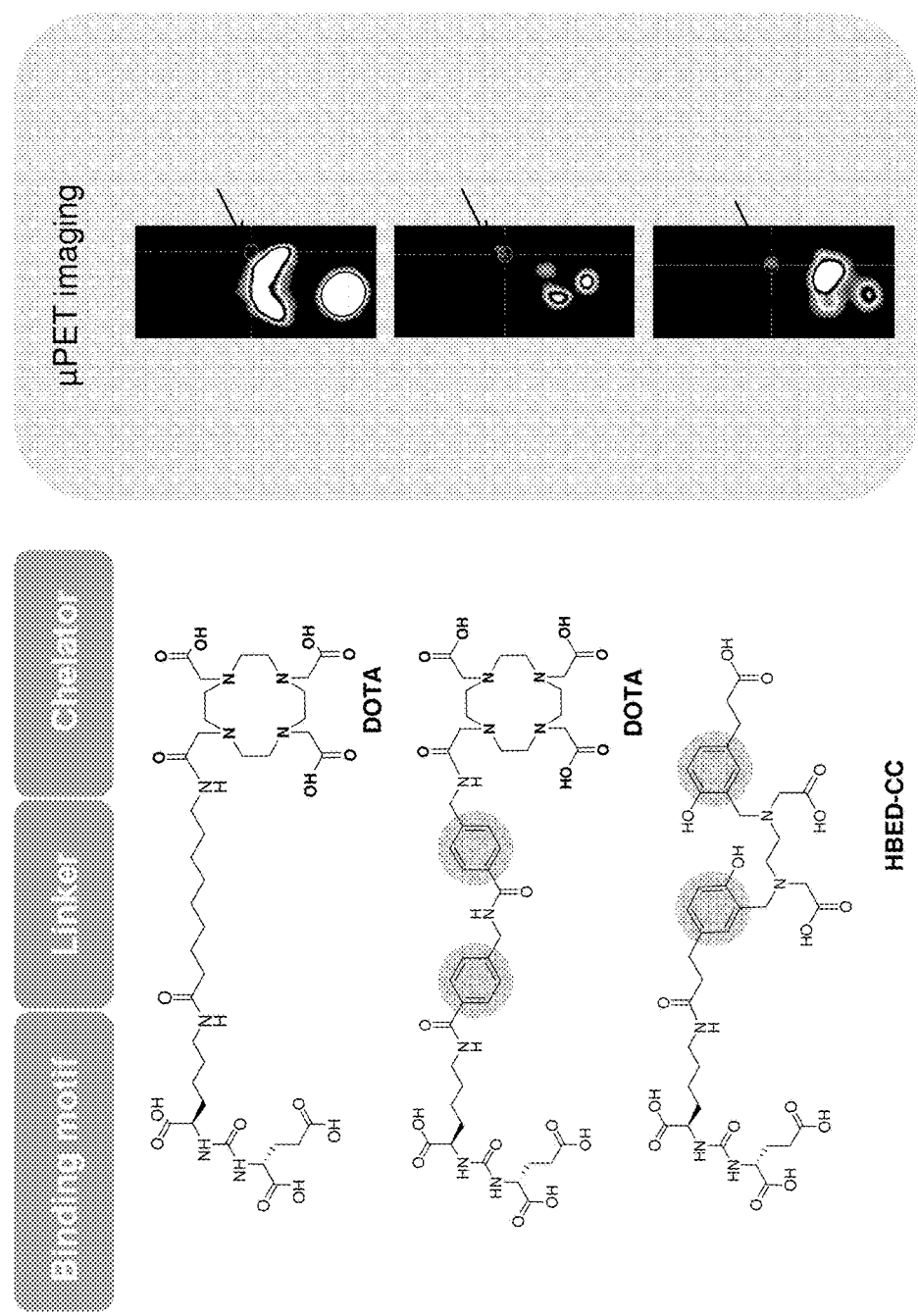

FIG. 10 shows PET imaging experiments in LNCaP tumor bearing nude mice 1 hour post injection of 10 MBq of the shown $^{68}Ga$ labeled compounds. If aromatic groups in the linker part of the molecule are completely missing, the tumor cannot be visualized. The arrow and the circle in the center of the dashed white cross indicate the tumor. In the HBED-CC structure, the tumor is particularly well visible.

Figure 11:
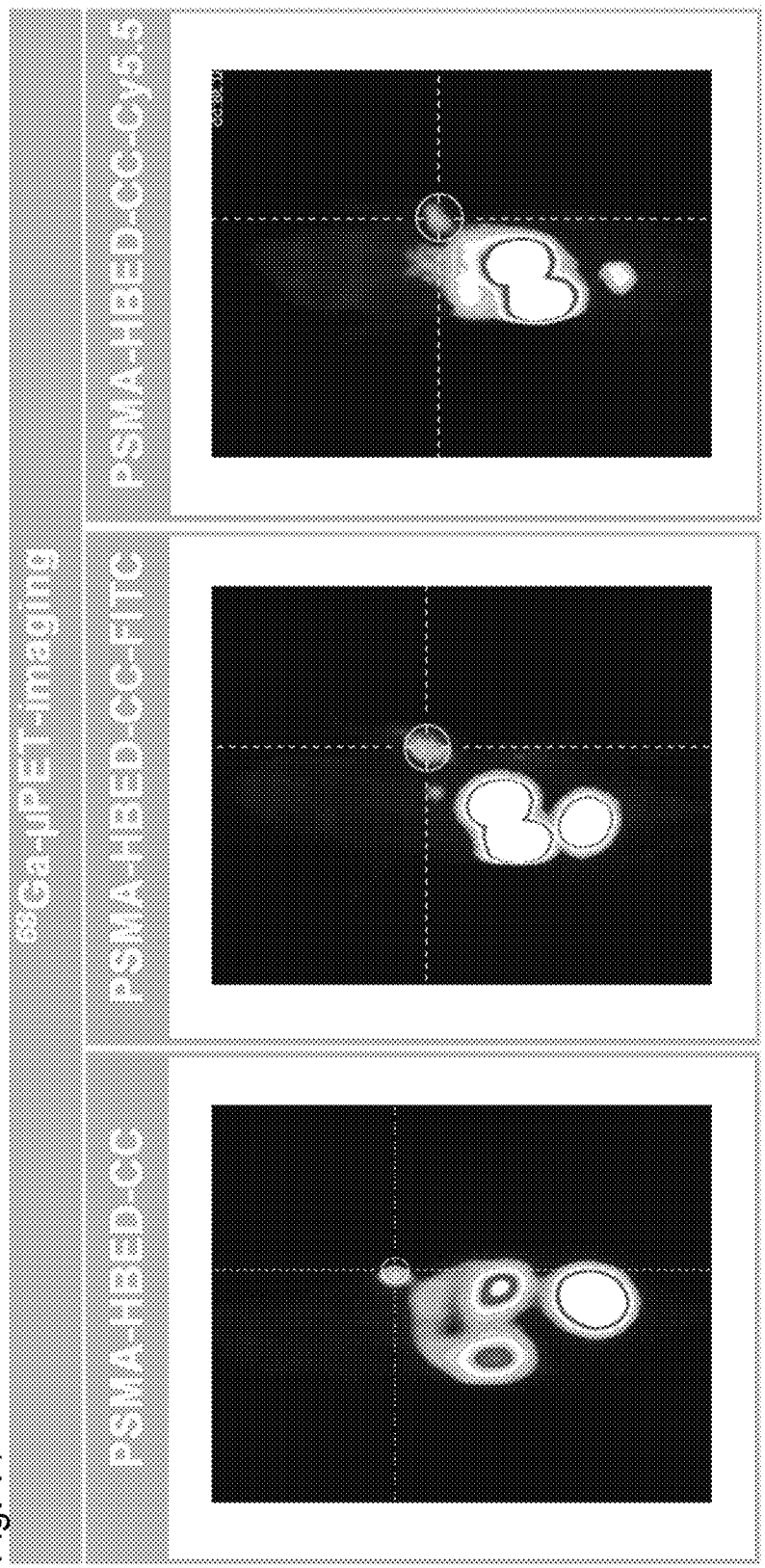

FIG. 11 shows comparative PET-imaging of $^{68}Ga$-labeled PSMA-HBED-CC conjugates. The PET-imaging shows comparable distribution of radioactivity and tumor uptake for PSMA-Ahx-HBED-CC, PSMA-HBED-CC-FITC, and PSMA-Ahx-HBED-CC-cyanine 5.5 1 hour post injection in LNCaP tumor-bearing nude mice.

Figure 12:
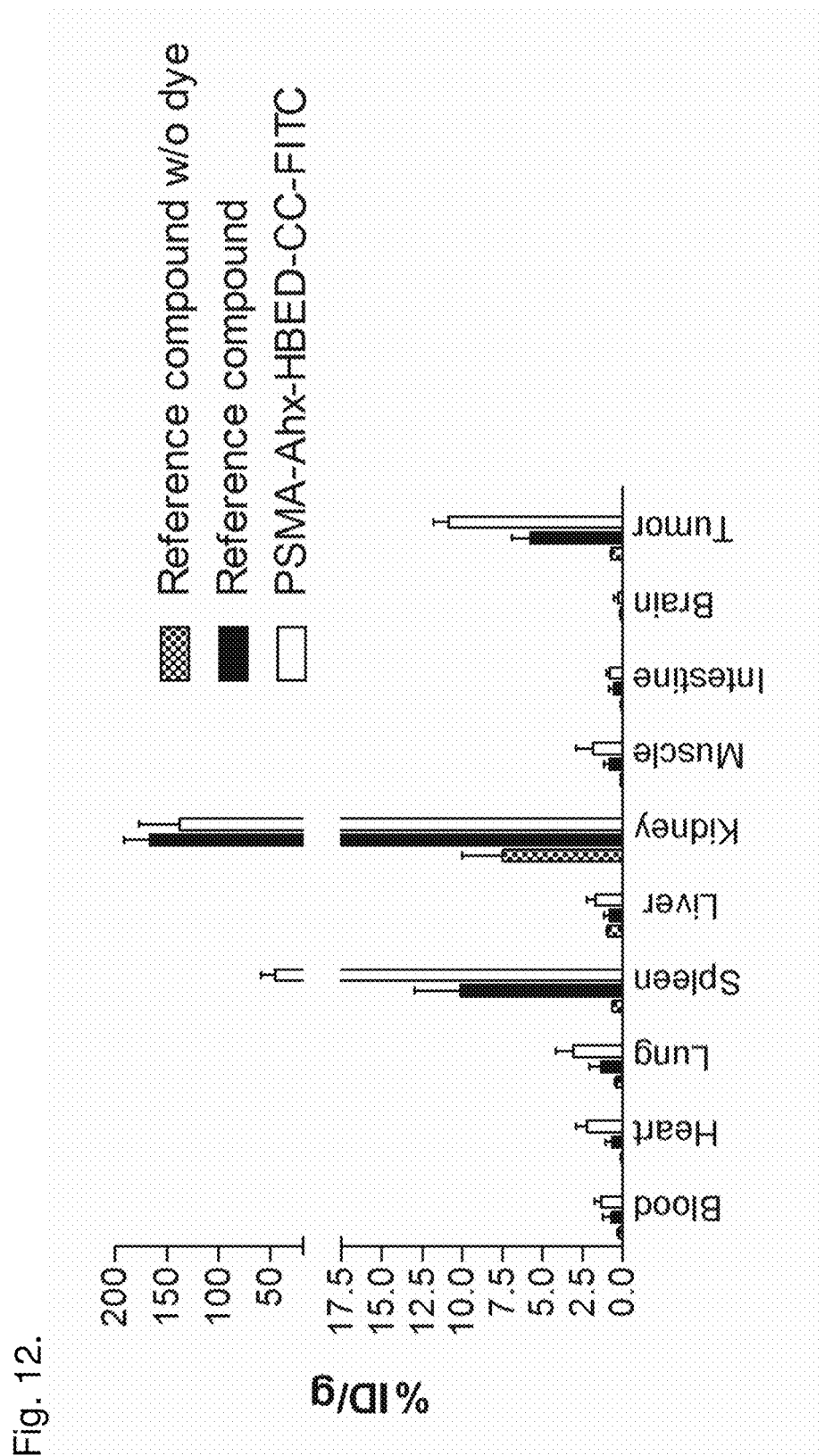

FIG. 12 shows the comparative organ distribution at 1 hour post injection of a reference compound published by Banerjee et al. (Banerjee et al., 2011, Angew Chem Int Ed Engl. 50(39):9167-9170, page 6, scheme 1, final product) and the corresponding compound without the fluorescent dye IRDye800CW bearing a free amino group of the lysyl moiety the dye IRDye800CW can be bound to and PSMA-Ahx-HBED-CC-FITC. As can be seen, the tumor uptake was significantly improved using PSMA-Ahx-HBED-CC-FITC.

EXAMPLES

Example 1

Materials and Methods

Analysis of the synthesized molecules was performed using reversed-phase high performance liquid chromatography (RP-HPLC; Chromolith RP-18e, 100×4.6 mm; Merck, Darmstadt, Germany) with a linear A-B gradient (0% B to 100% B in 6 min) at a flow rate of 4 mL/min (analysis) or 6 mL/min (purification). Solvent A consisted of 0.1% aqueous TFA and solvent B was 0.1% TFA in $CH_3CN$. The HPLC system (L6200 A; Merck-Hitachi, Darmstadt, Germany) was equipped with a UV and a gamma detector (Bioscan; Washington, USA). UV absorbance was measured at 214 nm, respectively. Mass spectrometry was performed with a MALDI-MS Daltonics Microflex system (Bruker Daltonics, Bremen, Germany). $^{68}Ga$ (half-life 68 min; $\beta^+$ 89%; $E_{\beta+}$ max. 1.9 MeV) was obtained from a $^{68}Ge/^{68}Ga$ generator based on pyrogallol resin support (Schuhmacher et al. 1981).
Synthesis An exemplarily synthesis protocol for producing a double-labeled probe for molecular imaging is exemplified in FIG. 3.

To synthesize the pharmacophore Glu-urea-Lys, the isocyanate of the glutamyl moiety (indicated as 1 in FIG. 3) was generated in situ by adding a mixture of 3 mmol of bis(tert-butyl) L-glutamate hydrochloride (Bachem, Switzerland) and 1.5 mL of N-ethyldiisopropylamine (DIPEA) in 200 mL of dry $CH_2Cl_2$ to a solution of 1 mmol triphosgene in 10 mL of dry $CH_2Cl_2$ at 0° C. over 4 h. After agitation of the reaction mixture for one further hour at 25° C., 0.5 mmol of a resin-immobilized (2-chloro-tritylresin, Merck, Darmstadt) ε-allyloxycarbonyl protected lysine was added in 4 mL DCM and reacted for 16 h with gentle agitation leading to compound indicated as 3 in FIG. 3. The resin was filtered off and the allyloxy-protecting group was removed using 100 mg tetrakis(triphenyl)palladium(0) (Sigma-Aldrich, Germany) and 400 µL morpholine in 4 mL $CH_2Cl_2$ for 3 hours resulting in the compound indicated as 4 in FIG. 3. Compound 4 was cleaved from the resin by reacting with 4 mL of a 30% 1,1,1-3,3,3-hexafluoroisopropanole (HFIP) in $CH_2Cl_2$ for two hours at ambient temperature resulting in the tert-butyl protected crude product 5 which was purified via RP-HPLC.

The bis-activated ester (HBED-CC)$TFP_2$ was synthesized as previously described (Schafer et al. 2012). The precursor for the conjugation of the Dye was synthesized by reacting 66 mg (0.08 mmol) of the bis-activated ester (HBED-CC) $TFP_2$ with 39 mg (0.072 mmol) of the TFA salt of bis (tert.butyl)Glu-urea-Lys (5) in 1 ml of dry DMF and 25 µl of DIPEA at room temperature. After 4 hours 75 µL of 1,8-Diamino-3,6-Dioxaoctane (0.52 mmol) were added and the reaction was carried out at room temperature for 16 hours. After evaporation of the solvent, the crude product indicated as 6 in FIG. 3 was purified via RP-HPLC (Gradient: 10% $CH_3CN$ to 40% $CH_3CN$ in 10.5 min, Flow 6 ml/min; Detection at 214 nm). (yield: 32 mg; 34%). (Calc. 1076.24; Found: 1077.2 (M+W)).

Conjugation of fluorescein was performed by reacting 6 mg of the HBED-CC conjugate indicated as 6 in FIG. 3 (0.005 mmol) with 2.3 mg (0.006 mmol) Fluorescein isothiocyanate (isomer I) in 1 mL of dry DMF supplemented with 15 µL DIPEA at room temperature for 16 hours. After evaporation of the solvent, the product 7 was isolated via RP-HPLC (Gradient: 15% $CH_3CN$ to 51% $CH_3CN$ in 9.2 min, Flow 6 mL/min; Detection at 214 nm). (yield: 4.2 mg; 57%): (Calc. 1465.62; Found: 1466.4 (M+W)). The cleavage of the remaining protecting groups was done by using TFA. (Calc. 1353.4; Found: 1354.3 (M+H$^+$)).
$^{68}Ga$-Labelling The conjugates (0.1-1 nmol in 0.1 M HEPES buffer, pH=7.5, 100 µL) were added to a mixture of 10 µL HEPES solution (2.1 M) and 40 µL [$^{68}Ga$]Ga$^{3+}$ eluate (25-60 MBq). The pH of the labelling solution was adjusted to 4.2 using 30% NaOH. The reaction mixture was incubated at 80° C. for 2 minutes. The radiochemical yield (RCY) was determined via analytical RP-HPLC.
Cell Culture For binding studies and in vivo experiments LNCaP cells (metastatic lesion of human prostatic adenocarcinoma, ATCC CRL-1740) were cultured in RPMI medium supplemented with 10% fetal calf serum and Glutamax (PAA, Austria).

During cell culture, cells were grown at 37° C. in an incubator with humidified air, equilibrated with 5% $CO_2$. The cells were harvested using trypsin-ethylenediaminetetraacetic acid (trypsin-EDTA; 0.25% trypsin, 0.02% EDTA, all from PAA, Austria) and washed with PBS.
Cell Binding and Internalization The competitive cell binding assay and internalization experiments were performed as described previously (Eder et al. 2012). Briefly, the respective cells ($10^5$ per well) were incubated with the radiometal ($^{68}Ga$-labeled [Glu-urea-Lys (Ahx)]$_2$-HBED-CC (Schafer et al. 2012)) in the presence of 12 different concentrations of analyte (0-5000 nM, 100 µL/well). After incubation, washing was carried out using a multiscreen vacuum manifold (Millipore, Billerica, Mass.). Cell-bound radioactivity was measured using a gamma counter (Packard Cobra II, GMI, Minnesota, USA). The 50% inhibitory concentration (IC50) was calculated by fitting the data using a nonlinear regression algorithm (GraphPad Software). Experiments were performed three times.

To determine the specific cell uptake and internalization, $10^5$ cells were seeded in poly-L-lysine coated 24-well cell culture plates 24 h before incubation. After washing, the cells were incubated with 25 nM of the radiolabeled compounds for 45 min at 37° C. and at 4° C., respectively. Specific cellular uptake was determined by competitive blocking with 2-(phosphonomethyl)pentanedioic acid (500 µM final concentration, PMPA, Axxora, Loerrach, Germany). Cellular uptake was terminated by washing 4 times with 1 mL of ice-cold PBS. Cells were subsequently incubated twice with 0.5 mL glycine-HCl in PBS (50 mM, pH=2.8) for 5 min to remove the surface-bound fraction. The cells were washed with 1 mL of ice-cold PBS and lysed using 0.3 N NaOH (0.5 mL). The surface-bound and the internalized fractions were measured in a gamma counter. The cell uptake was calculated as percent of the initially added radioactivity bound to $10^6$ cells [% ID/$10^6$ cells].
Biodistribution 7- to 8-week-old male BALB/c nu/nu mice (Charles River Laboratories) were subcutaneously inoculated into the right trunk with 5×$10^6$ cells of LNCaP (in 50% Matrigel; Becton Dickinson, Heidelberg, Germany). The tumors were allowed to grow until approximately 1 cm³ in size. The radiolabeled compounds were injected into the tail vein (approx. 1 MBq per mouse; 0.06 nmol). At 1 h after injection the animals were sacrificed. Organs of interest were dissected, blotted dry, and weighed. The radioactivity was measured using a gamma counter and calculated as % ID/g.

Results

In Vitro Cell Binding Properties

An in vitro competitive cell binding assay was performed in order to determine the binding potential expressed as $IC_{50}$-values of Glu-urea-Lys-HBED-CC-Fluorescein in comparison to the reference Glu-urea-Lys(Ahx)-HBED-CC. The $IC_{50}$ values of Glu-urea-Lys-HBED-CC-Fluorescein and Glu-urea-Lys(Ahx)-HBED-CC were 11.14±1.16 nM and 9.82±1.26 nM, respectively, indicating that the PSMA specificity was not affected by the conjugation of fluorescein.

The functionality of the dual-imaging agent Glu-urea-Lys-HBED-CC-fluorescein was additionally investigated on cellular basis by analyzing the internalization and cell surface binding properties (FIG. 4). Glu-urea-Lys-HBED-CC-fluorescein was specifically internalized by LNCaP cells shown by competitive blocking with the PSMA inhibitor 2-PMPA (P<0.001). The cell uptake and internalization profile was not considerably changed in the course of the chemical combination of Glu-urea-Lys-HBED-CC and Fluorescein, indicating that the dye on this position has no influence on the cell binding properties of the PSMA-binding molecule.

Organ Distribution

In order to demonstrate the functionality of the molecule in vivo, organ distribution studies with tumor bearing xenografts were performed. FIG. 5 and Table I show that the tumor uptake of the dye-conjugate Glu-urea-Lys-HBED-CC-fluorescein in PSMA positive LNCaP tumors (10.86± 0.94% ID/g) was higher compared to the non-conjugated reference Glu-urea-Lys(Ahx)-HBED-CC (4.89±1.34% ID/g). Furthermore, the distribution profiles of both compounds, Glu-urea-Lys-HBED-CC-fluorescein and Glu-urea-Lys(Ahx)-HBED-CC, in healthy organs were comparable indicating similar background activity of both compounds in vivo. Thus, the in vivo tumor-targeting properties of Glu-urea-Lys-HBED-CC-fluorescein are at least comparable to the reference Glu-urea-Lys(Ahx)-HBED-CC.

TABLE I

Organ distribution of the labeled probes at 1 h post injection.

| | Glu-urea-Lys-HBED-CC | | | Glu-urea-Lys-HBED-CC-dye | | |
|---|---|---|---|---|---|---|
| | Mean | SD | N | Mean | SD | N |
| Blood | 0.53 | 0.04 | 3 | 1.34 | 0.40 | 3 |
| Heart | 0.83 | 0.08 | 3 | 2.22 | 0.68 | 3 |
| Lung | 2.36 | 0.27 | 3 | 3.09 | 1.07 | 3 |
| Spleen | 17.88 | 2.87 | 3 | 45.24 | 13.48 | 3 |
| Liver | 1.43 | 0.19 | 3 | 1.71 | 0.54 | 3 |
| Kidney | 139.44 | 21.40 | 3 | 138.18 | 39.08 | 3 |
| Muscle | 1.00 | 0.24 | 3 | 1.84 | 1.06 | 3 |
| Intestine | 1.14 | 0.46 | 3 | 0.81 | 0.23 | 3 |
| Brain | 0.40 | 0.19 | 3 | 0.31 | 0.22 | 3 |
| Tumor | 4.89 | 1.34 | 3 | 10.86 | 0.94 | 3 |

Discussion

As the cell binding properties were not affected by the conjugation of the dye, Glu-urea-Lys-HBED-CC-dye conjugates as exemplified might represent a tool to follow the intracellular distribution of $^{68}$Ga-labeled Glu-urea-Lys (Ahx)-HBED-CC. An organ distribution study showed that the absolute tumor uptake and the tumor-to-background ratios were at least comparable to non-conjugated Glu-urea-Lys(Ahx)-HBED-CC which has recently provided promising results as a novel clinical PET-tracer for the diagnosis of recurrent prostate cancer (Afshar-Oromieh et al. 2013, Afshar-Oromieh et al. 2014). Consequently, conjugated to clinical relevant dyes this tracer may serve as a multimodal imaging agent offering staging by PET imaging on the one hand and fluorescence signals such as, e.g., intraoperative fluorescence signals, on the other hand which might help to distinguish between neoplasia and healthy tissue during surgery.

Example 2

Syntheses of the Preferred Precursor

To synthesize the pharmacophore Glu-urea-Lys, the isocyanate of the glutamyl moiety 1 was generated in situ by adding a mixture of 3 mmol of bis(tert-butyl) L-glutamate hydrochloride (Bachem, Switzerland) and 1.5 mL of N-ethyldiisopropylamine (DIPEA) in 200 mL of dry $CH_2Cl_2$ to a solution of 1 mmol triphosgene in 10 mL of dry $CH_2Cl_2$ at 0° C. over 4 h. After agitation of the reaction mixture for one further hour at 25° C., 0.5 mmol of a resin-immobilized (2-chloro-tritylresin, Merck, Darmstadt) ε-allyloxycarbonyl protected lysine was added in 4 mL DCM and reacted for 16 h with gentle agitation leading to compound 3. The resin was filtered off and the allyloxy-protecting group was removed using 100 mg tetrakis(triphenyl)palladium(0) (Sigma-Aldrich, Germany) and 400 μL morpholine in 4 mL $CH_2Cl_2$ for 3 hours resulting in 4. Compound 4 was cleaved from the resin by reacting with 4 mL of a 30% 1,1,1-3,3,3-hexafluoroisopropanole (HFIP) in $CH_2Cl_2$ for two hours at ambient temperature resulting in the tert-butyl protected crude product 5 which was purified via RP-HPLC.

The bis-activated ester (HBED-CC)TFP$_2$ was synthesized as previously described (Schäfer et al., 2012). The precursor for the conjugation of the Dye was synthesized by reacting 66 mg (0.08 mmol) of the bis-activated ester (HBED-CC)TFP$_2$ with 39 mg (0.072 mmol) of the TFA salt of bis(tert.butyl)Glu-urea-Lys (5) in 1 ml of dry DMF and 25 μl of DIPEA at room temperature. After 4 hours 75 μL of 1,8-Diamino-3,6-Dioxaoctane (0.52 mmol) were added and the reaction was carried out at room temperature for 16 hours. After evaporation of the solvent, the crude product 6 was purified via RP-HPLC (Gradient: 10% $CH_3CN$ to 40% $CH_3CN$ in 10.5 min, Flow 6 ml/min; Detection at 214 nm). (yield: 32 mg; 34%). (Calc. 1076.24; Found: 1077.2 $(M+H^+)$).

This procedure is further depicted in FIG. 6.

In order to introduce the most preferred aminohexanoic acid spacer between the binding motif and the chelator HBED-CC compound 4 is reacted with 2 mmol of the Fmoc-protected 6-amino-hexanoic acid (Sigma-Aldrich, Germany), 1.96 mmol of HBTU (Merck, Darmstadt, Germany), and 2 mmol of N-ethyl-diisopropylamine in a final volume of 4 mL DMF.

Example PSMA-HBED-CC-FITC

Conjugation of fluorescein was performed by reacting 6 mg of the HBED-CC conjugate 6 (0.005 mmol) with 2.3 mg (0.006 mmol) Fluorescein isothiocyanate (isomer I) in 1 mL of dry DMF supplemented with 15 μL DIPEA at room temperature for 16 hours. After evaporation of the solvent, the product 7 was isolated via RP-HPLC (Gradient: 15% $CH_3CN$ to 51% $CH_3CN$ in 9.2 min, Flow 6 mL/min;

Detection at 214 nm). (yield: 4.2 mg; 57%): (Calc. 1465.62; Found: 1466.4 (M+H⁺)). The cleavage of the remaining protecting groups was done by using TFA. (Calc. 1353.4; Found: 1354.3 (M+H⁺)). This is further depicted in FIG. 7.

Analogously, other fluorescent dyes such as, e.g., Alexa488, Cy5.5, sulfoCy5, ATTO647N, ICG and IRdye800CW were conjugated. Then, a corresponding activated form of the respective fluorescent dye is used instead of FITC. Analogously also rhodamine type dyes such as those shown by Kolmakov et al. (cf., Kolamkov et al., 2012; Kolmakov et al., 2014), such as e.g., KK114 or Abberior Star 635P shown therein, are conjugated.

Examples for the structures obtainable thereby are the following:

PSMA-Ahx-HBED-CC-FITC:

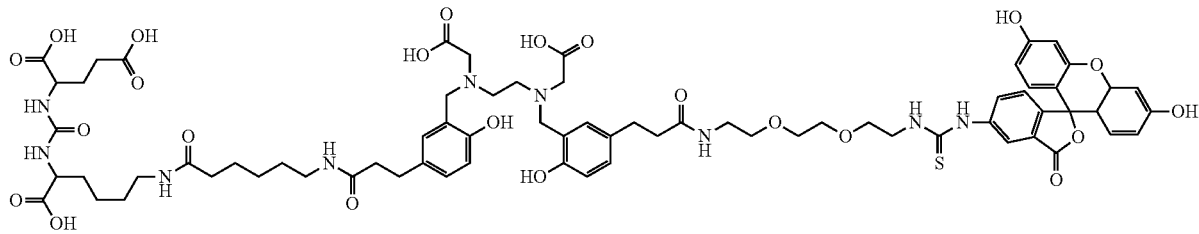 [SMILES: O=C(O)CCC(NC(=O)NC(CCCCNC(=O)CCCCCNC(=O)CCc1ccc(O)c(CN(CCN(CC(=O)O)Cc2cc(CCC(=O)NCCOCCOCCNC(=S)Nc3ccc4c(c3)C(=O)OC43c4ccc(O)cc4OC4C=C(O)C=CC43)ccc2O)CC(=O)O)c1)C(=O)O)C(=O)O]

PSMA-Ahx-HBED-CC-Alexa488:

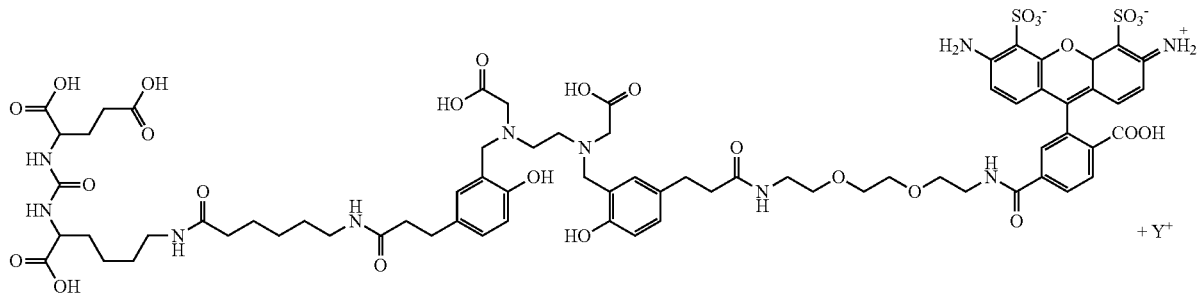

PSMA-Ahx-HBED-CC-cyanine 5.5:

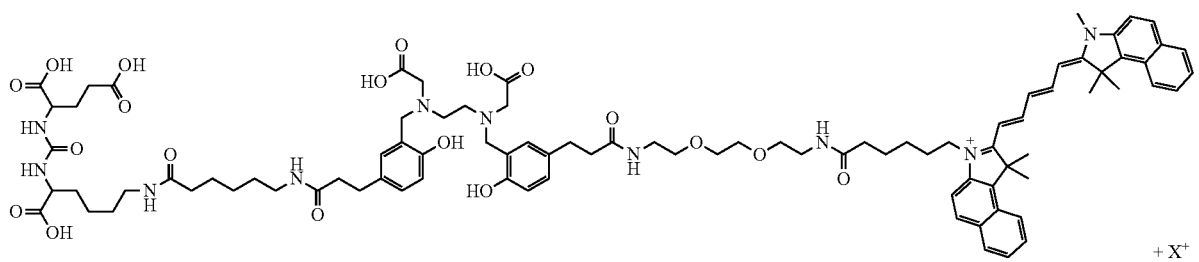

PSMA-Ahx-HBED-CC-sulfoCy5:

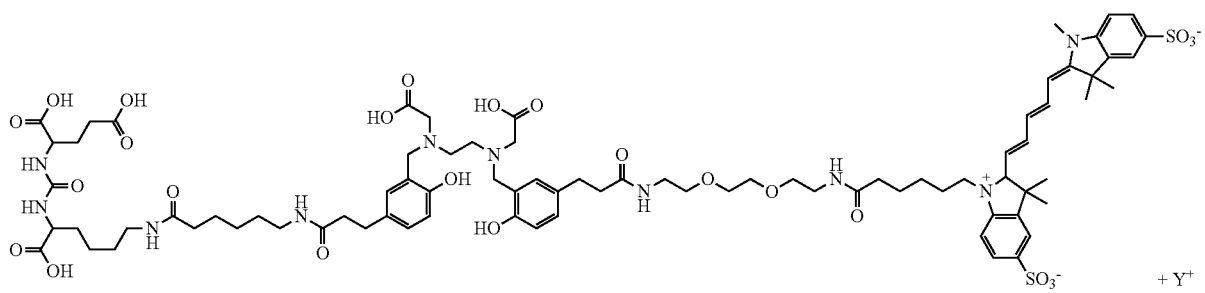

PSMA-Ahx-HBED-CC-ATT0647N:

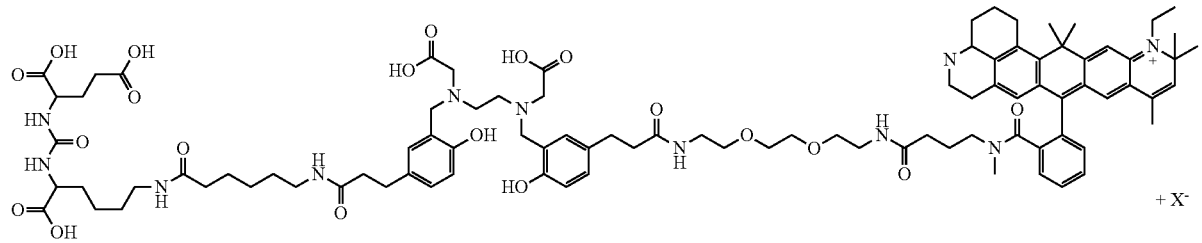

PSMA-Ahx-HBED-CC-ICG:

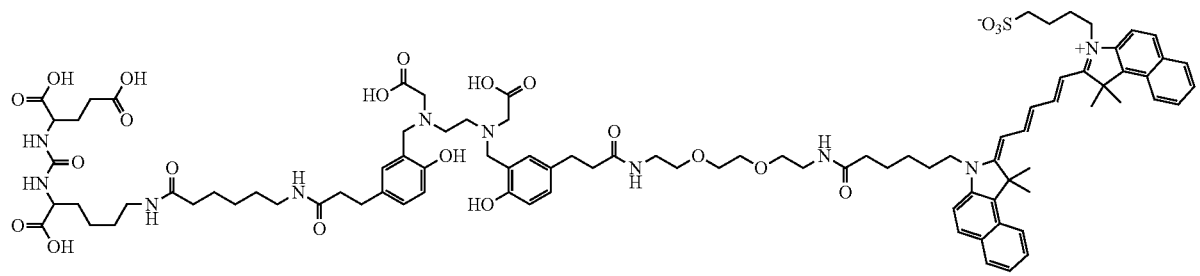

PSMA-Ahx-HBED-CC-IRdye800CW:

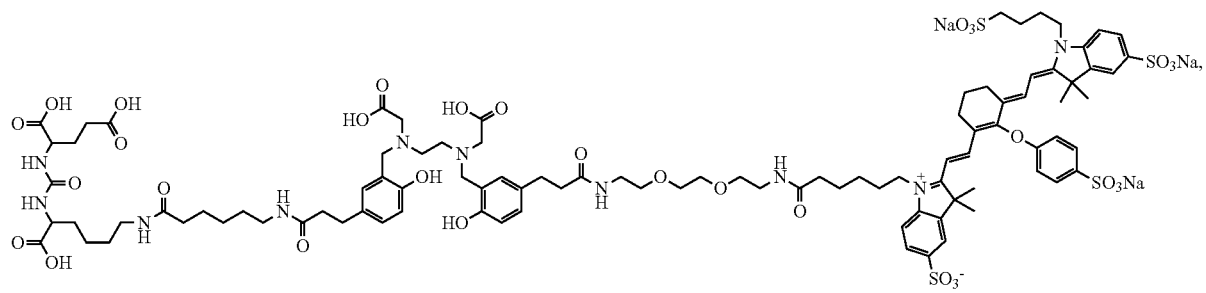

wherein $X^-$ is a pharmaceutically acceptable negatively charged counterion; and
wherein $Y^+$ is a pharmaceutically acceptable positively charged counterion.

Herein the respective counterion depends on the used surrounding liquids such as those comprised in the buffer the compound is dissolved in and the body fluids after injection in vivo. In vivo, extracellularly, one of the main, but not sole positively charged counterions is $Na^+$ and one of the main, but not sole negatively charged counterions is $Cl^-$.

$^{68}$Ga-Labelling

The conjugates (0.1-1 nmol in 0.1 M HEPES buffer, pH=7.5, 100 μL) were added to a mixture of 10 μL HEPES solution (2.1 M) and 40 μL [$^{68}$Ga]Ga$^{3+}$ eluate (25-60 MBq). The pH of the labelling solution was adjusted to 4.2 using 30% NaOH. The reaction mixture was incubated at 80° C. for 2 minutes. The radiochemical yield (RCY) was determined via analytical RP-HPLC.

Cell Culture

For binding studies and in vivo experiments LNCaP cells (metastatic lesion of human prostatic adenocarcinoma, ATCC CRL-1740) were cultured in RPMI medium supplemented with 10% fetal calf serum and Glutamax (PAA, Austria). During cell culture, cells were grown at 37° C. in an incubator with humidified air, equilibrated with 5% $CO_2$. The cells were harvested using trypsin-ethylenediaminetetraacetic acid (trypsin-EDTA; 0.25% trypsin, 0.02% EDTA, all from PM, Austria) and washed with PBS.

Cell Binding and Internalization

The competitive cell binding assay and internalization experiments were performed as described previously (Eder et al., 2012). Briefly, the respective cells (10$^5$ per well) were incubated with the radioligand ($^{68}$Ga-labeled [Glu-urea-Lys(Ahx)]$_2$-HBED-CC (Schäfer et al., 2012)) in the presence of 12 different concentrations of analyte (0-5000 nM, 100 μL/well). After incubation, washing was carried out using a multiscreen vacuum manifold (Millipore, Billerica, Mass.). Cell-bound radioactivity was measured using a gamma counter (Packard Cobra II, GMI, Minnesota, USA). The 50% inhibitory concentration (IC50) was calculated by fitting the data using a nonlinear regression algorithm (GraphPad Software). Experiments were performed three times.

To determine the specific cell uptake and internalization, 10$^5$ cells were seeded in poly-L-lysine coated 24-well cell culture plates 24 h before incubation. After washing, the cells were incubated with 25 nM of the radiolabeled compounds for 45 min at 37° C. and at 4° C., respectively.

Specific cellular uptake was determined by competitive blocking with 2-(phosphonomethyl)pentanedioic acid (500 μM final concentration, PMPA, Axxora, Loerrach, Germany). Cellular uptake was terminated by washing 4 times with 1 mL of ice-cold PBS. Cells were subsequently incubated twice with 0.5 mL glycine-HCl in PBS (50 mM, pH=2.8) for 5 min to remove the surface-bound fraction. The cells were washed with 1 mL of ice-cold PBS and lysed using 0.3 N NaOH (0.5 mL). The surface-bound and the internalized fractions were measured in a gamma counter. The cell uptake was calculated as percent of the initially added radioactivity bound to $10^6$ cells [% ID/$10^6$ cells].

Biodistribution 7- to 8-week-old male BALB/c nu/nu mice (Charles River Laboratories) were subcutaneously inoculated into the right trunk with 5×$10^6$ cells of LNCaP (in 50% Matrigel; Becton Dickinson, Heidelberg, Germany). The tumors were allowed to grow until approximately 1 $cm^3$ in size. The radiolabeled compounds were injected into the tail vein (approx. 1 MBq per mouse; 0.06 nmol). At 1 h after injection the animals were sacrificed. Organs of interest were dissected, blotted dry, and weighed. The radioactivity was measured using a gamma counter and calculated as % ID/g.

Results

PSMA-HBED-CC-FITC

In Vitro Cell Binding Properties

An in vitro competitive cell binding assay was performed in order to determine the binding potential expressed as $IC_{50}$-values of Glu-urea-Lys-HBED-CC-Fluorescein in comparison to the reference Glu-urea-Lys(Ahx)-HBED-CC. The $IC_{50}$ values of Glu-urea-Lys-HBED-CC-Fluorescein and Glu-urea-Lys(Ahx)-HBED-CC were 11.14±1.16 nM and 9.82±1.26 nM, respectively, indicating that the PSMA specificity was not affected by the conjugation of fluorescein.

The functionality of the dual-imaging agent Glu-urea-Lys-HBED-CC-fluorescein was additionally investigated on cellular basis by analyzing the internalization and cell surface binding properties (FIG. 8). Glu-urea-Lys-HBED-CC-fluorescein was specifically internalized by LNCaP cells shown by competitive blocking with the PSMA inihibor 2-PMPA (P<0.001). The cell uptake and internalization profile was not considerably changed in the course of the chemical combination of Glu-urea-Lys-HBED-CC and Fluorescein, indicating that the dye on this position has no influence on the cell binding properties of the PSMA-binding molecule.

Organ Distribution

In order to demonstrate the functionality of the molecule in vivo, organ distribution studies with tumor bearing xenografts were performed. FIG. 9 and Table II show that the tumor uptake of the dye-conjugate Glu-urea-Lys-HBED-CC-fluorescein in PSMA positive LNCaP tumors (10.86±0.94% ID/g) was higher compared to the non-conjugated reference Glu-urea-Lys(Ahx)-HBED-CC (4.89±1.34% ID/g). Furthermore, the distribution profiles of both compounds, Glu-urea-Lys-HBED-CC-fluorescein and Glu-urea-Lys(Ahx)-HBED-CC, in healthy organs were comparable indicating similar background activity of both compounds in vivo. Thus, the in vivo tumor-targeting properties of Glu-urea-Lys-HBED-CC-fluorescein are at least comparable to the reference Glu-urea-Lys(Ahx)-HBED-CC.

TABLE II

| Organ distribution data 1 h post injection | | | | | | |
|---|---|---|---|---|---|---|
| | Glu-urea-Lys-HBED-CC | | | Glu-urea-Lys-HBED-CC-dye | | |
| | Mean | SD | N | Mean | SD | N |
| Blood | 0.53 | 0.04 | 3 | 1.34 | 0.40 | 3 |
| Heart | 0.83 | 0.08 | 3 | 2.22 | 0.68 | 3 |
| Lung | 2.36 | 0.27 | 3 | 3.09 | 1.07 | 3 |
| Spleen | 17.88 | 2.87 | 3 | 45.24 | 13.48 | 3 |
| Liver | 1.43 | 0.19 | 3 | 1.71 | 0.54 | 3 |
| Kidney | 139.44 | 21.40 | 3 | 138.18 | 39.08 | 3 |
| Muscle | 1.00 | 0.24 | 3 | 1.84 | 1.06 | 3 |
| Intestine | 1.14 | 0.46 | 3 | 0.81 | 0.23 | 3 |
| Brain | 0.40 | 0.19 | 3 | 0.31 | 0.22 | 3 |
| Tumor | 4.89 | 1.34 | 3 | 10.86 | 0.94 | 3 |

Discussion

As the cell binding properties were not affected by the conjugation of the fluorescent dye, Glu-urea-Lys-HBED-CC-fluorescein might represent a tool to follow the intracellular distribution of $^{68}$Ga-labeled Glu-urea-Lys(Ahx)-HBED-CC. An organ distribution study showed that the absolute tumor uptake and the tumor-to-background ratios were at least comparable to non-conjugated Glu-urea-Lys (Ahx)-HBED-CC which has recently shown promising results as a novel clinical PET-tracer for the diagnosis of recurrent prostate cancer (Afshar-Oromieh et al., 2013, Afshar-Oromieh et al., 2014). Consequently, conjugated to clinical relevant dyes this tracer might serve as a multimodal imaging agent offering staging by PET imaging on the one hand and intraoperative fluorescence signals on the other hand which might help to distinguish between prostate cancer and healthy tissue during surgery.

Example 3

It was found that the chelator HBED-CC (N,N'-bis-[2-hydroxy-5-(carboxyethyl)benzyl]ethylenediamine-N,N'-diacetic acid), represents an acyclic complexing agent especially allowing efficient radiolabeling with $^{68}$Ga even at ambient temperature (Eder et al., 2010; Eder et al., 2008). It was found that combining HBED-CC with the PSMA inhibitor Glu-urea-Lys, a favorable aromatic part is introduced into the radiotracer which was found to be beneficial for a sustainable interaction with the PSMA receptor, putatively with the accessory hydrophobic pocket of the PSMA binding site (Eder et al., 2012; Kularatne et al., 2009; Liu et al., 2008). Indeed, it has been shown in a preclinical study that the replacement of HBED-CC by DOTA (1,4,7,10-tetraaza-cyclododecane-N,N',N'',N'''-tetraacetic acid) resulted in a molecule not able to image the tumor at all (Eder et al., 2012). This is depicted in FIG. 10, wherein the tumor (in an LNCaP tumor model in balb/c nu/nu nude mice) is indicated by the arrow. Therefore, HBED-CC conjugates are particularly beneficial.

Example 4

The $^{68}$Ga-labeled compounds PSMA-HBED-CC-FITC (the compound depicted above), PSMA-Ahx-HBED-CC-cyanine 5.5 (the compound depicted above, of which the mass was determined by mass spectrometry as being M(calculated)=1642.98; M(found)=1642.7) and PSMA-Ahx-HBED-CC (the corresponding compound without cyanine 5.5) and were injected into an LNCaP tumor-bearing nude mice. One hour post injection, WET imaging was performed.

It could be shown that all three compounds showed comparable distribution of radioactivity and tumor uptake (cf., FIG. 11). Therefore, it could be demonstrated that the conjugation of the fluorescent dyes and insertion of a spacer do not significantly influence the distribution of radioactivity and tumor uptake of PSMA-HBED-CC-conjugates.

Example 5

PSMA-Ahx-HBED-CC-FITC (as shown above) was compared with a reference compound published by Banerjee et al. (Banerjee et al., 2011, Angew Chem Int Ed Engl. 50(39):9167-9170, page 6, scheme 1, final product) and the corresponding compound without the fluorescent dye IRDye800CW bearing a free amino group of the lysyl moiety the dye IRDye800CW can be bound to. These compounds were injected into LNCaP tumor-bearing nude mice.

It could be shown that the tumor uptake was significantly improved using PSMA-Ahx-HBED-CC-FITC (cf., FIG. 12). The absence of the fluorescent dye of the reference compound published by Banerjee et al. resulted in a significantly reduced kidney, spleen (both organs express PSMA), and tumor uptake of 0.71±0.03% ID/g (cf., FIG. 12).

Thus, this organ distribution study confirms that using branched compounds bears significant disadvantages such as diminished binding to the target structure unless these compounds such as the reference compound published by Banerjee et al. are not combined with the particular fluorophore structures such as IRDye800CW. Therefore, the structures known from Banerjee et al. are not usable in a modular manner. In particular, the dyes conjugated therewith are not freely selectable and several fluorophors regularly and preferably used in the art are not usable with the branched compounds as those shown by Banerjee et al. (Banerjee et al. (2011) and WO 2010/108125, in particularly not when the chelator is DOTA.

REFERENCES

WO 2010/108125
Afshar-Oromieh A, Malcher A, Eder M, Eisenhut M, Linhart H G, Hadaschik B A, Holland-Letz T, Giesel F L, Kratochwil C, Haufe S, Haberkorn U and Zechmann C M (2013a); PET imaging with a [68Ga]gallium-labelled PSMA ligand for the diagnosis of prostate cancer: biodistribution in humans and first evaluation of tumour lesions; Eur J Nucl Med Mol Imaging; 40(4):486-495.
Afshar-Oromieh A, Zechmann C M, Malcher A, Eder M, Eisenhut M, Linhart H G, Holland-Letz T, Hadacschik B A, Giesel F L, Debus J, Haberkorn U (2014); Comparison of PET imaging with a Ga-labelled PSMA ligand and F-choline-based PET/CT for the diagnosis of recurrent prostate cancer. Eur J Nucl Med Mol Imaging 41:11-20.
Banerjee S R, Pullambhatla M, Byun Y, Nimmagadda S, Foss C, Green G, Fox J J, Lupoid S E, Mease R, Pomper M G (2011); Sequential SPECT and optical imaging of experimental models of prostate cancer with a dual modality inhibitor of the prostate-specific membrane antigen. Angew Chem Int Ed Engl. 50(39):9167-9170.
Eder M, Wängler B, Knackmuss S, LeGall F, Little M, Haberkorn U, Mier W, Eisenhut M (2008); Tetrafluorophenolate of HBED-CC: a versatile conjugation agent for (68)Ga-labeled small recombinant antibodies. Eur J Nucl Med Mol Imaging 35(10):1878-1886.
Eder M, Krivoshein A V, Backer M, Backer J M, Haberkorn U, Eisenhut M (2010); ScVEGF-PEG-HBED-CC and scVEGF-PEG-NOTA conjugates: comparison of easy-to-label recombinant proteins for [68Ga]PET imaging of VEGF receptors in angiogenic vasculature. Nucl Med Biol, 37(4):405-412.
Eder M, Schäfer M, Bauder-Wüst U, Hull W E, Wängler C, Mier W, Haberkorn U and Eisenhut M (2012); $^{68}$Ga-complex lipophilicity and the targeting property of a urea-based PSMA inhibitor for PET imaging; Bioconjug Chem. 23(4):688-697.
Kolmakov K, Wurm C A, Meineke D N, Göttfert F, Boyarskiy V P, Belov V N, Hell S W (2014); Polar red-emitting rhodamine dyes with reactive groups: synthesis, photophysical properties, and two-color STED nanoscopy applications. Chem. Eur. J. 20:146-157.
Kolmakov K, Wurm C A, Hennig R, Rapp E, Jakobs S, Belov V N and Hell S W (2012); Red-emitting rhodamines with hydroxylated, sulfonated, and phosphorylated dye residues and their use in fluorescence nanoscopy. Chem. Eur. J. 18:12986-12998.
Kularatne, S A (2009); Design, synthesis, and preclinical evaluation of prostate-specific membrane antigen targeted (99m)Tc-radioimaging agents. Mol Pharm. 6(3):790-800.
Liu T, Toriyabe Y, Kazak M, Berkman C E (2008); Pseudoirreversible inhibition of prostate-specific membrane antigen by phosphoramidate peptidomimetics. Biochemistry, 47(48):12658-12660.
Schäfer M, Bauder-Wüst U, Leotta K, Zoller F, Mier W, Haberkorn U, Eisenhut M and Eder M (2012); A dimerized urea-based inhibitor of the prostate-specific membrane antigen for 68Ga-PET imaging of prostate cancer; EJNMMI Res. 2(1):23.
Schuhmacher J and Maier-Borst W (1981); A new $^{68}$Ge/$^{68}$Ga radioisotope generator system for production of $^{68}$Ga in dilute HCl; Int J Appl Radiat Isot 32:31-36.
Seibold U, Wängler B, Schirrmacher R and Wängler C (2014); Bimodal imaging probes for combined PET and OI: recent developments and future directions for hybrid agent development. Biomed Res Int. 2014:153741. doi: 10.1155/2014/153741.

What is claimed is:
1. A compound having the following chemical structure:

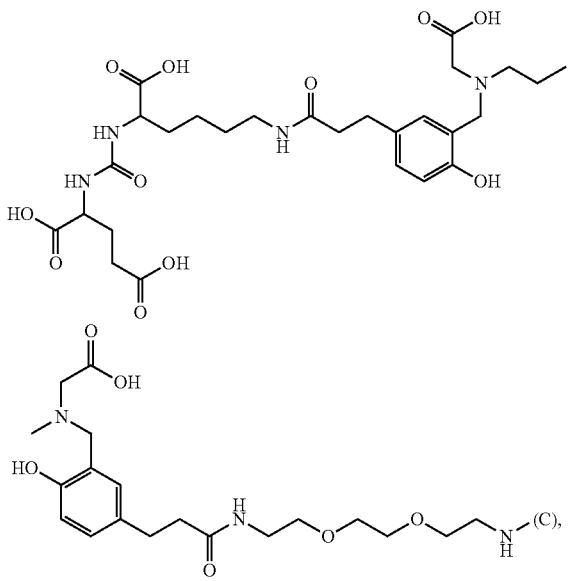

or a pharmaceutically acceptable salt thereof, wherein the residue (C) is a fluorescent dye moiety.

2. The compound or a pharmaceutically acceptable salt thereof according to claim 1, having the following chemical structure:

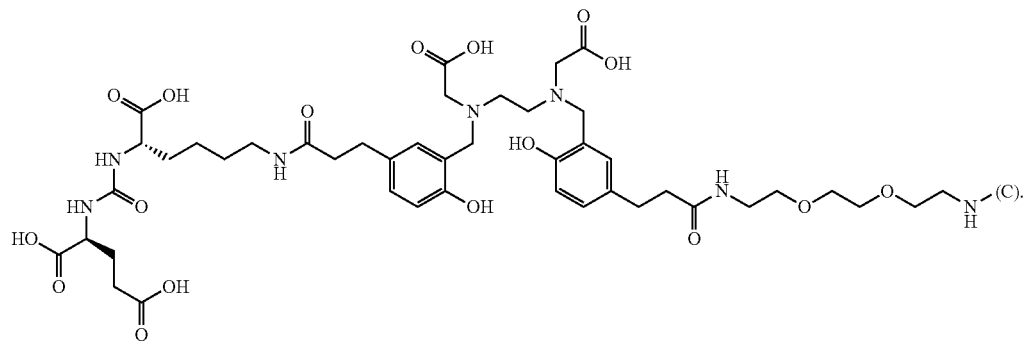

3. The compound or a pharmaceutically acceptable salt thereof according to claim 1, wherein said fluorescent dye moiety (C) is an infrared fluorescence dye.

4. The compound or a pharmaceutically acceptable salt thereof according to claim 1, wherein said fluorescent dye moiety (C) is IRDye 800CW.

5. A composition comprising:
 (a) the compound or a pharmaceutically acceptable salt thereof of claim 1;
 (b) a radiometal or a salt thereof; and optionally
 (c) one or more pharmaceutically acceptable carriers.

6. The composition according to claim 5, wherein the radiometal or a salt thereof is 68Ga or a salt thereof.

7. The composition according to claim 5, wherein the composition is useful as a diagnostic.

8. The composition according to claim 5, wherein the composition is usable in a method for diagnosing a neoplasm in a patient suffering therefrom.

9. The composition for use according to claim 5, wherein the neoplasia is cancer.

10. A kit comprising:
 (a) the compound or a pharmaceutically acceptable salt thereof according to claim 1; and
 (b) a user manual.

11. A kit comprising:
 (a) the composition according to claim 5; and
 (b) a user manual.

* * * * *